United States Patent
Zhang et al.

(10) Patent No.: US 10,188,623 B2
(45) Date of Patent: *Jan. 29, 2019

(54) ENHANCED BIOAVAILABILITY OF POLYUNSATURATED FATTY ACIDS

(71) Applicant: PATHEON SOFTGELS INC, High Point, NC (US)

(72) Inventors: Peijin Zhang, Oak Ridge, NC (US); Aqeel A. Fatmi, High Point, NC (US)

(73) Assignee: Patheon Signals Inc., High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,333

(22) Filed: Feb. 13, 2018

(65) Prior Publication Data

US 2018/0169050 A1    Jun. 21, 2018

Related U.S. Application Data

(63) Continuation of application No. 14/749,671, filed on Jun. 25, 2015, now Pat. No. 9,895,333, which is a (Continued)

(51) Int. Cl.
*A61K 9/48*    (2006.01)
*A61K 31/202*    (2006.01)
(Continued)

(52) U.S. Cl.
CPC .......... *A61K 31/202* (2013.01); *A61K 9/0053* (2013.01); *A61K 9/4825* (2013.01);
(Continued)

(58) Field of Classification Search
CPC .. A61K 9/4825; A61K 9/5057; A61K 9/5026; A61K 31/202
See application file for complete search history.

(56) References Cited

U.S. PATENT DOCUMENTS 5,146,730 A    9/1992    Sadek et al.
5,459,983 A    10/1995    Sadek et al.
(Continued)

FOREIGN PATENT DOCUMENTS

WO    WO2004030658 A1    4/2004
WO    WO2009009040 A2    1/2009
(Continued)

OTHER PUBLICATIONS

VASCEPA® Prescribing Information, Amarin Pharmaceuticals Ireland Limited, PP00120F Nov. 2013 (available http://www.vascepa.com/full-prescribing-information.pdf).

(Continued)

*Primary Examiner* — Lakshmi S Channavajjala
(74) *Attorney, Agent, or Firm* — Brinks Gilson & Lione

(57) ABSTRACT

Described herein are pharmaceutical compositions providing enhanced bioavailability of polyunsaturated fatty acids and methods of manufacturing the same. In particular, described herein are pharmaceutical compositions comprising soft enteric capsules that provide enhanced bioavailability of omega-3 polyunsaturated fatty acids. The oral pharmaceutical compositions described herein are useful as nutritional supplements or for the treatment of cardiovascular-related diseases, such as hyper dyslipidemia and moderate to high triglyceride levels.

20 Claims, 6 Drawing Sheets

Related U.S. Application Data continuation-in-part of application No. 14/527,201, filed on Oct. 29, 2014, now Pat. No. 9,895,332, and a continuation-in-part of application No. PCT/US2014/062892, filed on Oct. 29, 2014.

(60) Provisional application No. 62/017,489, filed on Jun. 26, 2014.

(51) Int. Cl.
| | | |
|---|---|---|
| *A61K 9/00* | (2006.01) | |
| *A61K 31/232* | (2006.01) | |
| *A61K 31/07* | (2006.01) | |
| *A61K 31/122* | (2006.01) | |
| *A61K 31/355* | (2006.01) | |
| *A61K 31/59* | (2006.01) | |
| *A61K 31/13* | (2006.01) | |
| *A61K 31/439* | (2006.01) | |
| *A61K 31/445* | (2006.01) | |

(52) U.S. Cl.
CPC ............ *A61K 9/4866* (2013.01); *A61K 31/07* (2013.01); *A61K 31/122* (2013.01); *A61K 31/13* (2013.01); *A61K 31/232* (2013.01); *A61K 31/355* (2013.01); *A61K 31/439* (2013.01); *A61K 31/445* (2013.01); *A61K 31/59* (2013.01)

(56) References Cited

U.S. PATENT DOCUMENTS

| | | |
|---|---|---|
| 5,502,077 A | 3/1996 | Breivik |
| 5,656,667 A | 8/1997 | Breivik et al. |
| 6,482,516 B1 | 11/2002 | Sadek et al. |
| 8,298,554 B2 | 10/2012 | Manku |
| 9,895,332 B2 * | 2/2018 | Zhang .................. A61K 31/202 |
| 9,895,333 B2 * | 2/2018 | Zhang .................. A61K 31/202 |
| 2005/0187292 A1 | 8/2005 | Aoki et al. |
| 2006/0165778 A1 | 7/2006 | Hassan et al. |
| 2007/0269507 A1 | 11/2007 | Sachetto et al. |
| 2010/0158958 A1 | 6/2010 | Chidambaram |
| 2010/0278879 A1 | 11/2010 | Manku |
| 2013/0115281 A1 | 5/2013 | Draper et al. |
| 2013/0177643 A1 | 7/2013 | Maines et al. |
| 2013/0209556 A1 | 8/2013 | Maines et al. |
| 2013/0280323 A1 | 10/2013 | Fang |
| 2015/0118298 A1 | 4/2015 | Zhang et al. |

FOREIGN PATENT DOCUMENTS

| | | |
|---|---|---|
| WO | WO2012013331 A1 | 2/2012 |
| WO | WO2012032414 A2 | 3/2012 |
| WO | WO2012032415 A2 | 3/2012 |
| WO | WO2012032417 A2 | 3/2012 |
| WO | WO2013150384 A1 | 10/2013 |
| WO | WO2015066176 A1 | 5/2015 |

OTHER PUBLICATIONS

International Search Report for PCT/US2015/037558, dated Sep. 25, 2015.

* cited by examiner ated Patent Application No. PCT/US2014/062892,
ENHANCED BIOAVAILABILITY OF POLYUNSATURATED FATTY ACIDS

CROSS REFERENCE TO RELATED APPLICATIONS

This application is continuation of U.S. application Ser. No. 14/749,671, filed Jun. 25, 2015, which is a continuation in part of U.S. patent application Ser. No. 14/527,201 and International Patent Application No. PCT/US2014/062892, both filed on Oct. 29, 2014 and both of which claim priority to U.S. Provisional Patent Application No. 62/017,489, filed Jun. 26, 2014. Each of these applications are incorporated by reference herein in their entirety.

TECHNICAL FIELD

Described herein are pharmaceutical compositions providing enhanced bioavailability of polyunsaturated fatty acids and methods of manufacturing the same. In particular, described herein are pharmaceutical compositions comprising soft enteric capsules that provide enhanced bioavailability of omega-3 polyunsaturated fatty acids. The oral pharmaceutical compositions described herein are useful as nutritional supplements or for the treatment of cardiovascular-related diseases, such as hyper dyslipidemia and high triglyceride levels.

BACKGROUND

Medical professionals are increasingly recognizing the positive cardiovascular health benefits of fish oil based products. The principle oral dosage form of fish oil is a soft gelatin capsules. However, a major limitation for consumers and patient compliance for the continued taking of these fish oil products is the presence of disruptive and unpleasant fishy odors associated with these traditional soft gelatin fish oil capsules. In particular, taking fish oil can result in negative side effects, including but not limited to, gastric disturbances such as fishy eructation (belching, e.g., "fishy burps"), gastrointestinal discomfort, bloating, nausea, diarrhea, unpleasant fishy odor, or unpleasant fishy aftertaste.

To minimize these negative side effects, consumers often will freeze their fish oil capsules before ingestion, which is thought to possibly help prevent break down of the capsule in the esophagus and stomach. Several commercial products offer enterically coated fish oil soft gelatin capsules to help circumvent capsule break down in the stomach. Other products include flavors or odor masking agents such as citrus or vanilla. However, these agents do not solve the negative side effects. In addition, there are significant problems associated with traditional enteric coated capsules.

The use and manufacture of coated enteric dosage forms are well known in the art. Such dosage forms are described in *Remington's Pharmaceutical Sciences*, 18th ed., Mack Publishing Co., Easton, Pa. (1990). Enteric dosage forms are useful for protecting the contents of the dosage form from the gastric conditions of the stomach and/or to protect gastric tissue from an irritant material contained in the dosage form.

Enteric-coated dosage forms are typically produced by a film coating process, where a thin film layer of an acid-insoluble (enteric) polymer is applied to the surface of a pre-manufactured dosage form, such as a tablet, and to a lesser extent, hard and soft capsules. The enteric coating method involves spraying an aqueous or organic solution or suspension of one or more enteric polymers onto tumbling or moving tablets or capsules, followed by drying at elevated temperatures. Enteric dosage forms made by this coating method can suffer from various process-related problems that affect the performance and/or appearance of the coating. For example, "orange peel" surface formation, also known as surface roughness or mottling, may result. More seriously, coat integrity failure may occur, such as cracking or flaking off the enteric polymer coating. All coating processes present inherent problems, including possible uneven distribution of the coating ingredients, which can occur under multivariate coating processes. Further, enteric coating also results in a hazy and opaque appearance of the capsule and requires additional manufacturing steps.

These problems are common to all enteric dosage forms. However, the problems faced during the coating of gelatin or polysaccharide capsules are even more critical due to the delicate and heat sensitive nature of the soft, elastic, capsule shell. Both hard and soft capsules can undergo thermally induced agglomeration and distortion of the capsule shell. Moreover, the smoothness and elasticity of the capsule surface makes it difficult to form an intact, adhered enteric coating, without a subcoating step to improve the surface of the capsule for coating. Finally, the enteric coatings cause the loss of the normally shiny and clear appearance of gelatin capsule shells, which is a major reason for the popularity and acceptance of gelatin capsules.

There is an unmet need for a cost effective, clear, non-coated enteric soft gel capsule dosage forms encapsulating omega fatty acids wherein the potential dosage form failure is greatly diminished, and where the form does not sacrifice gel mass elasticity when wet and is more stable and mechanically stronger after drying. Furthermore, there is an unmet need for highly bioavailable formulations for omega-3 fatty acid supplements and drugs.

SUMMARY

Described herein, are oral pharmaceutical compositions comprising omega fatty acids in soft capsule shells that have robust gastric acid resistance and provide enhanced bioavailability. Also described herein are oral pharmaceutical compositions comprising omega fatty acids that reduce fishy eructation (belching, e.g., "fishy burps"), unpleasant fishy odor, or unpleasant fishy aftertaste.

One embodiment described herein is an oral controlled release pharmaceutical composition providing enhanced bioavailability comprising an enteric soft capsule shell encapsulating a matrix fill comprising an omega-3 polyunsaturated fatty acid having enhanced bioavailability. In one aspect described herein, the matrix fill comprises eicosapentaenoic acid (EPA). In another aspect described herein, the matrix fill comprises about 94% EPA free fatty acid. In another aspect described herein, the matrix fill comprises about 250 mg to about 1000 mg of EPA. In another aspect described herein, the omega-3 polyunsaturated fatty acid does not substantially contain docosahexaenoic acid (DHA). In another aspect described herein, upon administration to a subject, in vivo absorption and bioavailability of the omega-3 polyunsaturated fatty acid is uneffected by the presence of food in the subject's gastrointestinal tract. In another aspect described herein, the composition reduces the onset or ameliorates the symptoms of any gastrointestinal side effects including, but not limited to, eructation, abdominal discomfort, nausea, diarrhea, fishy aftertaste, or fishy odor. In another aspect described herein, the capsule shell and matrix fill composition are stable for at least 1 year at 25° C., 60% relative humidity. In another aspect described herein, the capsule shell does not dissolve in simulated gastric fluid (pH 1.2) for at least 1 hour, and begins dissolution in simulated intestinal fluid (pH 6.8) within about 15 minutes. In another aspect described herein, upon administration to a subject the composition provides one or more of the following pharmacokinetic parameters: (a) a mean plasma EPA $T_{max}$ of about 5 hours to about 6 hours; (b) a mean plasma EPA $C_{max}$ of about 122 mg/L to about 226 mg/L; (c) a mean plasma EPA $AUC_{0\to\tau}$ of about 1840 h·mg/L to about 2860 h·mg/L; (d) a mean plasma EPA $AUC_{0\to\infty}$ of about 2040·mg/L to about 3000 mg/L; (e) a mean EPA half-life (t½) of about 37 hours to about 43 hours; or (f) a mean EPA overall elimination rate constant ($k_{e1}$) of about 0.019 h−1 to about 0.020 $h^{-1}$. In another aspect described herein, upon administration to a subject the composition provides one or more of the following pharmacokinetic parameters: (a) a mean plasma EPA $T_{max}$ of about 6 hours under fasting/low fat conditions; (b) a mean plasma EPA $C_{max}$ of about 122 mg/L under fasting/low fat conditions; (c) a mean plasma EPA $AUC_{0\to\tau}$ of about 1840 h·mg/L under fasting/low fat conditions; (d) a mean plasma EPA $AUC_{0\to\infty}$ of about 2040·mg/L under fasting/low fat conditions; (e) a mean EPA half-life (t½) of about 43 h under fasting/low fat conditions; or (f) a mean EPA overall elimination rate constant ($k_{e1}$) of about 0.019 $h^{-1}$ under fasting/low fat conditions; or (g) a mean plasma EPA $T_{max}$ of about 5 hours under fed/high fat conditions; (h) a mean plasma EPA $C_{max}$ of about 226 mg/L under fed/high fat conditions; (i) a mean plasma EPA $AUC_{0\to\tau}$ of about 2860 h·mg/L under fed/high fat conditions; (j) a mean plasma EPA $AUC_{0\to\infty}$ of about 3000 mg/L under fed/high fat conditions; (k) a mean EPA half-life (t½) of about 37 hours under fed/high fat conditions; or (l) a mean EPA overall elimination rate constant ($k_{e1}$) of about 0.020 $h^{-1}$ under fed/high fat conditions. In another aspect described herein, upon administration to a subject the EPA has a bioavailability of greater than 50% of the bioavailability of a reference pharmaceutical composition. In another aspect described herein, upon administration to a subject the EPA has a bioavailability of greater than 70% of the bioavailability of a reference pharmaceutical composition under fed conditions. In another aspect described herein, upon administration to a subject the EPA has a bioavailability of greater than 100% of the bioavailability of a reference pharmaceutical composition under fasted/low fat conditions. In another aspect described herein, upon administration to a subject the EPA has a bioavailability of about 2000% of the bioavailability of a reference pharmaceutical composition under fasted/low fat conditions. In another aspect described herein, the reference pharmaceutical composition comprises EPA ethyl ester in a soft gel capsule. In another aspect described herein, upon administration to a subject, the composition does not induce a substantial increase in LDL level relative to baseline. In another aspect described herein, the composition is useful for treating, retarding the progression of, delaying the onset of, prophylaxis of, amelioration of, or reducing the symptoms of a cardiovascular-related disease, including but not limited to hyperlipidemia or hypertriglyceridemia. In another aspect described herein, the composition is useful for treating, retarding the progression of, delaying the onset of, prophylaxis of, amelioration of, or reducing the symptoms a medical condition comprising: cardiovascular-related diseases, hyperlipidemia, hypertriglyceridemia, hypertension, hypercholesterolemia, mixed dyslipidemia, sitosterolemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), ventricular arrhythmias, angina pectoris, unstable angina (UA), and stable angina (SA), myocardial infarction, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, peripheral vascular disease, and peripheral artery disease, rheumatoid arthritis, dysmenorrhea, attention deficit-hyperactivity disorder in children, attention deficit-hyperactivity disorder in adults, Raynaud's syndrome, stroke, osteoporosis, kidney problems, bipolar disorder, psychosis, weight loss, endometrial cancer, macular degeneration, kidney damage, dyspraxia, developmental coordination disorder, psoriasis, asthma, allergies, Alzheimer's disease, atopic dermatitis, atrial fibrillation, depression, dry eye syndrome, cataracts, chronic fatigue syndrome (CFS), chronic kidney disease, Crohn's disease, prediabetes, ulcerative colitis, salicylate intolerance, schizophrenia, systemic lupus erythematosus (SLE), or a combination thereof. In another aspect described herein, the enteric soft capsule shell comprises a film forming polymer, one or more enteric polymers, one or more plasticizers, one or more alkali neutralizing agents, one or more solvents, and optionally an opacifier, a filler, a coloring agent, a flavoring agent, or a pharmaceutically acceptable excipient. In another aspect described herein, the one or more film forming polymers comprises gelatin, the one or more enteric polymers comprises acrylic and methacrylic acid copolymers; the one or more plasticizers comprises glycerol and triethyl citrate; the one or more solvents comprises water; the alkali neutralizing agent comprises ammonium hydroxide; and the optional opacifier comprises titanium dioxide. In another aspect described herein, the enteric soft capsule shell comprises: about 25% to about 40% gelatin; about 9% to about 11% acrylic and methacrylic acid copolymers; about 10% to about 20% glycerol; about 1% to about 3% triethyl citrate; about 1% to about 4% ammonium hydroxide; and about 19% to about 65% water. In another aspect described herein, the enteric soft capsule shell comprises: about 30% gelatin; about 18% glycerol; about 1% triethyl citrate; about 10% poly(methacylic acid-co-methyl methacrylate) 1:1; about 1.5% ammonium hydroxide; and about 38% water. In another aspect described herein, an initial peroxide concentration is not more than about 10 meq/kg and a second peroxide concentration after storage for about 24 months at 25° C., 60% relative humidity is not more than about 25 meq/kg.

Another embodiment described herein is an oral pharmaceutical composition comprising an enteric soft capsule comprising about 1000 mg of about 94% eicosapentaenoic acid (EPA, free fatty acid). In another aspect described herein, the enteric soft capsule comprising: about 25% to about 40% gelatin; about 9% to about 11% acrylic and methacrylic acid copolymers; about 10% to about 20% glycerol; about 1% to about 3% triethyl citrate; about 1% to about 4% ammonium hydroxide; and about 19% to about 65% water. In one aspect described herein, upon administration to a subject, the in vivo absorption and bioavailability of the eicosapentaenoic acid is uneffected by the presence of food in the subject's gastrointestinal tract. In another aspect described herein, upon administration to a subject the composition provides one or more of the following pharmacokinetic parameters: (a) a mean plasma EPA $T_{max}$ of about 5 hours to about 6 hours; (b) a mean plasma EPA $C_{max}$ of about 122 mg/L to about 226 mg/L; (c) a mean plasma EPA AUC$_{0\to\infty}$ of about 1840 h·mg/L to about 2860 h·mg/L; (d) a mean plasma EPA AUC$_{0\to\infty}$ of about 2040·mg/L to about 3000 mg/L; (e) a mean EPA half-life (t½) of about 37 hours to about 43 hours; or (f) a mean EPA overall elimination rate constant (k$_{e1}$) of about 0.019 h−1 to about 0.020 h$^{-1}$. In another aspect described herein, upon administration to a subject the EPA has a bioavailability of greater than 50% of the bioavailability of a reference pharmaceutical composition. In another aspect described herein, upon administration to a subject the EPA has a bioavailability of greater than 70% of the bioavailability of a reference pharmaceutical composition under fed conditions. In another aspect described herein, upon administration to a subject the EPA has a bioavailability of greater than 100% of the bioavailability of a reference pharmaceutical composition under fasted/low fat conditions. In another aspect described herein, upon administration to a subject the EPA has a bioavailability of about 2000% of the bioavailability of a reference pharmaceutical composition under fasted/low fat conditions. In another aspect described herein, the reference pharmaceutical composition comprises EPA ethyl ester in a soft gel capsule. In another aspect described herein, upon administration to a subject, the composition does not induce a substantial increase in LDL level relative to baseline. In another aspect described herein, the pharmaceutical composition exhibits a 50% in vitro dissolution rate (% dissolution per minute) at pH 6.8, of about 20 minutes. In another aspect described herein, the composition is useful for treating, retarding the progression of, delaying the onset of, prophylaxis of, amelioration of, or reducing the symptoms of a cardiovascular-related disease including, but not limited to, hyperlipidemia or hypertriglyceridemia, without substantially inducing one or more of one or more of eructation, abdominal discomfort, nausea, diarrhea, or unpleasant fishy odor. In another aspect described herein, the composition is useful for treating, retarding the progression of, delaying the onset of, prophylaxis of, amelioration of, or reducing the symptoms of a medical condition comprising: cardiovascular-related diseases, hyperlipidemia, hypertriglyceridemia, hypertension, hypercholesterolemia, mixed dyslipidemia, sitosterolemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), ventricular arrhythmias, angina pectoris, unstable angina (UA), and stable angina (SA), myocardial infarction, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, peripheral vascular disease, and peripheral artery disease, rheumatoid arthritis, dysmenorrhea, attention deficit-hyperactivity disorder in children, attention deficit-hyperactivity disorder in adults, Raynaud's syndrome, stroke, osteoporosis, kidney problems, bipolar disorder, psychosis, weight loss, endometrial cancer, macular degeneration, kidney damage, dyspraxia, developmental coordination disorder, psoriasis, asthma, allergies, Alzheimer's disease, atopic dermatitis, atrial fibrillation, depression, dry eye syndrome, cataracts, chronic fatigue syndrome (CFS), chronic kidney disease, Crohn's disease, prediabetes, ulcerative colitis, salicylate intolerance, schizophrenia, systemic lupus erythematosus (SLE), or a combination thereof, without substantially inducing one or more of one or more of eructation, abdominal discomfort, nausea, diarrhea, or unpleasant fishy odor. In another aspect described herein, the composition for administration to a subject with hyperdyslipidemia or a cardiovascular-related disease comprising a therapeutically effective amount of the fatty acids described herein, wherein the subject achieves a reduction of the annualized disease relapse rate relative to baseline without substantially experiencing one or more of disruptive eructation and unpleasant fishy odors and aftertaste. In another embodiment described herein, the reduction is up to 50% or greater.

Another embodiment described herein is a method for treating, retarding the progression of, delaying the onset of, prophylaxis of, amelioration of, or reducing the symptoms of a cardiovascular-related disease including, but not limited to, hyperlipidemia or hypertriglyceridemia, comprising the administration of a therapeutically effective amount of EPA free fatty acid comprising any of the pharmaceutical compositions described herein.

Another embodiment described herein is a method for treating, retarding the progression of, delaying the onset of, prophylaxis of, amelioration of, or reducing the symptoms of a cardiovascular-related disease including, but not limited to, hyperlipidemia or hypertriglyceridemia, comprising the administration to a subject in need thereof of one or more oral dosage forms comprising an enteric soft capsule comprising about 1000 mg of about 94% eicosapentaenoic acid (EPA, free fatty acid). In another aspect described herein, the administration comprises equal doses of about 1000 mg per day to about 4000 mg per day. In another aspect described herein, the enteric soft capsule comprises: about 25% to about 40% gelatin; about 9% to about 11% acrylic and methacrylic acid copolymers; about 10% to about 20% glycerol; about 1% to about 3% triethyl citrate; about 1% to about 4% ammonium hydroxide; and about 19% to about 65% water. In another aspect described herein, the administration is sufficient to achieve a reduction of triglyceride (TG) levels of about 25% relative to baseline in the subject without substantially inducing one or more gastrointestinal side effects including but not limited to eructation, abdominal discomfort, nausea, diarrhea, fishy aftertaste, or fishy odor. In another aspect described herein, the administration does not induce a substantial increase in LDL level relative to baseline. In another aspect described herein, the cardiovascular-related disease comprises: hyperlipidemia, hypertriglyceridemia, hypertension, hypercholesterolemia, mixed dyslipidemia, sitosterolemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), ventricular arrhythmias, angina pectoris, unstable angina (UA), and stable angina (SA), myocardial infarction, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, peripheral vascular disease, and peripheral artery disease, rheumatoid arthritis, dysmenorrhea, attention deficit-hyperactivity disorder in children, attention deficit-hyperactivity disorder in adults, Raynaud's syndrome, stroke, osteoporosis, kidney problems, bipolar disorder, psychosis, weight loss, endometrial cancer, macular degeneration, kidney damage, dyspraxia, developmental coordination disorder, psoriasis, asthma, allergies, Alzheimer's disease, atopic dermatitis, atrial fibrillation, depression, dry eye syndrome, cataracts, chronic fatigue syndrome (CFS), chronic kidney disease, Crohn's disease, prediabetes, ulcerative colitis, salicylate intolerance, schizophrenia, systemic lupus erythematosus (SLE), or a combination thereof.

In another aspect described herein, in vivo absorption and bioavailability of the eicosapentaenoic acid is uneffected by the presence of food in the subject's gastrointestinal tract. In another aspect described herein, the pharmaceutical composition provides one or more of the following pharmacokinetic parameters: (a) a mean plasma EPA $T_{max}$ of about 5 hours to about 6 hours; (b) a mean plasma EPA $C_{max}$ of about 122 mg/L to about 226 mg/L; (c) a mean plasma EPA $AUC_{0 \to \tau}$ of about 1840 h·mg/L to about 2860 h·mg/L; (d) a mean plasma EPA $AUC_{0 \to \infty}$ of about 2040 mg/L to about 3000 mg/L; (e) a mean EPA half-life (t½) of about 37 hours to about 43 hours; or (f) a mean EPA overall elimination rate constant ($k_{el}$) of about 0.019 h–1 to about 0.020 $h^{-1}$. In another aspect described herein, upon administration to the subject the EPA has a bioavailability of greater than 50% of the bioavailability of a reference pharmaceutical composition. In another aspect described herein, upon administration to the subject the EPA has a bioavailability of greater than 70% of the bioavailability of a reference pharmaceutical composition under fed conditions. In another aspect described herein, upon administration to the subject the EPA has a bioavailability of greater than 100% of the bioavailability of a reference pharmaceutical composition under fasted/low fat conditions. In another aspect described herein, upon administration to a subject the EPA has a bioavailability of about 2000% of the bioavailability of a reference pharmaceutical composition under fasted/low fat conditions. In another aspect described herein, the reference pharmaceutical composition comprises EPA ethyl ester in a soft gel capsule. In another aspect described herein, upon administration to a subject, the composition does not induce a substantial increase in LDL level relative to baseline. In another aspect described herein, the dosage form exhibits a 50% in vitro dissolution rate (% dissolution per minute) at pH 6.8, of about 20 minutes. In another aspect described herein, the dosage from is administered for at least about 10 days. In another aspect described herein, LDL-C levels are reduced by at least about 5%. In another aspect described herein, HDL-C levels are reduced by at least about 5%. In another aspect described herein, plasma concentration of arachidonic acid is reduced by at least about 5%. In another aspect described herein, apo A-I/apo B ratio is increased by at least about 5%. In another aspect described herein, the dosage form further comprises a therapeutically effective amount of one or more non-steroidal anti-inflammatory drugs, statins, or cardiovascular drugs. In another aspect described herein, the administration is sufficient to achieve a reduction of the annualized disease relapse rate relative to baseline without substantially experiencing one or more of disruptive eructation and unpleasant fishy odors and aftertaste. In another aspect described herein, the reduction is up to 50% or greater.

Another embodiment described herein is a method for manufacturing an oral pharmaceutical dosage form comprising an enteric soft capsule shell and a matrix fill comprising a fatty acid composition comprising the steps of: (i) providing a matrix fill comprising about 1000 mg of about 94% eicosapentaenoic acid (EPA, free fatty acid); (ii) providing an enteric soft capsule shell comprising about 25% to about 40% gelatin; about 9% to about 11% acrylic and methacrylic acid copolymers; about 10% to about 20% glycerol; about 1% to about 3% triethyl citrate; about 1% to about 4% ammonium hydroxide; and about 19% to about 65% water; (iii) casting the enteric soft capsule shell into films using heat-controlled drums or surfaces; and (iv) forming an enteric soft capsule dosage form comprising the matrix fill composition using rotary die encapsulation technology.

Another embodiment described herein is an oral pharmaceutical dosage form produced by any of the compositions or the methods described herein.

Another embodiment described herein is a kit for dispensing the oral pharmaceutical dosage form produced by any of the compositions or the methods described herein comprising: (a) at least one dosage form comprising a fatty acid composition; (b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally (c) an insert comprising instructions or prescribing information for the fatty acid composition comprised by the oral pharmaceutical composition; or (d) an non-steroidal anti-inflammatory drug, a statin, or a cardiovascular drug. In one aspect described herein, the kit is useful for treating a cardiovascular-related disease or medical condition according to any of the methods described herein.

DETAILED DESCRIPTION

Figure 1:
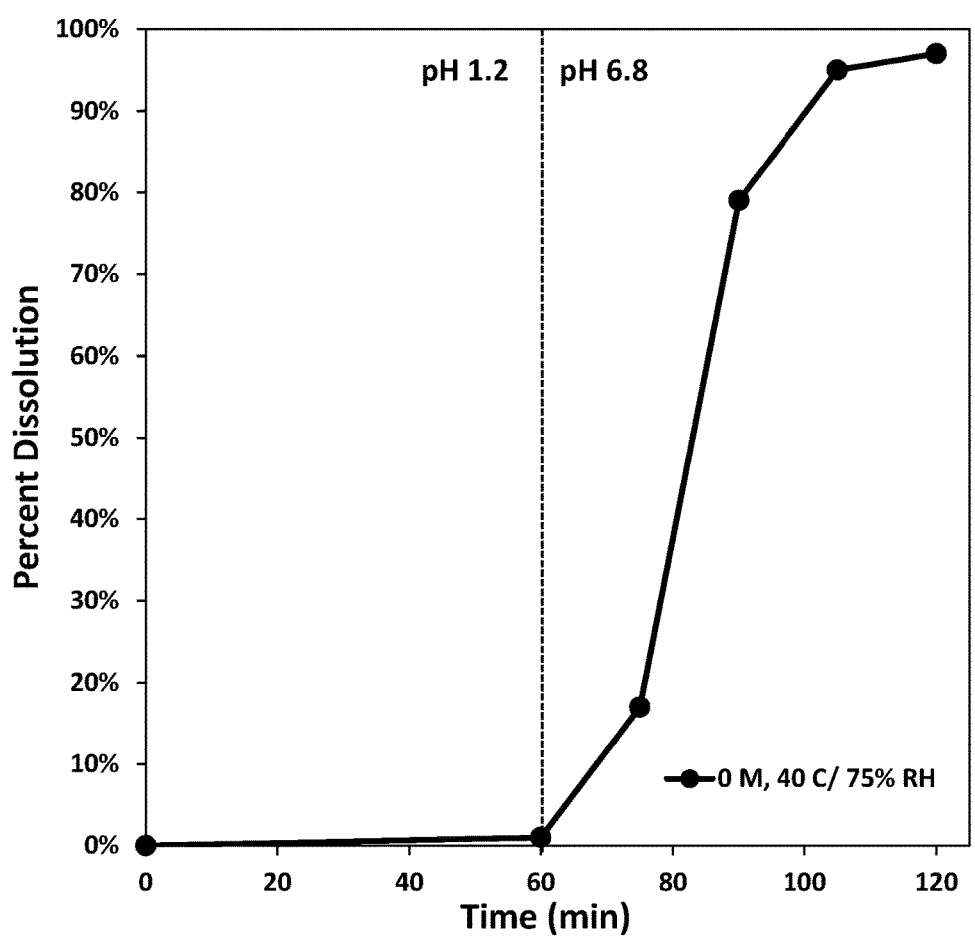
FIG. 1. Two-stage dissolution of the pharmaceutical composition shown in Table 6 (94% EPA free fatty acid in enteric soft gel capsules). The sample was placed in simulated gastric fluid (pH 1.2) for 1 hour and then transferred to simulated intestinal fluid (pH 6.8). The Tho is 82.6 minutes, which is 22.6 minutes after the transition to pH 6.8.
Figure 2:
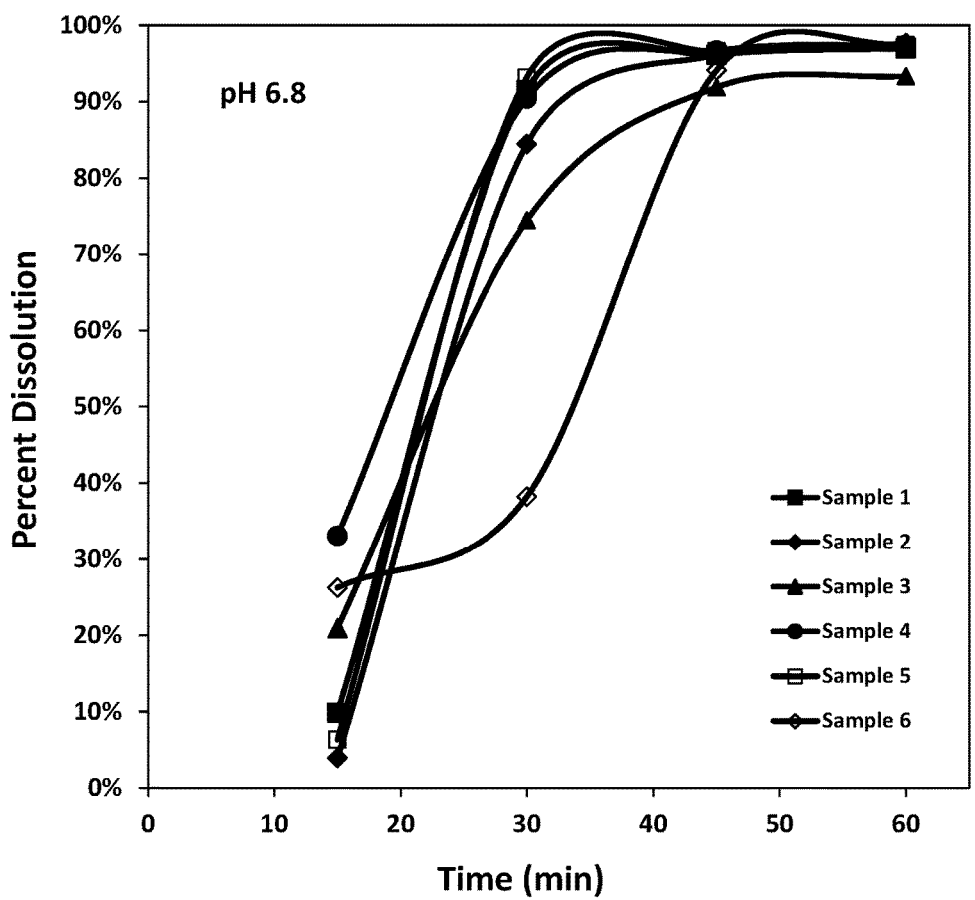
FIG. 2. Single-stage dissolution of six samples of the pharmaceutical composition shown in Table 6 at pH 6.8.
Figure 3:
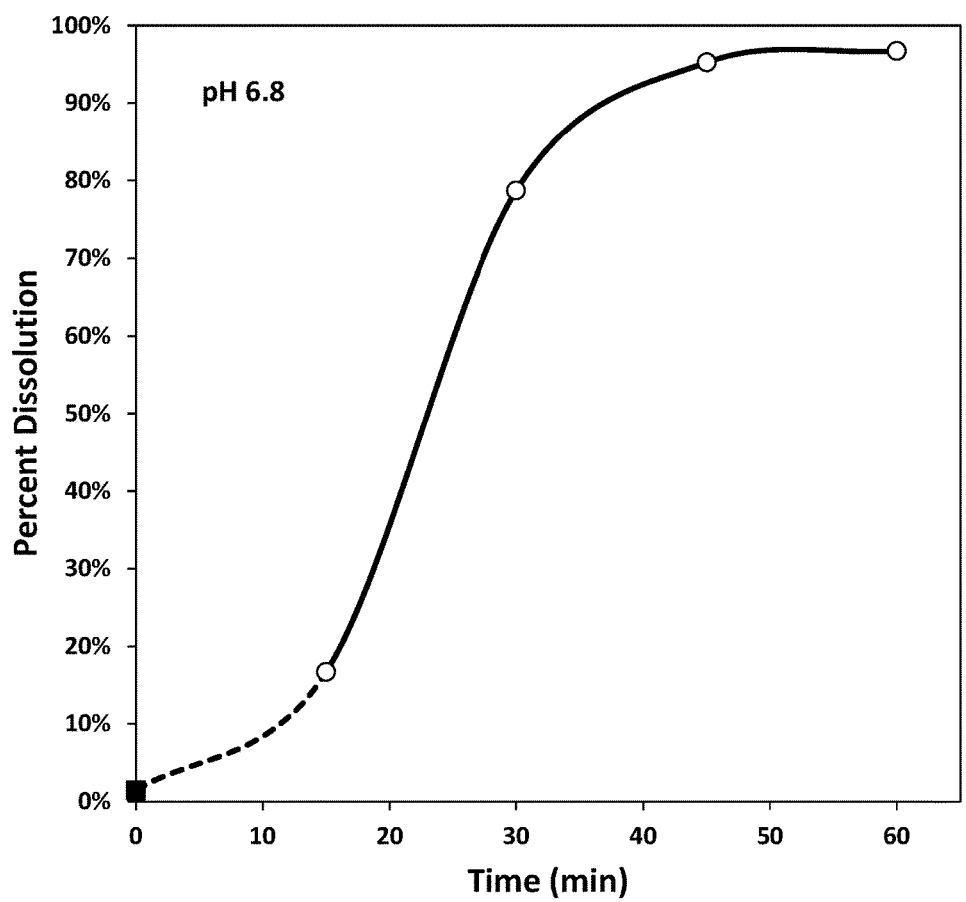
FIG. 3. Average of single-stage dissolution of the data in FIG. 2. The first point at zero is in pH 1.2 and then the capsules were transferred to pH 6.8. The $T_{50}$ is 22.6 minutes at pH 6.8.
Figure 4:
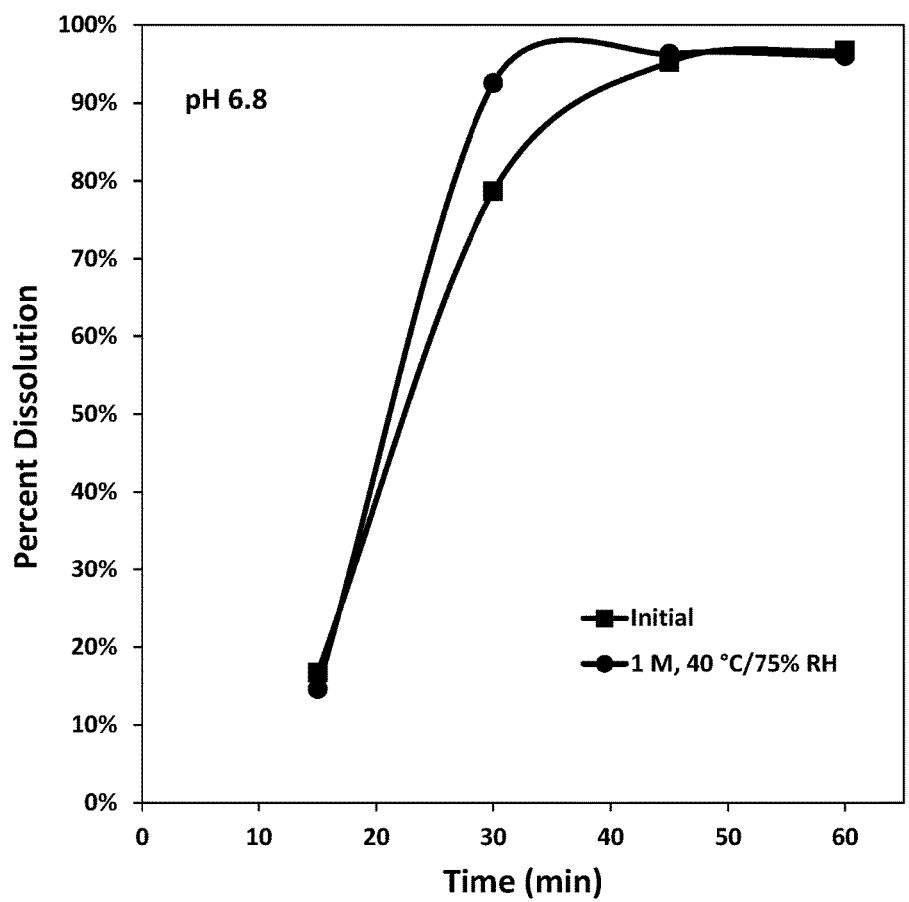
FIG. 4. Single-stage dissolution of samples of the pharmaceutical composition shown in Table 6 shortly after manufacturing and after 1 month under accelerated stability conditions (40° C., 75% relative humidity).
Figure 5:
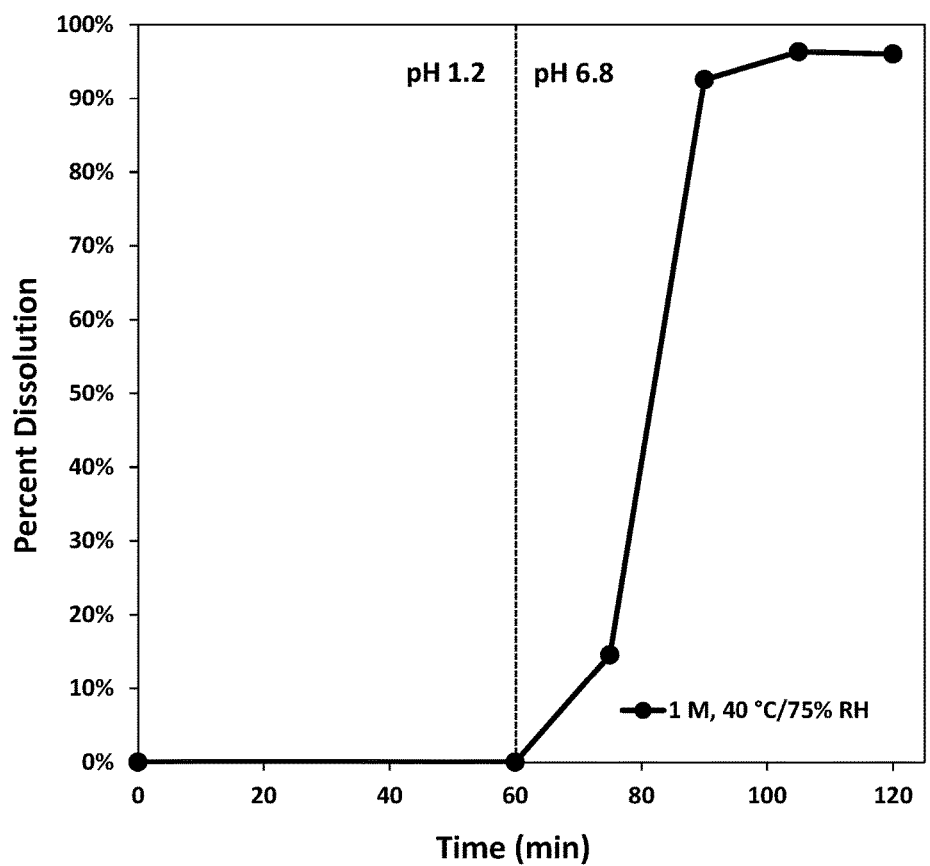
FIG. 5. Two-stage dissolution of the pharmaceutical composition shown in Table 6 after 1 month under accelerated stability conditions (40° C., 75% relative humidity). The sample was placed in simulated gastric fluid (pH 1.2) for 1 hour and then transferred to simulated intestinal fluid (pH 6.8). The $T_{50}$ is 79.9 minutes, which is 19.9 minutes after the transition to pH 6.8.

Described herein are pharmaceutical compositions or nutritional supplements comprising at least one or more polyunsaturated fatty acids encapsulated by a gastric-resistant or enteric soft capsule shell. The described pharmaceutical compositions provide surprising and unexpectedly high bioavailability of omega-3 fatty acids for the treatment of hyper dyslipidemia and high triglyceride levels.

As used herein, the phrase "pharmaceutical composition" encompasses "nutritional compositions" or "nutritional supplements."

As used herein, the terms "gastric-resistant" and "enteric" are used interchangeably and refer to the property of a substance resistant dissolution in biological, artificial, or simulated gastric fluid (pH ca. 1.2), and that dissolves in biological, artificial, or simulated intestinal fluid (pH ca. 6.8). One embodiment described herein are gastric-resistant or enteric soft capsules.

As used herein, the term "fatty acid" refers to any carboxylic acid having a long aliphatic chain that can be either saturated or unsaturated. The term fatty acid further encompasses any fish oil described herein and any saturated, polyunsaturated, monounsaturated, or any omega-3, -6, -7, or -9 fatty acid.

As used herein, the term "bioavailability" refers to the proportion of an active pharmaceutical ingredient that enters the systemic circulation when introduced into the body and is able to have a physiological effect.

As used herein, the term "enhanced bioavailability" refers to the increased proportion of an active pharmaceutical ingredient that enters the systemic circulation when introduced into the body as compared to a reference's bioavailability.

As used herein, the term "absolute bioavailability" refers to the fraction of a drug or active pharmaceutical ingredient absorbed through non-intravenous administration (e.g., oral administration) as compared to intravenous administration of the same drug or active pharmaceutical ingredient.

As used herein, the term "polyunsaturated fatty acid" ("PUFA") refers to a long chain fatty acid that contains more than one double bond in the backbone of the chain. The term encompasses esters, re-esterified triglycerides, or salts thereof.

As used herein, the term "monounsaturated fatty acid" refers to a long chain fatty acid that contains only one double bond in the backbone of the chain. The term encompasses esters, re-esterified triglycerides, or salts thereof.

As used herein, the term "all-natural" refers to the enteric soft capsule shell and means that the enteric soft capsule shell does not comprise any synthetic or artificial components.

As used herein, the terms "active ingredient," "active pharmaceutical ingredient," or "active pharmaceutical agent" refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable free acids, free bases, salts or esters.

As used herein, the terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

As used herein, the phrases "enteric soft capsule composition," "enteric soft capsule gel mass," "gel mass," or "enteric soft capsule shell" are used interchangeably and have the same meaning. Typically, as used herein, "enteric soft capsule composition" or "gel mass" refer to enteric soft capsule compositions prior to forming the enteric soft capsule and "enteric soft capsule shell" refers to the enteric capsule shell after having been formed into an enteric soft capsule, for example, by using rotary die encapsulation and the matrix fills described herein that have been introduced into said soft capsule shell.

As used herein, the term "pharmaceutical composition" refers a composition comprising at least on active ingredient, nutraceutical, nutritional, or vitamin. In some embodiments described herein, a pharmaceutical composition comprises a soft capsule shell having been formed into a capsule, for example, using rotary die encapsulation comprising one or more polyunsaturated fatty acids, optionally with one or more vitamins, antioxidants, or other active ingredients.

The term "formulation" or "composition" as used herein refers to the active pharmaceutical ingredient, nutraceutical, nutritional, vitamin, or drug in combination with pharmaceutically acceptable excipients. This includes orally administrable formulations as well as formulations administrable by other means.

The term "controlled release" as used herein refers to a composition that does not immediately releases an active ingredient. "Controlled release" as used herein encompasses the terms "modified release," "sustained release," "extended release," and "delayed release."

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours; about 24 hours; or even longer.

The term "modified release" as used herein refers to a composition that releases an active ingredient at a slower rate than does an immediate release formulation under physiological conditions or in an in vitro test.

The term "sustained release" as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically over a period of at least 18 hours under physiological conditions or in an in vitro assay.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0\to\infty}$" as used herein refers to the area under the blood (plasma, serum, or whole blood) concentration versus time curve from time 0 hours to infinity, and is expressed in units of h·mg/L or h·ng/mL, as applicable.

The term "room temperature" as used herein refers to common ambient temperatures ranging from about 20° C. to about 27° C.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any values, including both integers and fractional components that are within a variation of up to ±10% of the value modified by the term "about." For example, the phrase "about 50%" is equivalent to any value≈50±10%, e.g., 44.6%, 45%, 46%, 47%, 48%, 49%, 49.5%, 50%, 50.3%, 51%, 52%, 53%, 54%, 55%, inter alia.

As used herein, "a" or "an" means one or more unless otherwise specified.

Terms such as "include," "including," "contain," "containing," "has," or "having," and the like, mean "comprising."

The term "or" can be conjunctive or disjunctive.

Suitable active pharmaceutical ingredients comprising fatty acids for the oral pharmaceutical composition described herein comprise fish oils, egg oils, squid oils, krill oils, nut oils, seed oils; soy oils, avocado oils, seabuckthorn seed or berry oils, clary sage seed oils, algal oils, flaxseed oils, sacha ichi oils, echium oils, or hemp oils.

In one embodiment, active pharmaceutical ingredients comprising fatty acids are obtained from fish oils. Suitable fish for extracting fish oil comprise herring, sardines, mackerel (e.g., Spanish, king, Atlantic, or Pacific mackerel), salmon, halibut, tuna, swordfish, greenshell mussels, tilefish, tuna, pollock, cod, catfish, flounder, grouper, mahi mahi, orange roughy, red snapper, shark, hoki, gemfish, blue eye cod, Sydney rock oysters, snapper, or combinations thereof. In one aspect, the fatty acids comprise polyunsaturated fatty acids (PUFAs). In one aspect, PUFAs are obtained from fish comprising salmon, herring, mackerel, anchovies, or sardines.

Other useful pharmaceutical ingredients that can be included in the pharmaceutical compositions described herein include fish oils, egg oils, squid oils, krill oils, nut oils, seed oils; soy oils, avocado oils, seabuckthorn seed or berry oils, clary sage seed oils, algal oils, flaxseed oils, sacha ichi oils, echium oils, hemp oils, polyunsaturated fatty acids, omega-3 fatty acids, polyunsaturated omega-3 fatty acids, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA), clupanodonic acid), docosahexaenoic acid (DHA, cervonic acid), tetracosapentaenoic acid, tetracosahexaenoic acid (nisinic acid), and free acids, etheyl esters, or other esters or salts thereof. In one aspect, the pharmaceutical ingredient is a highly purified omega-3 fatty acid, ester, or salt thereof. In one aspect described herein, the active pharmaceutical ingredient comprises the polyunsaturated omega-3 free fatty acid, eicosapentaenoic acid (EPA).

In another embodiment, the pharmaceutical composition can comprise vitamins or minerals. "Vitamins" as used herein refers to nutraceuticals or pharmaceutical ingredients comprising organic substances that are typically considered essential for the normal growth and activity of a subject (e.g., a human or non-human animal patient to whom the composition is to be administered). Non-limiting examples of vitamins include, but are not limited to vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, and para-aminobenzoic acid.

Vitamins can also include naturally occurring inorganic substances such as "minerals" that are typically considered essential for the normal growth and activity of a subject (e.g., a human or non-human animal patient to whom the composition is to be administered). Examples of minerals include, but are not limited to, boron, calcium, chromium, copper, iron, magnesium, manganese, molybdenum, nickel, phosphorus, selenium, silicon, tin, vanadium, and zinc.

In one embodiment, the pharmaceutical compositions described herein comprise fatty acid compositions comprising omega-3 fatty acids or polyunsaturated omega-3 fatty acids comprising hexadecatrienoic acid (HTA; all-cis 7,10,13-hexadecatrienoic acid), alpha-linolenic acid (ALA; all-cis-9,12,15-octadecatrienoic acid), stearidonic acid (SDA; all-cis-6,9,12,15,-octadecatetraenoic acid), eicosatrienoic acid (ETE; all-cis-11,14,17-eicosatrienoic acid), eicosatetraenoic acid (ETA; all-cis-8,11,14,17-eicosatetraenoic acid), eicosapentaenoic acid (EPA, timnodonic acid; all-cis-5,8,11,14,17-eicosapentaenoic acid), heneicosapentaenoic acid (HPA; all-cis-6,9,12,15,18-heneicosapentaenoic acid), docosapentaenoic acid (DPA, clupanodonic acid; all-cis-7,10,13,16,19-docosapentaenoic acid), docosahexaenoic acid (DHA, cervonic acid; all-cis-4,7,10,13,16,19-docosahexaenoic acid), tetracosapentaenoic acid (all-cis-9,12,15,18,21-tetracosapentaenoic acid), tetracosahexaenoic acid (nisinic acid; all-cis-6,9,12,15,18,21-tetracosahexaenoic acid), and free acids, etheyl esters, or other esters or salts thereof. In one aspect, the pharmaceutical ingredient comprises a highly purified omega-3 free fatty acid, ester, re-esterified triglyceride, or salt thereof. In one aspect, the pharmaceutical ingredient comprises a highly purified omega-3 free fatty acid.

In another embodiment, the pharmaceutical compositions described herein comprise polyunsaturated fatty acid compositions (PUFAs) comprising omega-6 fatty acids or polyunsaturated omega-6 fatty acids comprising linoleic acid (LA; all-cis-9,12-octadecadienoic acid), gamma-linolenic acid (GLA; all-cis-6,9,12-octadecatrienoic acid), calendic acid (8E,10E,12Z-octadecatrienoic acid), eicosadienoic acid (all-cis-11,14-eicosadienoic acid), dihomo-gamma linolenic acid (DGLA; all-cis-8,11,14-eicosatrienoic acid), arachidonic acid (AA; all-cis-5,8,11,14-eicosatetraenoic acid), docosadienoic acid (all-cis-13,16-docosadienoic acid), adrenic acid (all-cis-7,10,13,16-docosatetraenoic acid), docosapentaenoic acid (osbond acid; all-cis-4,7,10,13,16-docosapentaenoic acid), tetracosatetraenoic acid (all-cis-9,12,15,18-tetracosatetraenoic acid), tetracosapentaenoic acid (all-cis-6,9,12,15,18-tetracosapentaenoic acid) and free acids, etheyl esters, or other esters or salts thereof. In one aspect, the pharmaceutical ingredient comprises a highly purified omega-6 fatty acid, ester, re-esterified triglyceride, or salt thereof.

In another embodiment described herein, the pharmaceutical composition comprises a lipid or lipophilic vehicle.

Exemplary lipid or lipophilic vehicles comprise mineral oil; light mineral oil; natural oils (e.g., vegetable, corn, canola, sunflower, soybean, olive, coconut, cocoa, peanut, almond, cottonseed, persic, sesame, squalane, castor, cod liver) hydrogenated vegetable oil; partially hydrogenated oils; beeswax; polyethoxylated beeswax; paraffin; normal waxes; medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, or stearyl alcohol, inter alia, or combinations thereof.

In another embodiment described herein, the pharmaceutical composition comprises a solvent or solubility enhancing agent. Exemplary solvents or solubility enhancing agents useful for the matrix fills described herein include Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, propylene glycol, or combinations thereof.

In another embodiment described herein, the pharmaceutical composition comprises a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "*Physical Pharmacy: Physical Chemical Principles in the Pharmaceutical Sciences*," Fourth Edition, pp. 371-373, A. Martin, Ed., Lippincott Williams & Wilkins, Philadelphia (1993), which is incorporated by reference herein for such teachings.

In another embodiment described herein, the pharmaceutical composition comprises an emulsifying or solubilizing agents such as acacia, cholesterol, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, or combinations thereof.

In one embodiment described herein, the oral pharmaceutical compositions comprise an enteric soft capsule comprising one or more active pharmaceutical ingredient in the matrix. As used herein, the capsule "matrix" comprises a composition that occupies the capsule lumen and is encapsulated by the capsule shell. In one embodiment described herein, the enteric soft capsule comprises a gastric resistant or enteric shell and a matrix fill of a pharmaceutical composition that is liquid, semi-solid, or solid. In one aspect, the matrix fill comprises one or more active pharmaceutical ingredients. In another aspect, the matrix fill can be formulated to prevent interaction with the soft capsule shell components and release the active pharmaceutical ingredient at a specified rate. In another aspect, the matrix fill can comprise pharmaceutically acceptable vehicles, excipients, colors, or flavorings.

In one embodiment descried herein, the enteric soft capsule comprises a matrix fill comprising an active pharmaceutical ingredient comprising at least one or more fatty acids. In one aspect, the matrix fill comprises a pharmaceutical composition comprising one or more PUFAs.

In one embodiment, the oral pharmaceutical composition described herein comprises a matrix fill comprising the composition of Table 1, including all possible iterations of the specified ranges that provide 100% for the total weight percentage.

TABLE 1

Exemplary Fatty Acid (FA) Oil Matrix Fills

| Component | Percent weight (%) |
|---|---|
| Omega-3 FAs | 35-99 |
| Omega-6 FAs | ≤35 |
| EPA | 10-99 |
| DHA | 0.01-75 |
| DPA | 1-15 |
| EPA and DHA | 40-99 |
| EPA, DHA, and DPA | 40-99 |
| Arachidonic acid | ≤15 |
| Other unsaturated FAs | ≤15 |
| Saturated FAs | ≤3 |
| Antioxidants | 0.01-5 |
| Fat-soluble Vitamins | 0.001-5 |

In one embodiment, the pharmaceutical composition comprises a composition of omega-3 fatty acids comprising at least about 35% to at least about 50% by weight of all fatty acids in the pharmaceutical composition including all iterations of integers within the specified range. In one aspect, pharmaceutical composition comprises a composition of omega-3 fatty acids comprising at least about 35% by weight of all fatty acids in pharmaceutical composition. In another aspect, the pharmaceutical composition comprises a composition of omega-3 fatty acids comprising at least about 40% by weight of all fatty acids in the pharmaceutical composition. In another aspect, the pharmaceutical composition comprises a composition of omega-3 fatty acids comprising at least about 45% by weight of all fatty acids in the pharmaceutical composition. In another aspect, the pharmaceutical composition comprises a composition of omega-3 fatty acids comprising at least about 50% by weight of all fatty acids in the pharmaceutical composition. In another aspect, the omega-3 fatty acids may be a fatty acid, ester, re-esterified triglyceride, or salt thereof.

In another embodiment, the pharmaceutical composition comprises a composition of omega-3 fatty acids comprising of at least about 50% to at least about 85% by weight of all fatty acids in the pharmaceutical composition including all iterations of integers within the specified range. In one aspect, the pharmaceutical composition comprises a composition of omega-3 fatty acids comprising at least about 50% by weight of all fatty acids in the pharmaceutical composition. In another aspect, the pharmaceutical composition comprises a composition of omega-3 fatty acids comprising at least about 60% by weight of all fatty acids in the pharmaceutical composition. In another aspect, the pharmaceutical composition comprises a composition of omega-3 fatty acids comprising at least about 70% by weight of all fatty acids in the pharmaceutical composition. In another aspect, the pharmaceutical composition comprises a composition of omega-3 fatty acids comprising at least about 80% by weight of all fatty acids in the pharmaceutical composition. In another aspect, the omega-3 fatty acids may be a fatty acid, ester, re-esterified triglyceride, or salt thereof.

In another embodiment, the pharmaceutical composition comprises a composition of omega-3 fatty acids comprising of at least about 85% to at least about 99% by weight of all fatty acids in the pharmaceutical composition including all iterations of integers within the specified range. In one aspect, the pharmaceutical composition comprises a composition of omega-3 fatty acids comprising at least about 85% by weight of all fatty acids in the pharmaceutical composition. In another aspect, the pharmaceutical composition comprises a composition of omega-3 fatty acids comprising at least about 90% by weight of all fatty acids in the pharmaceutical composition. In another aspect, the pharmaceutical composition comprises a composition of omega-3 fatty acids comprising at least about 95% by weight of all fatty acids in the pharmaceutical composition. In another aspect, the pharmaceutical composition comprises a composition of omega-3 fatty acids comprising at least about 99% by weight of all fatty acids in the pharmaceutical composition. In another aspect, the omega-3 fatty acids may be a fatty acid, ester, re-esterified triglyceride, or salt thereof.

In one embodiment, the pharmaceutical composition comprises omega-3 fatty acids (e.g., EPA, DHA, or DPA, or a combination thereof) described herein in an amount of about 50 mg to about 5000 mg, about 75 mg to about 2500 mg, or about 100 mg to about 1000 mg including all iterations of integers within the specified ranges. In another embodiment, the pharmaceutical composition comprises the omega-3 (e.g., EPA, DHA, or DPA, or a combination thereof) fatty acids described herein in an amount of, for example, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 4000 mg, about 4025 mg, about 4050 mg, about 4075 mg, about 4100 mg, 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, or about 5000 mg. In another aspect, the omega-3 fatty acids may be a free fatty acid, ester, re-esterified triglyceride, or salt thereof.

In one embodiment, the pharmaceutical composition comprises omega-6 fatty acids in an amount not more than about 20% to not more than about 1% by weight of all fatty acids in the pharmaceutical composition including all iterations of integers within the specified range. In one embodiment, the pharmaceutical composition comprises omega-6 fatty acids in an amount not more than about 15% by weight of all fatty acids in the pharmaceutical composition. In one aspect, the pharmaceutical composition comprises omega-6 fatty acids in an amount not more than about 10% by weight of all fatty acids in the pharmaceutical composition. In one aspect, the pharmaceutical composition comprises omega-6 fatty acids in an amount not more than about 7% by weight of all fatty acids in the pharmaceutical composition. In one aspect, the pharmaceutical composition comprises omega-6 fatty acids in an amount not more than about 3% by weight of all fatty acids in the pharmaceutical composition. In one aspect, the pharmaceutical composition comprises omega-6 fatty acids in an amount not more than about 1% by weight of all fatty acids in the pharmaceutical composition. In one aspect, the pharmaceutical composition comprises essentially no omega-6 fatty acids.

In one embodiment, the pharmaceutical composition comprises EPA. In another embodiment, the pharmaceutical composition comprises EPA in an amount of about 10% to about 70% by weight of all fatty acids in the pharmaceutical composition including all iterations of integers within the specified range. In another aspect, the pharmaceutical composition comprises EPA in an amount of about 20% by weight of all fatty acids in the pharmaceutical composition. In another aspect, the pharmaceutical composition comprises EPA in an amount of about 25% by weight of all fatty acids in the pharmaceutical composition. In another aspect, the pharmaceutical composition comprises EPA in an amount of about 30% by weight of all fatty acids in the pharmaceutical composition. In another aspect, the pharmaceutical composition comprises EPA in an amount of about 35% by weight of all fatty acids in the pharmaceutical composition. In another aspect, the pharmaceutical composition comprises EPA in an amount of about 40% by weight of all fatty acids in the pharmaceutical composition. In another aspect, the pharmaceutical composition comprises EPA in an amount of about 45% by weight of all fatty acids in the pharmaceutical composition. In another aspect, the pharmaceutical composition comprises EPA in an amount of about 50% by weight of all fatty acids in the pharmaceutical composition. In another aspect, the pharmaceutical composition comprises EPA in an amount of about 55% by weight of all fatty acids in the pharmaceutical composition. In another aspect, the pharmaceutical composition comprises EPA in an amount of about 60% by weight of all fatty acids in the pharmaceutical composition. In another aspect, the pharmaceutical composition comprises EPA in an amount of about 65% by weight of all fatty acids in the pharmaceutical composition. In another aspect, the pharmaceutical composition comprises EPA in an amount of about 70% by weight of all fatty acids in the pharmaceutical composition. In another aspect, the pharmaceutical composition comprises EPA in an amount of about 75% by weight of all fatty acids in the pharmaceutical composition. In another aspect, the pharmaceutical composition comprises EPA in an amount of about 80% by weight of all fatty acids in the pharmaceutical composition. In another aspect, the pharmaceutical composition comprises EPA in an amount of about 85% by weight of all fatty acids in the pharmaceutical composition. In another aspect, the pharmaceutical composition comprises EPA in an amount of about 90% by weight of all fatty acids in the pharmaceutical composition. In another aspect, the pharmaceutical composition comprises EPA in an amount of about 95% by weight of all fatty acids in the pharmaceutical composition. In another aspect, the EPA may be a free fatty acid, ester, re-esterified triglyceride, or salt thereof.

In another embodiment, the pharmaceutical composition comprises EPA in an amount of about 70% to about 99% by weight of all fatty acids in the pharmaceutical composition including all iterations of integers within the specified range. In one aspect, the pharmaceutical composition comprises EPA in an amount of about 75% by weight of all fatty acids in the pharmaceutical composition. In another aspect, the pharmaceutical composition comprises EPA in an amount of about 80% by weight of all fatty acids in the pharmaceutical composition. In another aspect, the pharmaceutical composition comprises EPA in an amount of about 85% by weight of all fatty acids in the pharmaceutical composition. In another aspect, the pharmaceutical composition comprises EPA in an amount of about 90% by weight of all fatty acids in the pharmaceutical composition. In another aspect, the pharmaceutical composition comprises EPA in an amount of about 95% by weight of all fatty acids in the pharmaceutical composition. In another aspect, the pharmaceutical composition comprises EPA in an amount of about 99% by weight of all fatty acids in the pharmaceutical composition. In another aspect, the EPA may be a free fatty acid, ester, re-esterified triglyceride, or salt thereof.

In one embodiment, the pharmaceutical composition comprises EPA with substantially no DHA (e.g., less than about 5% DHA). In one aspect, the EPA may be a free fatty acid, ester, re-esterified triglyceride, or salt thereof.

In one embodiment, the pharmaceutical composition comprises DHA. In another embodiment, the pharmaceutical composition comprises DHA in an amount of about 10% to about 75% by weight of all fatty acids in the pharmaceutical composition including all iterations of integers within the specified range. In another embodiment, the pharmaceutical composition comprises DHA in an amount of about 10% to about 50% by weight of all fatty acids in the pharmaceutical composition including all iterations of integers within the specified range. In one aspect, the pharmaceutical composition comprises DHA in an amount of about 10% by weight of all fatty acids in the pharmaceutical composition. In another aspect, the pharmaceutical composition comprises DHA in an amount of about 15% by weight of all fatty acids in the pharmaceutical composition. In another aspect, the pharmaceutical composition comprises DHA in an amount of about 20% by weight of all fatty acids in the pharmaceutical composition. In another aspect, the pharmaceutical composition comprises DHA in an amount of about 25% by weight of all fatty acids in the pharmaceutical composition. In another aspect, the pharmaceutical composition comprises DHA in an amount of about 30% by weight of all fatty acids in the pharmaceutical composition. In another aspect, the pharmaceutical composition comprises DHA in an amount of about 35% by weight of all fatty acids in the pharmaceutical composition. In another aspect, the pharmaceutical composition comprises DHA in an amount of about 40% by weight of all fatty acids in the pharmaceutical composition. In another aspect, the pharmaceutical composition comprises DHA in an amount of about 45% by weight of all fatty acids in the pharmaceutical composition. In another aspect, the pharmaceutical composition comprises DHA in an amount of about 55% by weight of all fatty acids in the pharmaceutical composition. In another aspect, the pharmaceutical composition comprises DHA in an amount of about 60% by weight of all fatty acids in the pharmaceutical composition. In another aspect, the pharmaceutical composition comprises DHA in an amount of about 65% by weight of all fatty acids in the pharmaceutical composition. In another aspect, the pharmaceutical composition comprises DHA in an amount of about 70% by weight of all fatty acids in the pharmaceutical composition. In another aspect, the pharmaceutical composition comprises DHA in an amount of about 76% by weight of all fatty acids in the pharmaceutical composition. In another aspect, the DHA may be a free fatty acid, ester, re-esterified triglyceride, or salt thereof.

In one embodiment, the pharmaceutical composition comprises DPA. In another embodiment, the pharmaceutical composition comprises DPA in an amount of about 1% to about 15% by weight of all fatty acids in the pharmaceutical composition including all iterations of integers within the specified range. In one aspect, the pharmaceutical composition comprises DPA in an amount of about 1% by weight of all fatty acids in the pharmaceutical composition. In another aspect, the pharmaceutical composition comprises DPA in an amount of about 3% by weight of all fatty acids in the pharmaceutical composition. In another aspect, the pharmaceutical composition comprises DPA in an amount of about 5% by weight of all fatty acids in the pharmaceutical composition. In another aspect, the pharmaceutical composition comprises DPA in an amount of about 7% by weight of all fatty acids in the pharmaceutical composition. In another aspect, the pharmaceutical composition comprises DPA in an amount of about 10% by weight of all fatty acids in the pharmaceutical composition. In another aspect, the pharmaceutical composition comprises DPA in an amount of about 13% by weight of all fatty acids in the pharmaceutical composition. In another aspect, the DPA may be a free fatty acid, ester, re-esterified triglyceride, or salt thereof.

In one embodiment, the pharmaceutical composition comprises EPA and DHA. In another embodiment, the pharmaceutical composition comprises EPA and DHA in an amount of about 45% to about 99% by weight of all fatty acids in the pharmaceutical composition including all iterations of integers within the specified range. In another embodiment, the pharmaceutical composition comprises EPA and DHA in an amount of about 60% to about 99% by weight of all fatty acids in the pharmaceutical composition including all iterations of integers within the specified range. In one aspect, the pharmaceutical composition comprises EPA and DHA in an amount of about 60% by weight of all fatty acids in the pharmaceutical composition. In one aspect, the pharmaceutical composition comprises EPA and DHA in an amount of about 75% by weight of all fatty acids in the pharmaceutical composition. In another aspect, the pharmaceutical composition comprises EPA and DHA in an amount of about 85% by weight of all fatty acids in the pharmaceutical composition. In another aspect, the pharmaceutical composition comprises EPA and DHA in an amount of about 90% by weight of all fatty acids in the pharmaceutical composition. In another aspect, the pharmaceutical composition comprises EPA and DHA in an amount of about 95% by weight of all fatty acids in the pharmaceutical composition. In another aspect, the pharmaceutical composition comprises EPA and DHA in an amount of about 99% by weight of all fatty acids in the pharmaceutical composition. In another aspect, the EPA and DHA may be a free fatty acid, ester, re-esterified triglyceride, or salt thereof.

In one embodiment, the pharmaceutical composition comprises EPA, DHA, and DPA. In another embodiment, the pharmaceutical composition comprises EPA, DHA, and DPA in an amount of about 60% to about 99% by weight of all fatty acids in the pharmaceutical composition including all iterations of integers within the specified range. In another embodiment, the pharmaceutical composition comprises EPA, DHA, and DPA in an amount of about 85% to about 99% by weight of all fatty acids in the pharmaceutical composition including all iterations of integers within the specified range. In one aspect, the pharmaceutical composition comprises EPA, DHA, and DPA in an amount of about 85% by weight of all fatty acids in the pharmaceutical composition. In another aspect, the pharmaceutical composition comprises EPA, DHA, and DPA in an amount of about 90% by weight of all fatty acids in the pharmaceutical composition. In another aspect, the pharmaceutical composition comprises EPA, DHA, and DPA in an amount of about 95% by weight of all fatty acids in the pharmaceutical composition. In another aspect, the pharmaceutical composition comprises EPA, DHA, and DPA in an amount of about 99% by weight of all fatty acids in the pharmaceutical composition. In another aspect, the EPA, DHA, and DPA may be a free fatty acid, ester, re-esterified triglyceride, or salt thereof.

In one embodiment the pharmaceutical composition comprises a mixture of EPA and DHA with one or more fat soluble vitamins. In one aspect, EPA comprises about 10% to about 70% by weight of the pharmaceutical composition, including each integer within the specified range. In another aspect, DHA comprises about 10% to about 70% by weight of the pharmaceutical composition, including each integer within the specified range. In another aspect, at least another fat soluble vitamin comprises about 0.005% to about 5% by weight of the pharmaceutical composition, including each integer within the specified range. In another aspect the pharmaceutical composition comprises about 50% EPA and about 20% DHA, and at least another fat soluble vitamin. In another aspect, the pharmaceutical composition comprises at least about 60% EPA and at least about 25% DHA, and at least another fat soluble vitamin. In another aspect, the composition comprises at least about 45% EPA and at least about 20% DHA, and at least another fat soluble vitamin. In another aspect, the composition comprises at least about 46% EPA, at least about 18% DHA, and at least another fat soluble vitamin. In another aspect, the composition comprises at least about 30% EPA, at least about 20% DHA, and at least another fat soluble vitamin. In another aspect, a mixture of EPA and DHA comprising at least about 45% EPA and at least about 18% DHA can be combined in a 99.9:0.1 ratio with cholecalciferol (Vitamin D3) to form a pharmaceutical or nutritional composition; other fat soluble vitamins described herein and known in the art can be added at similar weight percentages. In another aspect, the EPA and DHA may be a free fatty acid, ester, re-esterified triglyceride, or salt thereof.

In one embodiment, the ratio of EPA to DHA in the pharmaceutical composition is about 1:3 to about 9:1, including all iterations of ratios within the specified range. In one aspect, the ratio of EPA to DHA in the pharmaceutical composition is about 1:3. In another aspect, the ratio of EPA to DHA in the pharmaceutical composition is about 1:2. In another aspect, the ratio of EPA to DHA in the pharmaceutical composition is about 1:1. In another aspect, the ratio of EPA to DHA in the pharmaceutical composition is about 2:1. In another aspect, the ratio of EPA to DHA in the pharmaceutical composition is about 3:1. In another aspect, the ratio of EPA to DHA in the pharmaceutical composition is about 4:1. In another aspect, the ratio of EPA to DHA in the pharmaceutical composition is about 5:1. In another aspect, the ratio of EPA to DHA in the pharmaceutical composition is about 6:1. In another aspect, the ratio of EPA to DHA in the pharmaceutical composition is about 7:1. In another aspect, the ratio of EPA to DHA in the pharmaceutical composition is about 8:1. In another aspect, the ratio of EPA to DHA in the pharmaceutical composition is about 9:1. In another aspect, the ratio of EPA to DHA in the pharmaceutical composition is about 9.5:1.

In another embodiment, the pharmaceutical composition comprises less than about 30%, less than about 20%, less than about 10%, less than about 9%, less than about 8%, less than about 7%, less than about 6%, less than about 5%, less than about 4%, less than about 3%, less than about 2%, less than about 1%, less than about 0.5% or less than about 0.25%, by weight of the total composition or by weight of the total fatty acid content, of any unsaturated fatty acid other than EPA, DHA, or DPA. Illustrative examples of any unsaturated fatty acid other than EPA, DHA, or DPA comprise hexadecatrienoic acid (HTA; all-cis 7,10,13-hexadecatrienoic acid), alpha-linolenic acid (ALA; all-cis-9,12,15-octadecatrienoic acid), stearidonic acid (SDA; all-cis-6,9,12,15,-octadecatetraenoic acid), eicosatrienoic acid (ETE; all-cis-11,14,17-eicosatrienoic acid), eicosatetraenoic acid (ETA; all-cis-8,11,14,17-eicosatetraenoic acid), heneicosapentaenoic acid (HPA; all-cis-6,9,12,15,18-heneicosapentaenoic acid), tetracosapentaenoic acid (all-cis-9,12,15,18,21-tetracosapentaenoic acid), tetracosahexaenoic acid (nisinic acid; all-cis-6,9,12,15,18,21-tetracosahexaenoic acid), linoleic acid (LA; all-cis-9,12-octadecadienoic acid), gamma-linolenic acid (GLA; all-cis-6,9,12-octadecatrienoic acid), calendic acid (8E,10E,12Z-octadecatrienoic acid), eicosadienoic acid (all-cis-11,14-eicosadienoic acid), dihomo-gamma linolenic acid (DGLA; all-cis-8,11,14-eicosatrienoic acid), arachidonic acid (AA; all-cis-5,8,11,14-eicosatetraenoic acid), docosadienoic acid (all-cis-13,16-docosadienoic acid), Adrenic acid (all-cis-7,10,13,16-docosatetraenoic acid), docosapentaenoic acid (osbond acid; all-cis-4,7,10,13,16-docosapentaenoic acid), tetracosatetraenoic acid (all-cis-9,12,15,18-tetracosatetraenoic acid), tetracosapentaenoic acid (all-cis-6,9,12,15,18-tetracosapentaenoic acid) and free acids, ethyl esters, or other esters or salts thereof.

In one embodiment, the pharmaceutical composition comprises about 250 mg to about 5000 mg of highly pure EPA ethyl ester (e.g., at least about 95% EPA). In another embodiment, the pharmaceutical composition comprises about 250 mg to about 2500 mg of highly pure EPA ethyl ester (e.g., at least about 95% EPA). In one aspect, the pharmaceutical composition comprises about 250 mg of highly pure EPA ethyl ester (e.g., at least about 95% EPA). In another aspect, the pharmaceutical composition comprises about 500 mg of highly pure EPA ethyl ester (e.g., at least about 95% EPA). In another aspect, the pharmaceutical composition comprises about 1000 mg of highly pure EPA ethyl ester (e.g., at least about 95% EPA). In another aspect, the pharmaceutical composition comprises about 2000 mg of highly pure EPA ethyl ester (e.g., at least about 95% EPA). In another aspect, the pharmaceutical composition comprises about 3000 mg of highly pure EPA ethyl ester (e.g., at least about 95% EPA). In another aspect, the pharmaceutical composition comprises about 4000 mg of highly pure EPA ethyl ester (e.g., at least about 95% EPA). In another aspect, the pharmaceutical composition comprises about 5000 mg of highly pure EPA ethyl ester (e.g., at least about 95% EPA). See U.S. Patent Application Publication No. US 2010/0278879, which is incorporated by reference herein for its specific teachings of pure EPA ethyl esters.

In one embodiment, the pharmaceutical composition comprises at least about 250 mg to about 5000 mg of EPA, DHA, and DPA in an amount of about 50% to about 60% EPA, 15% to about 25% DHA, and about 1% to about 8% DPA. In another embodiment, the pharmaceutical composition comprises at least about 250 mg to about 2500 mg of EPA, DHA, and DPA in an amount of about 50% to about 60% EPA, 15% to about 25% DHA, and about 1% to about 8% DPA. In one aspect, the pharmaceutical composition comprises at least about 250 mg of EPA, DHA, and DPA in an amount of about 50% to about 60% EPA, 15% to about 25% DHA, and about 1% to about 8% DPA. In another aspect, the pharmaceutical composition comprises at least about 500 mg of EPA, DHA, and DPA in an amount of about 50% to about 60% EPA, 15% to about 25% DHA, and about 1% to about 8% DPA. In another aspect, the pharmaceutical composition comprises at least about 1000 mg of EPA, DHA, and DPA in an amount of about 50% to about 60% EPA, 15% to about 25% DHA, and about 1% to about 8% DPA. In another aspect, the pharmaceutical composition comprises at least about 2000 mg of EPA, DHA, and DPA in an amount of about 50% to about 60% EPA, 15% to about 25% DHA, and about 1% to about 8% DPA. In another aspect, the pharmaceutical composition comprises at least about 3000 mg of EPA, DHA, and DPA in an amount of about 50% to about 60% EPA, 15% to about 25% DHA, and about 1% to about 8% DPA. In another aspect, the pharmaceutical composition comprises at least about 4000 mg of EPA, DHA, and DPA in an amount of about 50% to about 60% EPA, 15% to about 25% DHA, and about 1% to about 8% DPA. In another aspect, the pharmaceutical composition comprises at least about 5000 mg of EPA, DHA, and DPA in an amount of about 50% to about 60% EPA, 15% to about 25% DHA, and about 1% to about 8% DPA. In another aspect, EPA, DHA, and DPA are free fatty acids. See U.S. Patent Application Publication No. US 2013/0177643, which is incorporated by reference herein for its specific teachings of DPA, EPA, and DHA compositions In one embodiment, the pharmaceutical composition comprises about 250 mg to about 5000 mg of EPA and DHA in an amount of about 47% EPA and 38% DHA.

In another embodiment, the pharmaceutical composition comprises about 250 mg to about 2500 mg of EPA and DHA in an amount of about 47% EPA and 38% DHA. In one aspect, the pharmaceutical composition comprises about 250 mg of EPA and DHA in an amount of about 47% EPA and 38% DHA. In one aspect, the pharmaceutical composition comprises about 500 mg of EPA and DHA in an amount of about 47% EPA and 38% DHA. In one aspect, the pharmaceutical composition comprises about 1000 mg of EPA and DHA in an amount of about 47% EPA and 38% DHA. In one aspect, the pharmaceutical composition comprises about 2000 mg of EPA and DHA in an amount of about 47% EPA and 38% DHA. In one aspect, the pharmaceutical composition comprises about 3000 mg of EPA and DHA in an amount of about 47% EPA and 38% DHA. In one aspect, the pharmaceutical composition comprises about 4000 mg of EPA and DHA in an amount of about 47% EPA and 38% DHA. In one aspect, the pharmaceutical composition comprises about 5000 mg of EPA and DHA in an amount of about 47% EPA and 38% DHA. In another aspect, the EPA and DHA may be a free fatty acid, ester, re-esterified triglyceride, or salt thereof. See U.S. Pat. No. 5,656,667 is incorporated by reference herein for its specific teachings of EPA and DHA compositions.

In one embodiment, the pharmaceutical composition comprises about 410 mg of the fish oil described herein. In one aspect, the pharmaceutical composition comprises about 250 mg of omega-3 fatty acids. In another aspect, the pharmaceutical composition comprises about 250 mg of EPA and DHA. In another aspect, the pharmaceutical composition comprises about 180 mg of EPA and about 70 mg of DHA (i.e., about 44% EPA and about 17% DHA). In another aspect, the EPA is EPA ethyl ester. In another aspect, the DHA is DHA ethyl ester. In another aspect, the pharmaceutical composition comprises one or more antioxidants or fat-soluble vitamins.

In one embodiment, the pharmaceutical composition comprises about 820 mg of the fish oil described herein. In one aspect, the pharmaceutical composition comprises about 500 mg of omega-3 fatty acids. In one aspect, the pharmaceutical composition comprises about 500 mg of EPA and DHA. In another aspect, the pharmaceutical composition comprises about 360 mg of EPA and 140 mg of DHA (i.e., about 44% EPA and about 17% DHA). In another aspect, the EPA is EPA ethyl ester. In another aspect, the DHA is DHA ethyl ester. In another aspect, the pharmaceutical composition comprises one or more antioxidants or fat-soluble vitamins.

In one embodiment, the pharmaceutical composition comprises about 600 mg of the fish oil described herein. In one aspect, the pharmaceutical composition comprises about 300 mg of omega-3 fatty acids. In one aspect, the pharmaceutical composition comprises about 270 mg of EPA and DHA. In another aspect, the pharmaceutical composition comprises about 160 mg of EPA and 110 mg of DHA (i.e., about 27% EPA and about 18% DHA). In another aspect, the EPA is EPA ethyl ester. In another aspect, the DHA is DHA ethyl ester. In another aspect, the pharmaceutical composition comprises one or more antioxidants or fat-soluble vitamins.

In one embodiment, the pharmaceutical composition comprises about 1200 mg of the fish oil described herein. In one aspect, the pharmaceutical composition comprises about 600 mg of Omega-3 fatty acids. In one aspect, the pharmaceutical composition comprises about 540 mg of EPA and DHA. In another aspect, the pharmaceutical composition comprises about 325 mg of EPA and 215 mg of DHA (i.e., about 27% EPA and about 18% DHA). In another aspect, the EPA is EPA ethyl ester. In another aspect, the DHA is DHA ethyl ester. In another aspect, the pharmaceutical composition comprises one or more antioxidants or fat-soluble vitamins.

In one embodiment, the pharmaceutical composition comprises about 1400 mg of the fish oil described herein. In one aspect, the pharmaceutical composition comprises about 900 mg of omega-3 fatty acids. In one aspect, the pharmaceutical composition comprises about 650 mg of EPA and DHA. In another aspect, the pharmaceutical composition comprises about 647 mg of EPA and 253 mg of DHA (i.e., about 46% EPA and about 18% DHA). In another aspect, the EPA is EPA ethyl ester. In another aspect, the DHA is DHA ethyl ester. In another aspect, the pharmaceutical composition comprises one or more antioxidants or fat-soluble vitamins.

In one embodiment, one or more antioxidants can be present in the pharmaceutical compositions described herein. Suitable antioxidants comprise tocopherols (e.g., alpha tocopherol, beta tocopherol, gamma tocopherol, or delta tocopherol), butylated hydroxytoluene (BHT), butylated hydroxyanisole (BHA), lecithin, citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or any mixture thereof. In one aspect, the one or more antioxidants are present in the fatty acid fills described herein in an amount of about 0.01% to about 2%, by weight of the fatty acids.

In one embodiment described herein, the pharmaceutical composition contains not more than about 20 ppm, about 15 ppm or about 10 ppm of heavy metals (e.g., Pb, Hg, Bi, As, Sb, Sn, Cd, Ag, Cu, or Mo; e.g., USP test 231). In another embodiment described herein, the pharmaceutical composition described herein contains not more than 5 ppm, 4 ppm, 3 ppm, or 2 ppm of arsenic. In another embodiment described herein, the pharmaceutical composition described herein has a peroxide value not more than about 10 meq/kg, 9 meq/kg, 8 meq/kg, 7 meq/kg, 6 meq/kg, 5 meq/kg, about 4 meq/kg, about 3 meq/kg, or about 2 meq/kg. U.S. Patent Application Publication No. US 2010/0278879, which is incorporated by reference herein for its specific teachings of heavy metal levels and peroxide values.

In another embodiment described herein, the pharmaceutical composition described herein comprising the fatty acids described herein having a baseline or first peroxide value not more than about 10 meq/kg, 9 meq/kg, 8 meq/kg, 7 meq/kg, 6 meq/kg, 5 meq/kg, about 4 meq/kg, about 3 meq/kg, or about 2 meq/kg, wherein upon storage of the said pharmaceutical composition at about 30° C. and about 65% relative humidity for a period about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months or about 24 months, said pharmaceutical composition has a second peroxide value not greater than about 25 meq/kg, about 24 meq/kg, about 23 meq/kg, about 22 meq/kg, about 21 meq/kg, about 20 meq/kg, about 19 meq/kg, about 18 meq/kg, about 17 meq/kg, about 16 meq/kg, about 15 meq/kg, about 14 meq/kg, about 13 meq/kg, about 12 meq/k meq/kg g, about 11 meq/kg, about 10 meq/kg, about 9 meq/kg, about 8 meq/kg, about 7 meq/kg, about 6 meq/kg, about 5 meq/kg, about 4 meq/kg, about 3 meq/kg or about 2 meq/kg.

The "baseline peroxide value" and "second peroxide values" can be measured in any suitable manner, for example by using any one of U.S. Pharmacopeia, Pharmacopeia Europe, or Japanese Pharmacopeia compendial methods. Typically, a plurality of encapsulated EPA compositions is provided, each composition containing EPA having been encapsulated at substantially the same time. A first sampling of one or more capsules from the plurality is provided, the capsules are opened, and peroxide value of the EPA is measured substantially immediately thereafter, providing an average baseline peroxide value. At substantially the same time, a second sampling of one or more capsules from the plurality is provided and is placed under desired storage conditions for a desired time period. At the end of the desired time period, the capsules are opened and peroxide value of the EPA is measured substantially immediately thereafter, providing an average second peroxide value. The baseline and second peroxide values can then be compared. In one embodiment, the "baseline peroxide value" and "second peroxide value" are determined using a plurality of encapsulated EPA dosage units wherein each dosage unit was encapsulated (e.g., the EPA is filled and sealed into capsules) within a same 60 day period, same 30 day period, a same 20 day period, a same 10 day period, a same 5 day period or a same 1 day period.

One embodiment described herein, is a pharmaceutical composition comprising an enteric soft capsule comprising one or more film forming polymers, one or more enteric polymers, one or more plasticizers, one or more alkali neutralizing agents, one or more solvents, and optionally one or more biomaterials, colorings, gelling agents, flavorings, or other conventionally accepted pharmaceutical excipients or additives. In one aspect, enteric soft capsule composition described herein further comprises an active pharmaceutical ingredient in a matrix fill.

The enteric soft capsules described herein can be used for oral delivery of active pharmaceutical ingredients, pharmaceutical agents, nutraceuticals, or nutritionals that are irritating to the stomach, that are sensitive to the acidity of the stomach, or that have unpleasant tastes or odors. The enteric soft capsules described herein do not dissolve in the gastric environment (pH ca. 1.2), but readily dissolve in the intestinal environment (pH ca. 6.8).

One embodiment described herein is an all-natural enteric soft capsule composition comprising a gelatin composition ionically bonded with anionic enteric polymers. The enteric soft capsule shell can comprise one or more types of gelatin, one or more anionic enteric polymers, one or more plasticizers, one or more solvents, and optionally colorings, gelling agents, flavorings, or other conventionally accepted pharmaceutical excipients or additives.

Enteric soft capsules are described generally in International Patent Application Publication Nos. WO 2004/030658 and WO 2007/075475 and U.S. Patent Application Publication Nos. US 2006/0165778 and US 2010/0158958, each of which is incorporated by reference herein for such teachings.

Useful film forming polymers can be a natural, synthetic or semi-synthetic film forming polymer. Examples of film-former polymers that are of a natural origin, include but are not limited to gelatin and carrageenan. Suitable synthetic and semi-synthetic film forming polymers include, for example, hydroxypropyl methyl cellulose, methyl cellulose, hydroxypropyl methyl cellulose acetate succinate, hydroxypropyl methyl cellulose phthalate, and cellulose acetate phthalate.

Gelatin compositions that are useful for creating enteric soft capsules described herein can be classified as either Type A or Type B gelatin. Examples of gelatin compositions that are useful for creating enteric soft capsule shells as described herein comprise acid bone gelatin, pig skin gelatin, chicken skin gelatin, fish gelatin, acid hide gelatin, gelatin hydrolysate, lime bone gelatin or combinations thereof. Type A gelatin is derived from the acid hydrolysis of collagen (e.g., acid bone gelatin or pig skin gelatin), while Type B gelatin (e.g., lime bone gelatin) is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid processed gelatins form stronger gels than lime-processed gelatins of the same average molecular weight. In addition, at neutral pH values, Type A gelatins (acid processed gelatins) are typically net cationic and Type B gelatins (alkali processed gelatins) are typically net anionic. The strength of said gelatin compositions are often defined by their Bloom strength or grade in the range of about 30 Bloom to about 400 Bloom. In one embodiment, the gelatin Bloom strength is from about 50 to about 200, including each integer in the specified range. In one aspect, the Bloom strength of the gelatin is about 100 Bloom. In one aspect, the Bloom strength of the gelatin is about 125 Bloom. In one aspect, the Bloom strength of the gelatin is about 150 Bloom. In another aspect, the Bloom strength of the gelatin is about 175 Bloom. In another aspect, the Bloom strength of the gelatin is about 190 Bloom.

Examples of film-former polymers that are useful for creating non-animal/non-gelatin enteric soft capsules described herein are kappa carrageenan, iota carrageenan, lambda carrageenan, or combinations thereof.

Useful plasticizers as described herein comprise polyalcohols with 3 to 6 carbon atoms, glycerol, sorbitol, Sorbitol Special® (SPI Pharma), non-crystallizing sorbitol, Polysorb® sorbitol 85/70/00 (Roquette), corn syrup, polyethylene glycol, 1,2-propylene glycol, acetyl triethyl citrate, dibutyl phthalate, dibutyl sebacate, triacetine, polydextrose, maltodextrin, citric acid, citric acid esters, such as triethyl citrate, or combinations thereof. The weight ratios between the film forming polymer, the acid-insoluble enteric polymer, filler, and plasticizer are adjusted so that the gel mass is flowable and not too viscous, and can be made into enteric soft capsules. In one particular embodiment described herein, the plasticizer comprises at least one of glycerol, sorbitol, corn syrup, malatol, triethyl citrate, or mixtures or combinations thereof.

Examples of enteric, acid-insoluble polymers or enteric polymers are acrylic and methacrylate acid copolymers, cellulose acetate phthalate (CAP), cellulose acetate butyrate, hydroxypropylmethylcellulose phthalate (HPMCP), alginic acid salts such as sodium or potassium alginate, or shellac. Acrylic and methacrylate acid copolymers are anionic copolymers based on methacrylic acid and methyl methacrylate that are particularly stable and are preferred in one embodiment. Acrylic and methacrylate acid copolymers available under the trade name EUDRAGIT® (Evonik Industries AG, Essen, Germany) are provided as powder or aqueous dispersions, and in one aspect, can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; other poly(meth)acrylate polymers; or a mixture thereof. Acid-insoluble polymer specifications are detailed in the United States Pharmacopoeia and in various monographs.

In one embodiment described herein, the enteric polymer in the enteric soft capsule shell comprises poly(methacylic acid-co-methyl methacrylate) 1:1 (e.g., EUDRAGIT® L 100). In one embodiment described herein, the enteric polymer in the enteric soft capsule shell comprises poly (methacylic acid-co-ethyl acrylate) 1:1 (e.g., EUDRAGIT® L 100-55). In one embodiment described herein, the enteric polymer comprises poly(ethyl acrylate-co-methyl methacrylate) 2:1 (e.g., EUDRAGIT® NE 40 D). In another embodiment described herein, the enteric polymer comprises poly (methyl acrylate-co-methyl methacrylate-co-methacrylic acid) 7:3:1 (e.g., EUDRAGIT® FS 30 D). In another embodiment described herein the enteric polymer comprises a combination of poly(methacylic acid-co-ethyl acrylate) 1:1 and poly(methyl acrylate-co-methyl methacrylate-co-methacrylic acid) 7:3:1. In another embodiment, the enteric polymer comprises a combination of poly(methacylic acid-co-ethyl acrylate) 1:1 and poly(ethyl acrylate-co-methyl methacrylate) 2:1. In another embodiment, the enteric polymer comprises a combination of poly(methacylic acid-co-ethyl acrylate) 1:1, poly(ethyl acrylate-co-methyl methacrylate) 2:1, and poly(methyl acrylate-co-methyl methacrylate-co-methacrylic acid) 7:3:1.

In one embodiment, enteric soft capsule shells can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In another embodiment, the final pH does not exceed 8.5. The film forming polymer can then be combined with the plasticizer and solvent and then blended with the acid-insoluble gel to make a final homogeneous mixture. In one aspect, sodium hydroxide is a preferred alkali neutralizing agent.

In another embodiment described herein, an enteric soft capsule shell can be made by using an aqueous dispersion of the acid-insoluble polymer or polymers by adding alkaline materials such as ammonium, sodium, or potassium hydroxides, other alkalis, or a combination thereof that will cause the enteric acid-insoluble polymer to dissolve. The plasticizer-wetted, film forming polymer can then be mixed with the solution of the acid-insoluble polymer. In one embodiment described herein, enteric acid-insoluble polymers in the form of salts of the above-mentioned bases or alkalis can be dissolved directly in water and mixed with the plasticizer-wetted, film forming polymer. In another embodiment described herein, an aqueous dispersion of the acid-insoluble polymer or polymers can be used, which obviates the need for the addition of the aforementioned alkaline materials.

In another embodiment described herein, an enteric soft capsule shell can be made using natural enteric, acid-insoluble anionic polymer. In one aspect, the enteric acid-insoluble anionic polymer is an anionic polysaccharide. In another aspect, the anionic polysaccharide comprises polygalacturonic acid, carboxymethyl pullulan, carboxymethyl cellulose, hyaluronic acid, cellulose phthalate, cellulose succinate, alginate, sodium alginate, or pectin. In another aspect described herein, the anionic polysaccharide comprises pectin. Acid-insoluble specifications of enteric capsules are detailed in the United States Pharmacopoeia and in various monographs.

In one embodiment described herein, enteric soft capsules may optionally comprise fillers or bulking agents comprising hydroxypropyl starch phosphate, acacia, alginic acid, microcrystalline cellulose, carboxymethylcellulose, hydroxypropyl methylcellulose, methylcellulose, ethylcellulose, pregelatinized starch, potato starch, tapioca starch, rice starch, corn starch, wheat starch, pea starch, modified starches, pregelatinized starch, microcrystalline cellulose, hydroxypropyl methylcellulose, lactose, dextrates, dextrin, dextrose, maltodextrin, glucose, sucrose, powdered sugar, sucrose syrup, mannitol, gums like xanthan gum, *tragacantha*, guar gum, acacia gum, arabic gum, ferula gummosa boiss, gum olibanum, beilschmiedia seed gum, aegle marmelos gum, okra gum, *cassia roxburghii* seeds gum, kaolin, talc, bentonite, calcium phosphates, calcium carbonate, magnesium carbonate, magnesium oxide, calcium sulphate, hydrogenated sodium chloride, potassium chloride, combinations or mixtures thereof, and others known in the art. Other useful fillers are NLok®, (starch sodium octenyl succinate), Hi-Cap™, and Ultra Sperse® M.

In one embodiment, optional gelling agents can be added to the enteric soft capsules. The addition of gelling agents is optional and depends on the gelatin type (e.g., Type B gelatin), which may function to increase the overall strength of the capsule shell. Without being bound to any theory, it is believed that the cationic gelling agent promotes an ionic interaction between the gelatin composition and anionic enteric polymers described herein. Suitable gelling agents as described herein comprise mono or divalent cations, such as calcium, sodium, potassium, magnesium, or their salt forms comprising calcium sulfate, sodium chloride, potassium sulfate, sodium carbonate, lithium chloride, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

In one embodiment described herein, the enteric capsule shells can optionally, include one or more viscosity modifiers. Examples of suitable viscosity modifiers include guar gum, locust bean gum, xanthan gum, agar, and gellan gum. The viscosity modifier can be included in the capsule shell in an amount of greater than 0.01% by weight and less than 10% by weight of the dried capsule shell (e.g., less than 9%, less than 8%, less than 7%, less than 6%, less than 5%, less than 4%, less than 3%, less than 2%, less than 1%, or less than 0.5% by weight of the dried capsule shell).

The enteric capsule shell can be prepared as a transparent or translucent enteric capsule shell. In one embodiment, the enteric capsule shell can be semi-transparent, semi-opaque, or opaque. Optionally, the opaque enteric capsule shells are prepared using titanium dioxide, which can protect light sensitive active ingredients from degradation. The enteric capsule shells can further include a colorant to color the capsules. Examples of suitable colorants include FD&C and D&C dyes, iron oxides, and natural colorants. Optionally, the capsule can be imprinted or have a decorative coating. The enteric capsule shell can be prepared to have only one compartment (i.e., the enteric capsule shell does not contain multiple compartments).

Useful sealants that impart moisture protection to the capsule shell include but are not limited to a methacrylic acid copolymer, hydroxypropylmethylcellulose, or a proprietary sealant such as Kollicoat® Protect (BASF). In one embodiment described herein, the sealant is Kollicoat® Protect.

In one embodiment described herein, the enteric soft capsule has the composition of Table 2, including all possible iterations of the specified ranges that provide 100% for the total weight percentage, including or excluding the optional sealants, colorings, flavorings, or excipients.

TABLE 2

Enteric Soft Capsule Shell Composition

| Component | Exemplary Components | Composition Range (%) |
|---|---|---|
| Film forming polymer | Gelatin | 0.5-50 |
| Enteric-acid insoluble polymer | Anionic polysaccharide or acrylic and methacrylic acid copolymers | 0.25-20 |
| Plasticizer | Glycerol and/or Sorbitol and/or Triethyl citrate | 6-40 |
| Alkali neutralizing agent | NH$_4$OH (30%) or NaOH | 0.01-7 |
| Gelling agent | Calcium or Magnesium or Potassium | 0.01-1 |
| Filler (bulking agent) | Hydroxypropyl starch phosphate | 10-20 |
| Solvent | Water | 10-70 |
| Sealant (optional) | Kollicoat ® Protect | 1-5 |
| Opacifier (optional) | Titanium dioxide | 0.5-5 |
| Coloring (optional) | Various | 0.005-1 |
| Flavoring (optional) | Various | 0.005-2 |
| Excipients (optional) | Various | 1-5 |

In another embodiment described herein, the film forming polymer comprises gelatin. In one embodiment, the weight percentage of the total gelatin composition in the enteric soft gel composition comprises from about 10% to about 50% including all integers within the specified range. In another embodiment, the weight percentage of the gelatin composition in the gel mass comprises from about 13% to about 45% including all integers within the specified range. In another embodiment, the weight percentage of the gelatin composition in the gel mass comprises from about 28% to about 36%. In one aspect, the weight percentage of the gelatin composition in the gel mass is about 29%. In another aspect, the weight percentage of the gelatin composition in the gel mass is about 33%. In another aspect, the weight percentage of the gelatin composition in the gel mass is about 35%. In another aspect, the weight percentage of the gelatin composition in the gel mass is about 44%.

In another embodiment described herein, the weight percentage ratio range of Type A gelatin to Type B gelatin in the enteric soft gel composition comprises from about 2:1 to about 11:1, including all ratios within the specified range. In one aspect, the weight percentage ratio range of Type A gelatin to Type B gelatin in the gel mass is about 6:1. In another aspect, the ratio of Type A gelatin to Type B gelatin in the gel mass is about 3:1.

In another embodiment described herein, the weight percentage ratio of Type A gelatin to gelatin hydrolysate in the enteric soft gel composition comprises from about 10:1 to about 35:1, including all ratios within the specified range. In one aspect, the weight percentage ratio of Type A gelatin to gelatin hydrolysate in the gel mass is about 12:1, including all integers within the specified range. In another aspect, the ratio of Type A gelatin to gelatin hydrolysate in the gel mass is about 27:1.

In another embodiment described herein, the weight percentage of Type A gelatin in the enteric soft gel composition comprises from about 22% to about 38%, including all integers within the specified range. In another embodiment, the weight percentage of Type A gelatin in the gel mass comprises from about 28% to about 36%, including all integers within the specified range. In one aspect, the weight percentage of Type A gelatin in the gel mass is about 28%. In another aspect, the weight percentage of Type A gelatin in the gel mass is about 31%. In another aspect, the weight percentage of Type A gelatin in the gel mass is about 33%.

In another embodiment described herein, the weight percentage of Type B gelatin in the enteric soft gel composition comprises from about from 22% to about 38%, including all integers within the specified range. In another embodiment, the weight percentage of Type B gelatin in the gel mass comprises from about from 28% to about 36%, including all integers within the specified range. In one aspect, the weight percentage of Type B gelatin in the gel mass is about 28%. In another aspect, the weight percentage of Type B gelatin in the gel mass is about 31%. In another aspect, the weight percentage of Type A gelatin in the gel mass is about 33%. In another aspect, the weight percentage of Type A gelatin in the gel mass is about 36%.

In another embodiment described herein, the weight percentage of Type B gelatin in the enteric soft gel composition comprises from about 1% to about 10%, including all integers within the specified range. In another embodiment, the weight percentage of Type B gelatin in the gel mass comprises from about 1% to about 7%, including all integers within the specified range. In one aspect, the weight percentage of Type B gelatin in the gel mass is about 3%. In another aspect, the weight percentage of Type B gelatin in the gel mass is about 7%. In another aspect, the weight percentage of Type B gelatin in the gel mass is about 9%.

In one embodiment, described herein, the weight percentage of enteric acid insoluble polymer in the enteric soft gel composition comprises from about 2% to about 30% of the enteric soft shell capsule.

In one embodiment described herein, the enteric acid insoluble polymer comprises a natural polymer. In one aspect, the natural enteric acid insoluble polymer comprises an anionic polysaccharide. In one aspect, the anionic polysaccharide comprises pectin. In one aspect, the weight percentage of pectin in the enteric soft gel composition comprises from about from 2% to about 7%, including all integers within the specified range. In another aspect, the weight percentage of pectin in the gel mass is about 2%. In another aspect, the weight percentage of pectin in the gel mass is about 3%. In another aspect, the weight percentage of pectin in the gel mass is about 4%. In another aspect, the weight percentage of pectin in the gel mass is about 5%. In another aspect, the weight percentage of enteric pectin in the gel mass is about 6%. In another aspect, the weight percentage of enteric pectin in the gel mass is about 7%.

In another embodiment described herein, the enteric acid insoluble polymer comprises an enteric acid insoluble polymer comprising poly(meth)acrylates (methacrylic acid copolymer; e.g., EUDRAGIT®. In one embodiment described herein, the weight percentage of enteric acid insoluble polymer comprises from about 2% to about 30% including all integers within the specified range. In another embodiment described herein, the weight percentage of enteric acid insoluble polymer comprises from about 8% to about 15% including all integers within the specified range. In one aspect, the weight percentage of enteric acid insoluble polymer is about 9.5%. In another aspect, the weight percentage of enteric acid insoluble polymer is about 11%. In another aspect, the weight percentage of enteric acid insoluble polymer is about 14%.

In one embodiment described herein, the weight percentage of poly(methacylic acid-co-ethyl acrylate) 1:1 in the enteric soft capsule gel mass composition comprises from about 2% to about 15%, including all iterations of integers within the specified range. In one aspect, the weight percentage of poly(methacylic acid-co-ethyl acrylate) 1:1 in the gel mass is about 6%. In another aspect, the weight percentage of poly(methacylic acid-co-ethyl acrylate) 1:1 in the gel mass is about 9%. In another aspect, the weight percentage of poly(methacylic acid-co-ethyl acrylate) 1:1 in the gel mass is about 11%. In another aspect, the weight percentage of poly(methacylic acid-co-ethyl acrylate) 1:1 in the gel mass is about 13%.

In one embodiment described herein, the weight percentage of poly(ethyl acrylate-co-methyl methacrylate) 2:1 in the enteric soft capsule gel mass comprises from about 0.25% to about 4%, including all iterations of integers within the specified range. In one aspect, the weight percentage of poly(ethyl acrylate-co-methyl methacrylate) 2:1 in the gel mass is about 0.25%. In another aspect, the weight percentage of poly(ethyl acrylate-co-methyl methacrylate) 2:1 in the gel mass is about 2%. In another aspect, the weight percentage of poly(ethyl acrylate-co-methyl methacrylate) 2:1 in the gel mass is about 4%.

In one embodiment described herein, the weight percentage of poly(methyl acrylate-co-methyl methacrylate-co-methacrylic acid) 7:3:1 in the enteric soft capsule gel mass comprises from about 1% to about 14%, including all iterations of integers within the specified range. In one aspect, the weight percentage of poly(methyl acrylate-co-methyl methacrylate-co-methacrylic acid) 7:3:1 in the gel mass is about 1%. In another aspect, the weight percentage of poly(methyl acrylate-co-methyl methacrylate-co-methacrylic acid) 7:3:1 in the gel mass is about 5%. In another aspect, the weight percentage of poly(methyl acrylate-co-methyl methacrylate-co-methacrylic acid) 7:3:1 in the gel mass is about 8%. In another aspect, the weight percentage of poly(methyl acrylate-co-methyl methacrylate-co-methacrylic acid) 7:3:1 in the gel mass is about 12%. In another aspect, the weight percentage of poly(methyl acrylate-co-methyl methacrylate-co-methacrylic acid) 7:3:1 in the gel mass is about 14%.

In one embodiment, the alkali neutralizing-agent is ammonia (ammonium hydroxide; 30% w/v) that is added to comprise a weight percentage from about 1% to about 5% of the total enteric soft capsule gel mass. In one aspect, 30% w/v ammonia is added to comprise a weight percentage of about 2% of the gel mass. In another aspect, 30% w/v ammonia is added to a weight percentage of about 1.7% of the gel mass. In another aspect, ammonia is added to provide a final pH of about 9 in the enteric soft capsule gel mass. In another aspect, ammonia is added to provide a final pH of about 8.5 in the enteric soft capsule gel mass. In another aspect, after the capsules are filled and dried, the ammonia concentration is substantially reduced, owing to the fugitive nature of the volatile alkali. In another aspect, practically all of the ammonia is evaporated except for ammonium ions comprising salts with other moieties in the gel mass composition.

In one aspect, 30% w/v ammonia is added to comprise a weight percentage of about 2% of the gel mass. In another aspect, 30% w/v ammonia is added to comprise a weight percentage of about 3.5% of the gel mass.

In one embodiment described herein, the solvent comprises from about 10% to about 70% of the enteric soft capsule composition, including all integers within the specified range. In one embodiment, the solvent comprises water.

The quantity of water in the composition varies depending on the quantities of the other ingredients. For example, the quantity of opacifier, coloring, flavoring, or other excipients can change the percentage of water present in the composition. In one embodiment, the weight percentage of water comprises as much as suffices to bring the total weight percentage to 100% (i.e., quantum sufficiat; q.s.). In another embodiment, the water comprises about 70%, about 60%, about 50%, about 40%, about 30%, about 20% or about 10%, of the enteric soft capsule composition. In one aspect, water comprises about 45% of the enteric soft capsule composition. In one aspect, water comprises about 46% of the enteric soft capsule composition. In one aspect, water comprises about 44% of the enteric soft capsule composition.

In one embodiment described herein, the final moisture (water) content of the enteric soft capsule shell formed from the compositions described herein comprises from about 8% to about 20%, including all integers within the specified range. In another embodiment, the moisture content of the enteric soft capsule shell comprises from about 8% to about 12%, including all integers within the specified range. In one aspect, the final moisture content of the enteric soft capsule shell is about 8%. In one aspect, the final moisture content of the enteric soft capsule is about 9%. In one aspect, the final moisture content of the enteric soft capsule shell is about 10%. In one aspect, the final moisture content of the enteric soft capsule shell is about 11%. In another aspect, the final moisture content of the enteric soft capsule shell is about 12%.

In one embodiment described herein, the weight percentage range of total plasticizer in the enteric soft capsule composition comprises from about 6% to about 40%, including all iterations of integers within the specified range. In another embodiment, the weight percentage range of total plasticizer in the gel mass comprises from about 3% to about 20%, including all iterations of integers within the specified range. In another embodiment, the weight percentage range of total plasticizer in the gel mass comprises from about 9% to about 18%, including all iterations of integers within the specified range. In one aspect, the total plasticizer weight percentage in the gel mass is about 11%. In another aspect, the total plasticizer weight percentage is about 13%. In another aspect, the total plasticizer weight percentage in the gel mass is about 15%. In another aspect, the total plasticizer weight percentage in the gel mass is about 16%. In another aspect, the total plasticizer weight percentage in the gel mass is about 17%. In another aspect, the total plasticizer weight percentage in the gel mass is about 18%.

In one embodiment described herein, the weight percentage range of filler or bulking agent in the enteric soft capsule composition comprises from about 8% to about 20%, including all iterations of integers within the specified range. In another embodiment, the weight percentage range of filler in the gel mass comprises from about 9% to about 14%, including all iterations of integers within the specified range. In another embodiment, the weight percentage range of filler in the gel mass comprises from about 9% to about 12%, including all iterations of integers within the specified range. In one aspect, the filler weight percentage in the gel mass is about 13%. In another aspect, the filler weight percentage in the gel mass is about 12%. In another aspect, the total plasticizer weight percentage is about 11%. In another aspect, the filler weight percentage in the gel mass is about 10%. In one aspect, the filler weight percentage is about 9%. In another aspect, the total plasticizer weight percentage in the gel mass is about 9.2%.

In one embodiment described herein, the weight percentage range of gelling agent in the enteric soft capsule composition comprises from about 0.001% to about 1%, including all iterations of integers within the specified range. In one aspect, the weight percentage range of gelling agent in the gel mass is about 0.001%. In another aspect, the weight percentage range of gelling agent in the gel mass is about 0.005%. In another aspect, the weight percentage range of gelling agent in the gel mass is about 0.01%. In another aspect, the weight percentage range of gelling agent in the gel mass is about 0.025%. In another aspect, the weight percentage range of gelling agent in the gel mass is about 0.05%. In another aspect, the weight percentage range of gelling agent in the gel mass is about 0.075%. In another aspect, the weight percentage range of gelling agent in the gel mass is about 0.1%. In another aspect, the weight percentage range of gelling agent in the gel mass is about 0.5%. In another aspect, the weight percentage range of gelling agent in the gel mass is about 1%.

In one embodiment described herein, the alkali neutralizing agent is ammonia (e.g., ammonium hydroxide; 30% w/v) that is added to comprise a weight percentage from about 1% to about 5% of the total enteric soft capsule composition. The ammonia is added neat and dilution is not considered in calculating the weight percentage; thus, the weight percentage indicated is the weight percentage of 30% ammonium hydroxide added to the composition. In one aspect, ammonia comprises a weight percentage of about 2% of the gel mass. In another aspect, ammonia comprises a weight percentage of about 1.7% of the gel mass. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In some aspects, practically all of the fugitive ammonia is evaporated from the gel mass except for ammonium ions comprising salts with other components of the composition.

In one embodiment, the alkali neutralizing-agent is a 40 mg/mL solution of sodium hydroxide (NaOH 1 M) that is added to comprise a weight percentage of about 1% to about 7% of the total enteric soft capsule gel mass corresponding to a final concentration of NaOH from about 0.4 mg/mL to about 2.8 mg/mL of NaOH. In one aspect, the amount of 1 M NaOH is added to comprise about 2% of the total enteric soft capsule gel mass corresponding to a final concentration of NaOH of about 0.8 mg/mL. In another aspect, the amount of 1 M NaOH is added to comprise about 3.5% of the total enteric soft capsule gel mass corresponding to a final concentration of NaOH of about 1.4 mg/mL. In another aspect, the amount of 1 M NaOH is added to comprise about 5% of the total enteric soft capsule gel mass corresponding to a final concentration of NaOH of about 2 mg/mL.

In one embodiment described herein, the weight percentage range of total gelatin based (total gelatin content and enteric-acid insoluble polymer) of the enteric soft capsule composition described herein comprises from about 12% to about 70%, including all integers within the specified range. In one embodiment, the weight percentage range of total polymer content of the enteric soft capsule composition described herein comprises from about 25% to about 50%, including all integers within the specified range. In one aspect, the total cross-linked polymer weight percentage in the gel mass is about 31%. In another aspect, the total cross-linked polymer weight percentage in the gel mass is about 35%. In another aspect, the total cross-linked polymer weight percentage in the gel mass is about 40%. In another aspect, the total cross-linked polymer weight percentage in the gel mass is about 45%.

In one embodiment described herein, the weight percentage range of total ionically bonded polymer content (total gelatin content and anionic polymer (e.g., an anionic polysaccharide) of the enteric soft capsule composition described herein comprises from about 28% to about 41%, including all integers within the specified range. In one aspect, the total ionically bonded polymer weight percentage in the gel mass is about 31%. In another aspect, the total ionically bonded polymer weight percentage in the gel mass is about 35%. In another aspect, the total ionically bonded polymer weight percentage in the gel mass is about 40%.

In one embodiment, the weight ratio range of gelatin film forming polymer to enteric acid insoluble polymer (gelatin film forming: enteric) comprises about 1:2 to about 25:1, including all ratios within the specified range. In one embodiment, the weight ratio range of gelatin film forming polymer to enteric acid insoluble polymer (gelatin film forming: enteric) comprises from about 1:1 (≈1) to about 10:1, including all ratios within the specified range. In one embodiment, the weight ratio range of gelatin film forming polymer to enteric acid insoluble polymer (gelatin film forming: enteric) comprises from about 3:1 to about 7:1, including all ratios within the specified range. In one aspect, the ratio of gelatin film forming polymer to enteric acid insoluble polymer is about 3:1 In another aspect, the ratio of gelatin film forming polymer to enteric acid insoluble polymer is about 5:1. In another aspect, the ratio of gelatin film forming polymer to enteric acid insoluble polymer is about 6.5:1.

In one embodiment, the weight ratio range of poly(methacylic acid-co-ethyl acrylate) 1:1 to total enteric polymer in the enteric soft capsule gel mass comprises from about 1:7 to about 1:1. In one aspect, the weight ratio of poly(methacylic acid-co-ethyl acrylate) 1:1 to total enteric polymer in the enteric soft capsule gel mass is about 1:1.

In one embodiment, the weight ratio range of poly(ethyl acrylate-co-methyl methacrylate) 2:1 to total enteric polymer in the enteric soft capsule gel mass comprises from about 1:50 to about 1:4. In one aspect, the weight ratio of poly(ethyl acrylate-co-methyl methacrylate) 2:1 to total enteric polymer in the enteric soft capsule gel mass is about 1:50.

In one embodiment, the weight ratio range of poly(methyl acrylate-co-methyl methacrylate-co-methacrylic acid) 7:3:1 to total enteric polymer in the enteric soft capsule gel mass comprises from about 1:6 to about 1:1. In one aspect, the weight ratio of poly(methyl acrylate-co-methyl methacrylate-co-methacrylic acid) 7:3:1 to total enteric polymer in the enteric soft capsule gel mass is about 1:1.3.

In one embodiment, the weight ratio range of poly(methacylic acid-co-ethyl acrylate) 1:1 to poly(ethyl acrylate-co-methyl methacrylate) 2:1 in the enteric soft capsule gel mass comprises from about 1:1 to about 44:1, including all iterations of ratios within the specified range. In one aspect, the weight ratio of poly(methacylic acid-co-ethyl acrylate) 1:1 to poly(ethyl acrylate-co-methyl methacrylate) 2:1 in the enteric soft capsule gel mass is about 44:1.

In one embodiment, the weight ratio range of poly(methacylic acid-co-ethyl acrylate) 1:1 to poly(methyl acrylate-co-methyl methacrylate-co-methacrylic acid) 7:3:1 in the enteric soft capsule gel mass comprises from about 1:6 to about 5:1, including all iterations of ratios within the specified range. In one aspect, the weight ratio of poly(methacylic acid-co-ethyl acrylate) 1:1 to poly(methyl acrylate-co-methyl methacrylate-co-methacrylic acid) 7:3:1 in the enteric soft capsule gel mass is about 1:4. In another aspect, the ratio of poly(methacylic acid-co-ethyl acrylate) 1:1 to poly(methyl acrylate-co-methyl methacrylate-co-methacrylic acid) 7:3:1 in the gel mass is about 4:1. In another aspect, the ratio of poly(methacylic acid-co-ethyl acrylate) 1:1 to poly(methyl acrylate-co-methyl methacrylate-co-methacrylic acid) 7:3:1 in the gel mass is about 7.5:1.

In one embodiment, the enteric soft capsule gel masses described herein, are unexpectedly more flowable and less viscous than soft capsule gel masses generated with structurally similar poly(methacylic acid-co-methyl methacrylate) anionic copolymers (e.g., poly(methacylic acid-co-methyl methacrylate) 1:1). In one aspect, the aforementioned above gel masses result in enteric soft capsules that are less brittle and more efficiently generated through rotary die encapsulation methods known in the art.

In another embodiment described herein, enteric soft capsule gel masses can be generated to be even less viscous and more flowable with a combination of poly(methacylic acid-co-ethyl acrylate) 1:1 and poly(ethyl acrylate-co-methyl methacrylate) 2:1.

In another embodiment described herein, enteric soft capsules generated from gel masses comprising poly(methacylic acid-co-ethyl acrylate) 1:1 and poly(methyl acrylate-co-methyl methacrylate-co-methacrylic acid) 7:3:1 as described herein comprise modified release profiles (e.g., release at pH greater than 7.0 or colonic release). In one aspect, the ratio of poly(methacylic acid-co-ethyl acrylate) 1:1 to poly(methyl acrylate-co-methyl methacrylate-co-methacrylic acid) 7:3:1 in the enteric soft capsule shell gel masses is adjusted to determine the location in the gastrointestinal tract where capsule shell dissolution occurs. In another aspect, ratios of poly(methacylic acid-co-ethyl acrylate) 1:1 to poly(methyl acrylate-co-methyl methacrylate-co-methacrylic acid) 7:3:1 of at least about 1:3 or greater in the gel mass promote capsule shell dissolution at higher pH values.

In one embodiment, the weight ratio range of alkali neutralizing-agent to enteric polymer in the enteric soft capsule gel mass comprises from about 1:14 to about 1:1.7, including all iterations of ratios within the specified range. In one aspect, the ratio of alkali neutralizing-agent to enteric polymer in the gel mass is about 5:1. In another aspect, the ratio of alkali neutralizing-agent to enteric polymer in the gel mass is about 1:6. In another aspect, the ratio of alkali neutralizing-agent to enteric polymer in the gel mass is about 1:4. In another aspect, the ratio of alkali neutralizing-agent to enteric polymer in the gel mass is about 1:3.

In one embodiment described herein, the weight percentage ratio range of total gelatin to anionic polymer of the enteric soft capsule composition described herein comprises from about 4:1 to about 19:1, including all ratios within the specified range. In one aspect, the weight percentage ratio of total gelatin to anionic polymer in the gel mass is about 4:1. In one aspect, the weight percentage ratio of total gelatin to anionic polymer in the gel mass is about 6:1. In one aspect, the weight percentage ratio of total gelatin to anionic polymer in the gel mass is about 10:1. In one aspect, the weight percentage ratio of total gelatin to anionic polymer in the gel mass is about 12:1. In one aspect, the weight percentage ratio of total gelatin to anionic polymer in the gel mass is about 15:1. In one aspect, the weight percentage ratio of total gelatin to anionic polymer in the gel mass is about 19:1.

In one embodiment, the weight ratio range of gelatin to plasticizer comprises from about 1:4 to about 9:1, including all ratios within the specified range. In one embodiment, the weight ratio range of gelatin to plasticizer comprises from about 1:2 to about 5:1, including all ratios within the specified range. In one embodiment, the weight ratio range of gelatin to plasticizer comprises from about 1:1 to about 3:1, including all ratios within the specified range. In one aspect, the weight ratio of gelatin to plasticizer is about 1.6:1. In another aspect, the weight ratio of plasticizer to enteric acid insoluble polymer is about 2:1.

In one embodiment described herein, the weight ratio range of total plasticizer to total polymer (i.e., film forming and enteric) in the enteric soft gel composition comprises from about 1:11.5 (≈0.87) to about 3:1, including all ratios within the specified range. In one embodiment described herein, the weight ratio range of total plasticizer to total polymer (i.e., film forming and enteric) in the enteric soft gel composition comprises from about 1:7 to about 2:1, including all ratios within the specified range. In one embodiment described herein, the weight ratio range of total plasticizer to total polymer (i.e., film forming and enteric) in the enteric soft gel composition comprises from about 1:1 to about 2:1, including all ratios within the specified range. In one aspect, the weight ratio range of total plasticizer to total polymer in the gel mass is about 1:1. In another aspect, the weight ratio range of total plasticizer to total polymer in the gel mass is about 1.6:1.

In one embodiment described herein, the weight ratio range of total plasticizer to total polymer (i.e., film forming and enteric) in the enteric soft gel composition comprises from about 1:2 to about 1:1.1 (i.e., ≈0.50-0.9), including all ratios within the specified range. In one aspect, the weight ratio range of total plasticizer to total polymer in the gel mass is about 1:1.25 (≈0.80). In another aspect, the weight ratio range of total plasticizer to total polymer in the gel mass is about 1:1.4 (≈0.7). In another aspect, the weight ratio range of total plasticizer to total polymer in the gel mass is about 1.1.6 (≈0.6). In another aspect, the weight ratio range of total plasticizer to total polymer in the gel mass is about 1:2 (≈0.5).

In one embodiment described herein, the weight ratio range of total plasticizer to filler or bulking agent (e.g., hydroxypropyl starch phosphate) in the enteric soft gel composition comprises from about 1:1.16 to about 1.2:1 (≈0.6-1.2), including all ratios within the specified range. In one aspect, the weight ratio of total plasticizer to enteric polymer in the gel mass is about 1.1:1 (≈1.1). In another aspect, the weight ratio of total plasticizer to enteric polymer in the gel mass is about 1:1.1 (≈0.9). In another aspect, the weight ratio of total plasticizer to enteric polymer is about 1:1.14 (≈0.7). In another aspect, the weight ratio of total plasticizer to enteric polymer in the gel mass is about 1:1.16 (≈0.6).

In one embodiment, the weight ratio range of plasticizer to enteric acid insoluble polymer (plasticizer: enteric) comprises from about 1:5 to about 20:1, including all ratios within the specified range. In one embodiment, the weight ratio range of plasticizer to enteric acid insoluble polymer (plasticizer: enteric) comprises from about 1:2 to about 5:1, including all ratios within the specified range. In one embodiment, the weight ratio range of plasticizer to enteric acid insoluble polymer (plasticizer: enteric) comprises from about 1:1 to about 2:1, including all ratios within the specified range. In one aspect, the ratio of plasticizer to enteric acid insoluble polymer is about 5:3 (≈1.7). In another aspect, the ratio of plasticizer to enteric acid insoluble polymer is about 1:1.

In one embodiment described herein, the weight ratio range of enteric polymer to filler (e.g., hydroxypropyl starch phosphate) in the enteric soft gel composition comprises from about 1:1.4 (≈0.7) to about 1.2:1 (≈1.2) (i.e., 0.7-1.2), including all ratios within the specified range. In some aspects, the ratio of film forming polymer to filler in the gel mass is about 1:1.4 (≈0.7), about 1:1.25 (≈0.8), about 1:1.1 (≈0.9), about 1:1 (≈1), or about 1.1:1 (≈1.1). In one aspect, the ratio of film forming polymer to filler in the gel mass is about 1.1:1 (≈1.1).

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

Films of the enteric soft capsule shell do not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. Enteric soft capsules made using the compositions described herein remain intact in hydrochloric acid or simulated gastric fluid for at least two hours. The capsules readily release the contents upon shifting the pH of the solution to ca. 6.8, such as that of simulated intestinal fluid.

In another embodiment, the final enteric capsule composition provides films of increased strength without substantially compromising film elasticity. Moreover, films made from the enteric soft capsule compositions as described herein are sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing an enteric soft capsule comprising a pharmaceutical composition using rotary die technology. The thickness of the films or ribbons that form the enteric capsule shell is from about 0.010 inches (≈0.254 mm) to about 0.050 inches (≈1.27 mm), including all integers within the specified range. The shell thickness comprises about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the enteric soft capsule shell described herein, encapsulates a pharmaceutical composition as described herein. In another embodiment described herein, the enteric soft capsule shell and encapsulated pharmaceutical composition comprises an outer dimension from about 2 oval to about 30 oval including all iterations of capsule sizes within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the enteric soft capsule shell and encapsulated pharmaceutical composition comprises an outer dimension from about 2 round to about 28 round including all iterations of capsule sizes within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated pharmaceutical composition comprises an outer dimension from about 2 oblong to about 22 oblong including all iterations of capsule sizes within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In one embodiment, the soft enteric capsules comprising fish oil in the matrix fills described herein are stable for months or years. In one aspect, the pharmaceutical compositions described herein are stable at 25° C. and 60% relative humidity (RH) for about 1 month, about 2 months, about 3 months, about 4 months, about 5 months, about 6 months, about 9 months, about 10 months, about 11 months, about 12 months, or even longer. In another aspect, the pharmaceutical compositions described herein are stable for 1 year or longer at 25° C. and 60% RH. In another aspect, the pharmaceutical compositions described herein are stable for 2 years or longer at 25° C. and 60% RH.

In one embodiment, the pharmaceutical composition described herein is provided as a dosage kit in a dispensing receptacle. In one aspect, the dispensing receptacle is a moisture proof blister pack, strip pack, aluminum blister, transparent or opaque polymer blister with pouch, polypropylene tubes, colored blister materials, tubes, bottles, and bottles optionally containing a child-resistant feature, optionally comprising a desiccant, such as a molecular sieve or a silica gel. In another aspect, the dosage forms are packaged in a dispensing receptacle, which may optionally be packaged together in a box or other enclosure. In another aspect, the dispensing receptacle comprises sufficient amounts of the pharmaceutical composition described herein, for 1 day, 2 days, 6 days, 12 days, 24 days, 30 days, 60 days, or 90 days of dosing. In another aspect, the unit dosage form is about 250 mg to about 5000 mg of the pharmaceutical composition comprising an enteric soft capsule and matrix fill as described herein. In another aspect, the dosage kit comprises 1, 2, 6, 12, 24, 30, 60, 90, 120, 150, 180, 240, 270, or 300 such enteric soft capsules.

In one embodiment, the pharmaceutical composition described herein provides a dosage of a fatty acid composition for administration to a subject. In one embodiment, the fatty acid composition can be administered to a subject without unpleasant side effects, including but not limited to, gastric disturbances such as eructation (belching), bloating, and unpleasant fishy after tastes (e.g., "fishy burps"). The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject can be from ~0 years of age to 99 years of age or older including all iterations of integers within the specified range. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In another embodiment, a pharmaceutical composition is administered to a subject in an amount sufficient to provide a therapeutically effective dose of the fatty acids (e.g., fish oil comprising DHA, EPA, or DPA or a combination thereof) described herein of at least about 1 mg to at least about 10,000 mg, at least about 25 mg at least about 5000 mg, at least about 50 mg to at least about 3000 mg, at least about 75 mg to at least about 2500 mg, or at least about 100 mg to at least about 1000 mg. In one aspect, the pharmaceutical composition is administered to a subject and comprises a therapeutically effective dosage amount of the fatty acids (e.g., fish oil comprising DHA, EPA, or DPA) of at least about 50 mg, at least about 75 mg, at least about 100 mg, at least about 125 mg, at least about 150 mg, at least about 175 mg, at least about 200 mg, at least about 225 mg, at least about 250 mg, at least about 275 mg, at least about 300 mg, at least about 325 mg, at least about 350 mg, at least about 375 mg, at least about 400 mg, at least about 425 mg, at least about 450 mg, at least about 475 mg, at least about 500 mg, at least about 525 mg, at least about 550 mg, at least about 575 mg, at least about 600 mg, at least about 625 mg, at least about 650 mg, at least about 675 mg, at least about 700 mg, at least about 725 mg, at least about 750 mg, at least about 775 mg, at least about 800 mg, at least about 825 mg, at least about 850 mg, at least about 875 mg, at least about 900 mg, at least about 925 mg, at least about 950 mg, at least about 975 mg, at least about 1000 mg, at least about 1025 mg, at least about 1050 mg, at least about 1075 mg, at least about 1100 mg, at least about 1125 mg, at least about 1150 mg, at least about 1175 mg, at least about 1200 mg, at least about 1225 mg, at least about 1250 mg, at least about 1275 mg, at least about 1300 mg, at least about 1325 mg, at least about 1350 mg, at least about 1375 mg, at least about 1400 mg, at least about 1425 mg, at least about 1450 mg, at least about 1475 mg, at least about, 1500 mg, at least about 1525 mg, at least about 1550 mg, at least about 1575 mg, at least about 1600 mg, at least about 1625 mg, at least about 1650 mg, at least about 1675 mg, at least about 1700 mg, at least about 1725 mg, at least about 1750 mg, at least about 1775 mg, at least about 1800 mg, at least about 1825 mg, at least about 1850 mg, at least about 1875 mg, at least about 1900 mg, at least about 1925 mg, at least about 1950 mg, at least about 1975 mg, at least about 2000 mg, at least about 2025 mg, at least about 2050 mg, at least about 2075 mg, at least about 2100 mg, at least about 2125 mg, at least about 2150 mg, at least about 2175 mg, at least about 2200 mg, at least about 2225 mg, at least about 2250 mg, at least about 2275 mg, at least about 2300 mg, at least about 2325 mg, at least about 2350 mg, at least about 2375 mg, at least about 2400 mg, at least about 2425 mg, at least about 2450 mg, at least about 2475 mg, at least about 2500 mg, at least about 2525 mg, at least about 2550 mg, at least about 2575 mg, at least about 2600 mg, at least about 2625 mg, at least about 2650 mg, at least about 2675 mg, at least about 2700 mg, at least about 2725 mg, at least about 2750 mg, at least about 2775 mg, at least about 2800 mg, at least about 2825 mg, at least about 2850 mg, at least about 2875 mg, at least about 2900 mg, at least about 2925 mg, at least about 2950 mg, at least about 2975 mg, at least about 3000 mg, at least about 3025 mg, at least about 3050 mg, at least about 3075 mg, at least about 3100 mg, at least about 3125 mg, at least about 3150 mg, at least about 3175 mg, at least about 3200 mg, at least about 3225 mg, at least about 3250 mg, at least about 3275 mg, at least about 3300 mg, at least about 3325 mg, at least about 3350 mg, at least about 3375 mg, at least about 3400 mg, at least about 3425 mg, at least about 3450 mg, at least about 3475 mg, at least about 3500 mg, at least about 3525 mg, at least about 3550 mg, at least about 3600 mg, at least about 3625 mg, at least about 3650 mg, at least about 3675 mg, at least about 3700 mg, at least about 3725 mg, at least about 3750 mg, at least about 3775 mg, at least about 3800 mg, at least about 3825 mg, at least about 3850 mg, at least about 3875 mg, at least about 4000 mg, at least about 4025 mg, at least about 4050 mg, at least about 4075 mg, at least about 4100 mg, at least about 4125 mg, at least about 4150 mg, at least about 4175 mg, at least about 4200 mg, at least about 4225 mg, at least about 4250 mg, at least about 4275 mg, at least about 4300 mg, at least about 4325 mg, at least about 4350 mg, at least about 4375 mg, at least about 4400 mg, at least about 4425 mg, at least about 4450 mg, at least about 4475 mg, at least about 4500 mg, at least about 4525 mg, at least about 4550 mg, at least about 4600 mg, at least about 4625 mg, at least about 4650 mg, at least about 4675 mg, at least about 4700 mg, at least about 4725 mg, at least about 4750 mg, at least about 4775 mg, at least about 4800 mg, at least about 4825 mg, at least about 4850 mg, at least about 4875 mg, or at least about 5000 mg.

In one embodiment, the effective amount of fatty acids administered to a patient or subject in need thereof of is at least about 250 mg per dosage. In another embodiment, the effective amount of fatty acids administered to a patient or subject in need thereof is at least about 400 mg per dosage. In another embodiment, the effective amount of fatty acids administered to a patient or subject in need thereof is at least about 500 mg per dosage. In another embodiment, the effective amount of fatty acids administered to a patient or subject in need thereof is at least about 600 mg per dosage. In another embodiment, the effective amount of fatty acids administered to a patient or subject in need thereof is at least about 800 mg per dosage. In another embodiment, the effective amount of fatty acids administered to a patient or subject in need thereof is at least about 900 mg per dosage. In another embodiment, the effective amount of fatty acids administered to a patient or subject in need thereof is at least about 1000 mg per dosage. In another embodiment, the effective amount of fatty acids administered to a patient or subject in need thereof is at least about 1200 mg per dosage. In another embodiment, the effective amount of fatty acids administered to a patient or subject in need thereof is at least about 1400 mg per dosage. In another embodiment, the effective amount of fatty acids administered to a patient or subject in need thereof is at least about 2000 mg per dosage. In another embodiment, the effective amount of fatty acids administered to a patient or subject in need thereof is at least about 3000 mg per dosage. In another embodiment, the effective amount of fatty acids administered to a patient or subject in need thereof is at least about 4000 mg per dosage.

In one embodiment, the pharmaceutical composition is administered in an amount of at least about 250 mg per day. In one embodiment, the pharmaceutical composition is administered in an amount of at least about 500 mg per day. In one embodiment, the pharmaceutical composition is administered in an amount of at least about 1000 mg per day. In another embodiment, the pharmaceutical composition is administered in an amount of at least about 2000 mg per day. In another embodiment, the pharmaceutical composition is administered in an amount of at least about 3000 mg per day. In another embodiment, the pharmaceutical composition is administered in an amount of at least about 4000 mg per day. In another embodiment, the pharmaceutical composition is administered in an amount of at least about 5000 mg per day.

In one embodiment, the pharmaceutical composition is administered daily. In another embodiment, the pharmaceutical composition is administered every other day. In another embodiment, the daily dosage of pharmaceutical composition is administered in a single daily dose. In another embodiment, the pharmaceutical composition is administered in divided doses, with the daily dose divided into two administrations, three administrations, or four administrations per day. The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to hyperdyslipidemia or a cardiovascular-related disease.

In one embodiment, the pharmaceutical composition is administered with food. In another embodiment, the pharmaceutical composition is administered with a low fat meal. In another embodiment, the pharmaceutical composition is administered without food. In another embodiment, the pharmaceutical composition is administered in the fasting state.

In one embodiment, the administration of the pharmaceutical composition described herein depends on the physician, dose, and patient in need of treatment thereof. See, LOVAZA® (omega-3 acid ethyl esters) capsules, for oral use prescribing information, GlaxoSmithKline (2013); VASCEPA® (icosapent ethyl) capsules, for oral use prescribing information, Amarin Pharma Inc. (2013); and EPANOVA® (omega-3 carboxylic acids) capsules, for oral use prescribing information AstraZeneca Pharmaceuticals (2014); each of which is incorporated herein for the specific teachings thereof.

In another embodiment, the pharmaceutical composition described herein further comprises one or more non-steroidal anti-inflammatory drugs (NSAIDS). The NSAID may be co-administered, administered separately, or combined in the dosage form. See, e.g., WO 2013/155430, which is incorporated by reference herein for such teachings. The NSAID can be administered about 30 minutes before taking a dosage form described herein.

In another embodiment, the active ingredient comprises a fatty acid or derivatives thereof, combined with aspirin, ibuprofen, naproxene, diclofenac, ketoprofen, celecoxib, other non-steroidal anti-inflamatory active drugs (NSAIDs), or combinations thereof. In one embodiment, the pharmaceutical composition comprises a PUFA combined with aspirin.

In another embodiment, the pharmaceutical composition described herein further comprises one or more statins (HMG-CoA reductase inhibitors) comprising atorvastatin, lovastatin, simvastatin, pravastatin, rosuvastatin, fluvastatin, pitavastatin, himastatin, or combinations thereof. The statin may be co-administered, administered separately, or combined in the dosage form.

In another embodiment, the pharmaceutical composition described herein further comprises one or more cardiovascular drugs, including ACE inhibitors, aldosterone inhibitors, angiotensin II receptor blockers, beta-blockers, calcium channel blockers, or combinations thereof. The cardiovascular drugs may be co-administered, administered separately, or combined in the dosage form.

One embodiment described herein is a method for treating, retarding the progression of, delaying the onset of, prophylaxis of, amelioration of, or reducing the symptoms of a disease related to hyperdyslipidemia using a pharmaceutical composition as described herein. Another embodiment described herein is a method for treating, retarding the progression of, delaying the onset of, prophylaxis of, amelioration of, or reducing the symptoms of a cardiovascular-related disease using a pharmaceutical composition as described herein. See U.S. Patent Application Publication No. US 2010/0278879, which is incorporated by reference herein for its specific teachings of treating cardiovascular-related diseases. The term "cardiovascular-related disease" as used herein refers to any disease or disorder of the heart or blood vessels (i.e., arteries and veins) or any symptom thereof. The term "cardiovascular-related disease" as used herein also refers any disease or condition that causes or contributes to a "cardiovascular disease." Non-limiting examples of "cardiovascular-related diseases" include acute cardiac ischemic events, acute myocardial infarction, angina, angina pectoris, arrhythmia, atrial fibrillation, atherosclerosis, arterial fibrillation, cardiac insufficiency, cardiovascular disease, chronic heart failure, chronic stable angina, congestive heart failure, coronary artery disease, coronary heart disease, deep vein thrombosis, diabetes, diabetes mellitus, diabetic neuropathy, diastolic dysfunction in subjects with diabetes mellitus, edema, essential hypertension, eventual pulmonary embolism, fatty liver disease, heart disease, heart failure, homozygous familial hypercholesterolemia (HoFH), homozygous familial sitosterolemia, hypercholesterolemia, hyperlipidemia, hyperlipidemia in HIV positive subjects, hypertension, hypertriglyceridemia, ischemic complications in unstable angina and myocardial infarction, low blood pressure, metabolic syndrome, mixed dyslipidemia, moderate to mild heart failure, myocardial infarction, obesity management, paroxysmal atrial/arterial fibrillation/fibrillation/flutter, paroxysmal supraventricular tachycardias (PSVT), particularly severe or rapid onset edema, platelet aggregation, primary hypercholesterolemia, primary hyperlipidemia, pulmonary arterial hypertension, pulmonary hypertension, recurrent hemodynamically unstable ventricular tachycardia (VT), recurrent ventricular arrhythmias, recurrent ventricular fibrillation (VF), ruptured aneurysm, sitosterolemia, stroke, supraventricular tachycardia, symptomatic atrial fibrillation/flutter, tachycardia, type II diabetes, vascular disease, venous thromboembolism, ventricular arrhythmias, and other cardiovascular events. The term "treatment" as used herein in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In another embodiment, the pharmaceutical composition is suitable for the treatment, prevention, amelioration of a plurality of diseases and symptoms comprising high blood pressure, cancer, rheumatoid arthritis, menstrual pain (dysmenorrhea), attention deficit-hyperactivity disorder (ADHD) in children, attention deficit-hyperactivity disorder (ADHD) in adults, Raynaud's syndrome, stroke, weak bones (e.g., osteoporosis), hardening of the arteries (e.g., atherosclerosis), kidney problems, bipolar disorder, psychosis, weight loss, endometrial cancer, age-related eye disease (age-related macular degeneration, amd), reducing the risk of blood vessel re-blockage after heart bypass surgery or "balloon" catheterization (e.g., balloon angioplasty), recurrent miscarriage in pregnant women with antiphospholipid syndrome, kidney problems following heart transplant, kidney damage following cyclosporine therapy, movement disorder in children (e.g., dyspraxia), developmental coordination disorder, preventing blockage of grafts used in kidney dialysis, psoriasis, high cholesterol, recovery after coronary artery bypass surgery, cancer-related weight loss, asthma, allergies, Alzheimer's disease, atopic dermatitis, atrial fibrillation, depression, dry eye syndrome, cataracts, chronic fatigue syndrome (CFS), chronic kidney disease, reduced thinking skills (e.g., cognitive function), Crohn's disease, prediabetes, infant development, ulcerative colitis, pregnancy complications, salicylate intolerance, schizophrenia, systemic lupus erythematosus (SLE), irregular heartbeat affecting the ventricles (ventricular arrhythmias), improving night vision in children with dyslexia or a combination of disease symptoms described herein.

In another embodiment, the pharmaceutical composition is suitable for the treatment, prevention, amelioration of a cardiovascular-related disease comprising hyperlipidemia, hypertriglyceridemia, hypertension, hypercholesterolemia, mixed dyslipidemia, sitosterolemia, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), ventricular arrhythmias, angina pectoris, unstable angina (UA), and stable angina (SA), myocardial infarction, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, peripheral vascular disease, and peripheral artery disease, rheumatoid arthritis, dysmenorrhea, attention deficit-hyperactivity disorder in children, attention deficit-hyperactivity disorder in adults, Raynaud's syndrome, stroke, osteoporosis, kidney problems, bipolar disorder, psychosis, weight loss, endometrial cancer, macular degeneration, kidney damage, dyspraxia, developmental coordination disorder, psoriasis, asthma, allergies, Alzheimer's disease, atopic dermatitis, atrial fibrillation, depression, dry eye syndrome, cataracts, chronic fatigue syndrome (CFS), chronic kidney disease, Crohn's disease, prediabetes, ulcerative colitis, salicylate intolerance, schizophrenia, systemic lupus erythematosus (SLE), or a combination thereof.

In one embodiment described herein, for the treatment of cardiovascular-related diseases (e.g., hyperlipidemia, hypertriglyceridemia, hypertension, hypercholesterolemia, mixed dyslipidemia, inter alia), the dosage form administered to the subject or subject in need thereof may comprise a fatty acid as the only active ingredient or in combination with one or more non-steroidal anti-inflammatory drugs (e.g., aspirin, ibuprofen, naproxen, ketoprofen, celecoxib, or combinations thereof), statins (e.g., atorvastatin, lovastatin, simvastatin, pravastatin, rosuvastatin, fluvastatin, pitavastatin, himastatin, or combinations thereof), or cardiovascular drugs (e.g., ACE inhibitors, aldosterone inhibitors, angiotensin II receptor blockers, beta-blockers, calcium channel blockers, or combinations thereof).

One embodiment described herein is a method of blood lipid therapy comprising administering to a subject or subject group in need thereof the pharmaceutical composition as described herein. In one aspect, the subject may be a mammal, or a mammal in need thereof. In one aspect, the dosage form can be administered, for example, to a human or a human in need thereof. In one aspect, the human subject or a human subject in need thereof is a medical patient. In another embodiment, the subject or subject group has hypertriglyceridemia, hypercholesterolemia, mixed dyslipidemia, very high triglycerides, or a mixture thereof.

In another embodiment, the subject or subject group being treated has a baseline triglyceride level (or median baseline triglyceride level in the case of a subject group), fed or fasting, of at least about 200 mg/dL, at least about 300 mg/dL, at least about 400 mg/dL, at least about 500 mg/dL, at least about 600 mg/dL, at least about 700 mg/dL, at least about 800 mg/dL, at least about 900 mg/dL, at least about 1000 mg/dL, at least about 1100 mg/dL, at least about 1200 mg/dL, at least about 1300 mg/dL, at least about 1400 mg/dL, at least about 1500 mg/dL, at least about 1600 mg/dL, at least about 1700 mg/dL, at least about 1800 mg/dL, at least about 1900 mg/dL, at least about 2000 mg/dL, at least about 2100 mg/dL, at least about 2200 mg/dL, at least about 2300 mg/dL, at least about 2400 mg/dL, or at least about 2500 mg/dL.

In another embodiment, the subject's (or subject group's mean) baseline lipid profile is measured prior to initiating therapy. In another embodiment, subjects or a subject group comprising a baseline non-HDL-C value of about 200 mg/dL to about 400 mg/dL, for example at least about 210 mg/dL, at least about 220 mg/dL, at least about 230 mg/dL, at least about 240 mg/dL, at least about 250 mg/dL, at least about 260 mg/dL, at least about 270 mg/dL, at least about 280 mg/dL, at least about 290 mg/dL, or at least about 300 mg/dL; baseline total cholesterol value of about 250 mg/dL to about 400 mg/dL, for example at least about 260 mg/dL, at least about 270 mg/dL, at least about 280 mg/dL or at least about 290 mg/dL; baseline vLDL-C value of about 140 mg/dL to about 200 mg/dL, for example at least about 150 mg/dL, at least about 160 mg/dL, at least about 170 mg/dL, at least about 180 mg/dL or at least about 190 mg/dL; baseline HDL-C value of about 10 mg/dL to about 60 mg/dL, for example not more than about 40 mg/dL, not more than about 35 mg/dL, not more than about 30 mg/dL, not more than about 25 mg/dL, not more than about 20 mg/dL, or not more than about 15 mg/dL; and/or baseline LDL-C value of about 50 mg/dL to about 300 mg/dL, for example not less than about 100 mg/dL, not less than about 90 mg/dL, not less than about 80 mg/dL, not less than about 70 mg/dL, not less than about 60 mg/dL or not less than about 50 mg/dL.

In one embodiment, upon treatment of a subject or subject group in need thereof with the pharmaceutical composition described herein over a period of about 1 week to about 200 weeks, about 1 week to about 100 weeks, about 1 week to about 80 weeks, about 1 week to about 50 weeks, about 1 week to about 40 weeks, about 1 week to about 20 weeks, about 1 week to about 15 weeks, about 1 week to about 12 weeks, about 1 week to about 10 weeks, about 1 week to about 5 weeks, about 1 week to about 2 weeks or about 1 week, the subject or subject group exhibits one or more outcomes comprising reduced triglyceride levels compared to baseline measurements, reduced Apo B levels compared to baseline measurements, increased HDL-C levels compared to baseline measurements, no increase in LDL-C levels compared to baseline measurements, a reduction in LDL-C levels compared to baseline measurements, a reduction in non-HDL-C levels compared to baseline measurements, a reduction in vLDL levels compared to baseline measurements, an increase in apo A-I levels compared to baseline measurements, an increase in apo A-I/apo B ratio compared to baseline measurements, a reduction in lipoprotein A levels compared to baseline measurements, a reduction in LDL particle number compared to baseline measurements, an increase in mean LDL size compared to baseline measurements, a reduction in remnant-like particle cholesterol compared to baseline measurements, a reduction in oxidized LDL compared to baseline measurements, no change or a reduction in fasting plasma glucose (FPG) compared to baseline measurements, a reduction in hemoglobin $A_c$ (HbA) compared to baseline measurements, a reduction in homeostasis model insulin resistance compared to baseline measurements, a reduction in lipoprotein associated phospholipase A2 compared to baseline measurements, a reduction in Intracellular Adhesion Molecule 1 compared to baseline measurements, a reduction in Interleukin-6 compared to baseline measurements, a reduction in Plasminogen Activator Inhibitor 1 compared to baseline measurements, a reduction in high sensitivity C-reactive protein (hsCRP) compared to baseline measurements, an increase in serum phospholipid EPA compared to baseline measurements, an increase in red blood cell membrane EPA compared to baseline measurements, or any mixture of outcomes thereof.

In another embodiment, upon treatment with the pharmaceutical composition described herein, the subject or subject group exhibits an outcome comprising, a reduction in triglyceride levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline measurements.

In another embodiment, upon treatment with the pharmaceutical composition described herein, the subject or subject group exhibits an outcome comprising a less than 30% increase, less than 20% increase, less than 10% increase, less than 5% increase or no increase in non-HDL-C levels, or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% (actual % change or median % change) as compared to baseline measurements; or substantially no change, no change or an increase in HDL-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% (actual % change or median % change) as compared to baseline measurements; or a less than 60% increase, less than 50% increase, less than 40% increase, less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% (actual % change or median % change) as compared to baseline measurements or a decrease in Apo B levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% (actual % change or median % change) as compared to baseline measurements or a reduction in vLDL levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements or an increase in apo A-I levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or an increase in apo A-I/apo B ratio of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in lipoprotein(a) levels of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in mean LDL particle number of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or an increase in mean LDL particle size of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in remnant-like particle cholesterol of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in oxidized LDL of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or substantially no change, no change or a reduction in fasting plasma glucose (FPG) of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or substantially no change, no change or a reduction in hemoglobin A (HbA) of at least about 5%, at least about 10%, at least about 15%, at least about 20%, at least about 25%, at least about 30%, at least about 35%, at least about 40%, at least about 45%, or at least about 50% (actual % change or median % change) compared to baseline or a placebo arm or a reduction in homeostasis model index insulin resistance of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline or a placebo arm; or a reduction in Lipoprotein Associated Phospholipase A2 of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in Intracellular Adhesion Molecule-1 of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in Interleukin-6 of at least about 5%, at least about 10%, at least about 15%, at least about 20%, at least about 25%, at least about 30%, at least about 35%, at least about 40%, at least about 45%, at least about 50%, at least about 60%, at least about 65%, at least about 70%, at least about 75%, at least about 80%, at least about 85%, at least about 90%, at least about 95%, or at least about 100% (actual % change or median % change) compared to baseline measurements; or a reduction in Plasminogen Activator Inhibitor 1 of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline; or a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% (actual % change or median % change) compared to baseline measurements; or an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200% or at least about 400% (actual % change or median % change) compared to baseline measurements; or an increase in serum phospholipid and/or red blood cell membrane EPA of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 200%, or at least about 400% (actual % change or median % change) compared to baseline measurements; or a reduction or increase in one or more of serum phospholipid and/or red blood cell DHA, DPA, AA, PA or OA of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, or at least about 75% (actual % change or median % change) compared to baseline measurements; or a reduction in total cholesterol of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, or at least about 75% (actual % change or median % change) compared to baseline measurements or any combination of outcomes thereof.

The listed parameters immediately above can be measured in accordance with any clinically acceptable methodology. For example, triglycerides, total cholesterol, HDL-C, and fasting blood sugar can be sample from serum and analyzed using standard photometry techniques. VLDL-TG, LDL-C, and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants of lipoproteins and LDL-Phospholipase A2 can be determined from EDTA plasma or serum and serum, respectively, using enzymatic immunoseparation techniques. Oxidized LDL, Intercellular Adhesion Molecule-1 and Interleukin-2 levels can be determined from serum using standard enzyme immunoassay techniques known in the art.

In one embodiment, the pharmaceutical composition is administered in an amount and for a duration effective to reduce serum or plasma triglyceride levels by at least about 50 mg/dL to at least about 1000 mg/dL. In one aspect, the pharmaceutical composition is administered in an amount and for a duration effective to reduce serum or plasma triglyceride levels by at least about 50 mg/dL, at least about 60 mg/dL, at least about 70 mg/dL, at least about 80 mg/dL, at least about 90 mg/dL, at least about 100 mg/dL. In another aspect, the pharmaceutical composition is administered in an amount and for a duration effective to reduce serum or plasma triglyceride levels by at least about 110 mg/dL, at least about 120 mg/dL, at least about 130 mg/dL, at least about 140 mg/dL, or at least about 150 mg/dL. In another aspect, the pharmaceutical composition is administered in an amount and for a duration effective to reduce serum or plasma triglyceride levels by at least about 160 mg/dL, at least about 170 mg/dL, at least about 180 mg/dL, at least about 190 mg/dL, or at least about 200 mg/dL. In another aspect, the pharmaceutical composition is administered in an amount and for a duration effective to reduce serum or plasma triglyceride levels by at least about 210 mg/dL, at least about 220 mg/dL, at least about 230 mg/dL, at least about at least about 240 mg/dL, or at least about 250 mg/dL. In another aspect, the pharmaceutical composition is administered in an amount and for a duration effective to reduce serum or plasma triglyceride levels by at least about 260 mg/dL, 270 mg/dL, at least about 280 mg/dL, at least about 290 mg/dL, or at least about 300 mg/dL. In another aspect, the pharmaceutical composition is administered in an amount and for a duration effective to reduce serum or plasma triglyceride levels by at least about 350 mg/dL, at least about 400 mg/dL, at least about 450 mg/dL, or at least about 500 mg/dL. In another aspect, the pharmaceutical composition is administered in an amount and for a duration effective to reduce serum or plasma triglyceride levels by at least about 600 mg/dL, at least about 700 mg/dL, at least about 800 mg/dL, at least about 900 mg/dL, or at least about 1000 mg/dL.

In one embodiment, the pharmaceutical composition is administered in an amount and for a duration effective to reduce serum or plasma triglyceride levels to an amount less than about 1000 mg/dL. In another embodiment, the pharmaceutical composition is administered in an amount and for a duration effective to reduce serum or plasma triglyceride levels to an amount less than about 900 mg/dL. In another embodiment, the pharmaceutical composition is administered in an amount and for a duration effective to reduce serum or plasma triglyceride levels to an amount less than about 800 mg/dL. In another embodiment, the pharmaceutical composition is administered in an amount and for a duration effective to reduce serum or plasma triglyceride levels to an amount less than about 700 mg/dL. In another embodiment, the pharmaceutical composition is administered in an amount and for a duration effective to reduce serum or plasma triglyceride levels to an amount less than about 600 mg/dL. In another embodiment, the pharmaceutical composition is administered in an amount and for a duration effective to reduce serum or plasma triglyceride levels to an amount less than about 500 mg/dL. In another embodiment, the pharmaceutical composition is administered in an amount and for a duration effective to reduce serum or plasma triglyceride levels to an amount less than about 400 mg/dL. In another embodiment, the pharmaceutical composition is administered in an amount and for a duration effective to reduce serum or plasma triglyceride levels to an amount less than about 350 mg/dL. In another embodiment, the pharmaceutical composition is administered in an amount and for a duration effective to reduce serum or plasma triglyceride levels to an amount less than about 300 mg/dL. In another embodiment, the pharmaceutical composition is administered in an amount and for a duration effective to reduce serum or plasma triglyceride levels to an amount less than about 200 mg/dL. In another embodiment, the pharmaceutical composition is administered in an amount and for a duration effective to reduce serum or plasma triglyceride levels to an amount less than about 150 mg/dL. In another embodiment, the pharmaceutical composition is administered in an amount and for a duration effective to reduce serum or plasma triglyceride levels to an amount less than about 120 mg/dL.

In another embodiment, methods of treating or preventing risk of recurrent nonfatal myocardial infarction in a patient with a history of myocardial infarction comprise administering to the patient one or more pharmaceutical compositions as disclosed herein.

In another embodiment, methods of slowing progression of or promoting regression of atherosclerotic disease in a patient in need thereof, comprise administering to a subject in need thereof one or more pharmaceutical compositions as disclosed herein.

In another embodiment, methods of treating or preventing very high serum triglyceride levels (e.g., Types IV and V hyperlipidemia) in a patient in need thereof, comprise administering to the patient one or more pharmaceutical compositions as disclosed herein.

In another embodiment, methods of treating subjects having very high serum triglyceride levels (e.g., greater than 1000 mg/dL or greater than 2000 mg/dL) and that are at risk of developing pancreatitis, comprise administering to the patient one or more pharmaceutical compositions as disclosed herein.

In one embodiment, the pharmaceutical composition is administered in an amount and for a duration effective to increase plasma EPA levels by at least 100% above pre-treatment levels. In another embodiment, the pharmaceutical composition is administered in an amount and for a duration effective to increase plasma EPA levels by at least about 200%, at least about 250%, at least about 300%, at least about 350%, at least about 400%, at least about 450%, at least about 500%, at least about 750%, at least about 1000%, at least about 1500%, or at least about 2000% above pre-treatment levels. In another embodiment, the pharmaceutical composition is administered for a time and in an amount effective to increase plasma EPA levels by at least about 2000% above pre-treatment levels.

In one embodiment, the pharmaceutical composition is administered in an amount and for a duration effective to increase plasma DHA levels by at least about 50% above pre-treatment levels. In another embodiment, the pharmaceutical composition is administered in an amount and for a duration effective to increase plasma DHA levels by at least about 55%, at least about 60%, at least about 65%, at least about 70%, at least about 75%, at least about 80%, at least about 85%, or at least about 90% above pre-treatment levels.

In one embodiment, the pharmaceutical composition is administered in an amount and for a duration effective to increase plasma DPA levels by at least about 50% above pre-treatment levels. In another embodiment, the pharmaceutical composition is administered in an amount and for a duration effective to increase plasma DPA levels by at least about 55%, at least about 60%, at least about 65%, at least about 70%, at least about 75%, at least about 80%, at least about 85%, at least about 90%, at least about 95%, or at least about 100% above pre-treatment levels. In another embodiment, the pharmaceutical composition is administered in an amount and for a duration effective to increase plasma DPA levels by at least about 110%, at least about 120%, or at least about 125% above pre-treatment levels.

In one embodiment, the pharmaceutical composition is administered in an amount and for a duration effective to reduce arachidonic acid (AA) concentration in plasma by at least about 5% below pre-treatment levels. In another embodiment, the pharmaceutical composition is administered in an amount and for a duration effective to reduce arachidonic (AA) concentration in plasma by at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, or at least about 25% below pre-treatment levels.

In one embodiment, the pharmaceutical composition is administered in an amount and for a duration effective to reduce plasma arachidonic acid concentration by at least about 25 µg/mL. In another embodiment, the pharmaceutical composition is administered in an amount and for a duration sufficient to reduce plasma AA levels by at least about 50 µg/mL, at least about 55 µg/mL, at least about 60 µg/mL, at least about 65 µg/mL, at least about 70 µg/mL, at least about 75 µg/mL, at least about 80 µg/mL, at least about at least about 85 µg/mL, at least about 90 µg/mL, at least about 95 µg/mL or at least about 100 µg/mL.

Methods are also provided for increasing the EPA:AA ratio, without regard to the patient's pretreatment plasma triglyceride levels. The methods comprise administering the pharmaceutical composition described herein, to a patient having an EPA:AA ratio below at least about 0.25, in an amount and for a duration sufficient to increase the patient's EPA:AA ratio to at least about 0.25. In one embodiment, the pharmaceutical composition is administered in an amount and for a duration sufficient to increase the patient's EPA:AA ratio to at least about 0.3, at least about 0.35, at least about 0.40, at least about 0.45, at least about 0.50, at least about 0.55, at least about 0.60, at least about 0.61, at least about 0.62, at least about 0.63, at least about 0.64, or at least about 0.65.

In one embodiment, the pharmaceutical composition is administered in an amount, and for a duration, effective to reduce plasma arachidonic acid concentration by at least about 25 pg/mL. In another embodiment, the pharmaceutical composition is administered in an amount and for a duration sufficient to reduce plasma AA levels by at least about 50 pg/mL, at least about 55 pg/mL, at least about 60 pg/mL, at least about 65 pg/mL, at least about 70 pg/mL, at least about 75 pg/mL, at least about 80 pg/mL, at least about 85 pg/mL, at least about 90 pg/mL, at least about 95 pg/mL or at least about 100 pg/mL.

Methods are also provided for increasing a patient's serum or plasma ApoCIII levels, without regard to the patient's pretreatment plasma triglyceride levels. The methods comprise administering the pharmaceutical composition described in herein to a patient in need of lower ApoCIII levels, in an amount and for a duration sufficient to decrease the patient's serum or plasma ApoCIII levels. In another embodiment, the patient is at risk for cardiovascular heart disease.

In one embodiment, the pharmaceutical compositions described herein minimize disruptive eructation and unpleasant fishy odors and aftertaste.

Another embodiment described herein is a pharmaceutical composition for administration to a subject with hyperdyslipidemia or a cardiovascular-related disease comprising a therapeutically effective amount of the fatty acids described herein, wherein the subject achieves a reduction of the annualized disease relapse rate relative to baseline without substantially experiencing one or more of disruptive eructation and unpleasant fishy odors and aftertaste. In one aspect the reduction may be about 1%, about 2%, about 5%, about 10%, about 15%, about 20%, about 25%, about 30%, about 35%, about 45%, about 50%, or greater than about 50%.

Another embodiment described herein is a pharmaceutical composition or dosage form for treating, prophylaxis, or amelioration of hyperdyslipidemia or a cardiovascular-related disease comprising an effective amount of one or more fish oils (e.g., EPA, DHA or DPA or a combination thereof), wherein the composition exhibits an in vitro dissolution rate (% dissolution per minute) at pH 6.8, as described herein.

Another embodiment described herein is a pharmaceutical composition for treating, prophylaxis, or amelioration of hyperdyslipidemia including but not limited to cardiovascular-related diseases comprising one or more fish oils (e.g., EPA, DHA or DPA or a combination thereof), wherein the composition exhibits an in vitro dissolution rate comprising about 10% to about 80% dissolution after about 5 minutes to about 480 minutes at pH 6.8, including each integer within the specified rages of dissolution and time. In another aspect, the in vitro dissolution rate at pH 6.8 is about 50% after about 20 minutes.

In one embodiment, the pharmaceutical composition described herein is suitable for oral administration. In one aspect, the pharmaceutical composition described herein is administered orally.

In one embodiment, the pharmaceutical composition described herein provides a relatively short $T_{max}$ of EPA yet still maintains excellent stability of the encapsulated material. In one aspect, the composition is provided in a dosage form containing a total amount of EPA wherein subjects administered the dosage form exhibit a mean plasma EPA $T_{max}$ ranging from about 5 hours to about 6 hours including all iterations of integers within the specified range. In another aspect, the composition is provided in a dosage form containing a total amount of EPA, wherein subjects administered the dosage form once daily exhibit a mean plasma EPA $T_{max}$ of at least 4 hours, at least 4.2 hours, at least 4.4 hours, at least 4.6 hours, at least 4.8 hours, at least 5 hours, at least 5.2 hours, at least 5.4 hours, at least 5.6 hours, at least 5.8 hours, at least 6 hours, at least 6.2 hours, at least 6.4 hours, or at least 6.6 hours.

In one embodiment, the pharmaceutical composition described herein is provided in a dosage form containing a total amount of EPA wherein subjects administered the dosage form exhibit a mean plasma EPA $C_{max}$ ranging from about 20 mg/L to about 500 mg/L including all iterations of integers within the specified range. In another aspect, the composition is provided in a dosage form containing a total amount of EPA wherein subjects administered the dosage form exhibit a mean plasma EPA $C_{max}$ ranging from about 100 mg/L to about 250 mg/L including all iterations of integers within the specified range. In another aspect, the composition is provided in a dosage form containing a total amount of EPA wherein subjects administered the dosage form exhibit a mean plasma EPA $C_{max}$ of at least about 20 mg/L, at least about 40 mg/L, at least about 60 mg/L, at least about 80 mg/L, at least about 100 mg/L, at least about 150 mg/L, at least about 200 mg/L, or at least about 250 mg/L. In one embodiment, the pharmaceutical composition is provided in a dosage form containing a total amount of EPA wherein subjects administered the dosage form exhibit a mean plasma EPA $C_{max}$ of at least about 120 mg/L to about 230 mg/L.

In one embodiment, the pharmaceutical composition described herein is provided in a dosage form containing a total amount of EPA wherein subjects administered the dosage form exhibit a mean plasma EPA $AUC_{0 \to \tau}$ ranging from about 300 h·mg/L to about 8500 h·mg/L including all iterations of integers within the specified range. In one aspect, the composition is provided in a dosage form containing a total amount of EPA wherein subjects administered the dosage form exhibit a mean plasma EPA $AUC_{0 \to \tau}$ ranging from about 1800 h·mg/L to about 3000 h·mg/L including all iterations of integers within the specified range. In another aspect, the composition is provided in a dosage form containing a total amount of EPA wherein subjects administered the dosage form exhibit a mean plasma EPA $AUC_{0 \to \tau}$ ranging from about 2500 h·mg/L to about 5000 h·mg/L including all iterations of integers within the specified range. In another aspect, the composition is provided in a dosage form containing a total amount of EPA wherein subjects administered the dosage form exhibit a mean plasma EPA $AUC_{0 \to \infty}$ ranging from about 5000 h·mg/L to about 8500 h·mg/L including all iterations of integers within the specified range. In another aspect, the composition is provided in a dosage form containing a total amount of EPA wherein subjects administered the dosage form exhibit a mean plasma EPA $AUC_{0 \to \infty}$ of at least about 500 h·mg/L, at least about 600 h·mg/L, at least about 700 h·mg/L, at least about 800 h·mg/L, at least about 900 h·mg/L, at least about 1000 h·mg/L, at least about 1250 h·mg/L, at least about 1500 h·mg/L, at least about 1750 h·mg/L, at least about 2000 h·mg/L, at least about 2250 h·mg/L, at least about 2500 h·mg/L, at least about 2750 h·mg/L, or at least about 3000 h·mg/L. In one embodiment, the pharmaceutical composition described herein is provided in a dosage form containing a total amount of EPA wherein subjects administered the dosage form exhibit a mean plasma EPA $AUC_{0 \to \infty}$ ranging from about 1850 h·mg/L to about 2900 h·mg/L including all iterations of integers within the specified range.

In one embodiment, the pharmaceutical composition described herein is provided in a dosage form containing a total amount of EPA wherein subjects administered the dosage form exhibit a mean plasma EPA $AUC_{0 \to \infty}$ ranging from about 1000 h·mg/L to about 8500 h·mg/L including all iterations of integers within the specified range. In one aspect, the composition is provided in a dosage form containing a total amount of EPA wherein subjects administered the dosage form exhibit a mean plasma EPA $AUC_{0 \to \infty}$ ranging from about 1800 h·mg/L to about 3000 h·mg/L including all iterations of integers within the specified range. In another aspect, the composition is provided in a dosage form containing a total amount of EPA wherein subjects administered the dosage form exhibit a mean plasma EPA $AUC_{0\to\infty}$ ranging from about 2000 h·mg/L to about 3000 h·mg/L including all iterations of integers within the specified range. In another aspect, the composition is provided in a dosage form containing a total amount of EPA wherein subjects administered the dosage form exhibit a mean plasma EPA $AUC_{0\to\tau}$ of at least about 2000 h·mg/L, at least about 2050 h·mg/L, at least about 2100 h·mg/L, at least about 2200 h·mg/L, at least about 2300 h·mg/L, at least about 2400 h·mg/L, at least about 2500 h·mg/L, at least about 2600 h·mg/L, at least about 2700 h·mg/L, at least about 2800 h·mg/L, at least about 2900 h·mg/L, or at least about 3000 h·mg/L. In one embodiment, the pharmaceutical composition described herein is provided in a dosage form containing a total amount of EPA wherein subjects administered the dosage form exhibit a mean plasma EPA $AUC_{0\to\infty}$ ranging from about 2050 h·mg/L to about 3000 h·mg/L including all iterations of integers within the specified range.

In one embodiment, the pharmaceutical composition described herein, when administered to a subject, provides one or more of the following pharmacokinetic parameters: (a) a mean plasma EPA $T_{max}$ of about 5 hours to about 6 hours; (b) a mean plasma EPA $C_{max}$ of about 110 mg/L to about 248 mg/L; (c) a mean plasma EPA $AUC_{0\to\tau}$ of about 1650 h·mg/L to about 3146 h·mg/L; (d) a mean plasma EPA $AUC_{0\to\infty}$ of about 1836·mg/L to about 3300 mg/L; (e) a mean EPA half-life (t½) of about 33 hours to about 47 hours; or (f) a mean EPA overall elimination rate constant ($k_{e1}$) of about $0.016\ h^{-1}$ to about $0.023\ h^{-1}$.

In one embodiment, the pharmaceutical composition described herein is provided in a dosage form containing a total amount of EPA wherein subjects administered the dosage form exhibit a bioavailability of greater than about 50% to about 2000% as compared to the bioavailability of a reference drug comprising EPA ethyl ester in a soft gelatin capsule. In one embodiment, the pharmaceutical composition described herein has a bioavailability of greater than about 50% to about 100% as compared to the bioavailability of a reference drug comprising EPA ethyl ester in a soft gelatin capsule when administered to a subject in the fed state or with a low-fat meal. In one embodiment, the pharmaceutical composition described herein has a bioavailability of greater than about 100% to about 200% as compared to the bioavailability of a reference drug comprising EPA ethyl ester in a soft gelatin capsule when administered to a subject in the fasted state or with a low-fat meal.

In another embodiment described herein, the pharmaceutical composition described herein provides enhanced bioavailability of EPA free fatty acid independent of the presence of food in a subject's gastrointestinal tract. Without being bound to any theory, it is believed that delivery of the EPA free fatty acid to the lower gastrointestinal tract (intestine) reduces the food-effect and improves absorption and uptake of the fatty acid into the bloodstream.

In another embodiment described herein, the pharmaceutical composition described herein comprises highly pure EPA free fatty acid when administered to a subject in need thereof does not induce a substantial increase in the subject's LDL level relative to baseline.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The ratios of the mass of any component of any of the formulations disclosed herein to the mass of any other component in the formulation or to the total mass of the other components in the formulation are hereby disclosed as if they were expressly disclosed. All patents and publications cited herein are incorporated by reference herein for the specific teachings thereof.

EXAMPLES

Example 1

Examples of gel mass compositions useful for producing enteric soft capsules described herein comprising the pharmaceutical compositions described herein are shown below in Table 3. Composition components are set forth by weight percentage of the total weight of the gel mass composition.

TABLE 3

Exemplary Enteric Soft Capsule Gel Composition

| Ingredient | Weight Percentage (%) | | | | | |
| --- | --- | --- | --- | --- | --- | --- |
| | EX 1 | EX 2 | EX 3 | EX 4 | EX 5 | EX 6 |
| Gelatin | 29.2 | 33.2 | 0 | 39.5 | 33 | 27.8 |
| Plasticizer | 18 | 16 | 10.4 | 20 | 15 | 17.8 |
| Pectin | 0 | 3.3 | 0 | 0 | 2.4 | 0 |
| poly(methacylic acid-co-methyl methacrylate) 1:1(L100) | 11.2 | 0 | 9.7 | 10 | 0 | 0 |
| poly(methacylic acid-co-ethyl acrylate) 1:1 (L100-55) | 0 | 0 | 0 | 0 | 0 | 10.8 |
| Ammonium hydroxide | 1.7 | 0 | 1.2 | 1.5 | 0 | |
| Sodium hydroxide | 0 | 0 | 0 | 0 | 0 | 3.6 |
| Triethyl citrate | 1.3 | 0 | 0 | 0 | 0 | 0 |
| Calcium chloride | 0 | 0 | 0 | 0 | 0.004 | 0 |
| Hydroxypropyl starch phosphate | 0 | 0 | 9.2 | 0 | 0 | 0 |
| Water | 38.7 | 47.5 | 63 | 19 | 49.1 | 40 |
| TOTAL | 100 | 100 | 100 | 100 | 100 | 100 |

Example 2

In one embodiment, the enteric soft capsule shell has the composition of Table 4, including all possible iterations of the specified ranges that provide 100% for the total weight percentage, including or excluding the optional, excipients, opacifiers, colorants, and flavorings.

TABLE 4

Exemplary Enteric Soft Capsule Shell Composition

| Component | Exemplary Component | Composition Range (%) |
| --- | --- | --- |
| Film-forming polymer | Gelatin | 20-36 |
| Enteric, acid-insoluble polymer | Methacrylic Acid Copolymer | 8-20 |
| Plasticizer | Glycerol, Triethyl citrate | 10-22 |
| Alkali-neutralizing agents | NH$_4$OH (30%), NaOH | 1-5 |
| Solvent | Water | 20-40 |
| Opacifier | Titanium Dioxide | 1-7.5 |

TABLE 4-continued

Exemplary Enteric Soft Capsule Shell Composition

| Component | Exemplary Component | Composition Range (%) |
|---|---|---|
| Colorant (optional) | Various | 0.05-1 |
| Flavoring (optional) | Various | 0.05-2 |
| Excipients (optional) | Various | 1-5 |

In one embodiment described herein, the enteric soft capsule shell has the exemplary composition shown in Table 5.

TABLE 5

Exemplary Enteric Soft Capsule Shell Composition

| Component | Percent Weight (%) |
|---|---|
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | 8.5-9.0 |
| Total polymer % weight (gelatin + enteric) | 40.4 |
| Gelatin % weight of total polymer (gelatin + enteric) | 72.4 |
| Enteric % weight of total polymer (gelatin + enteric) | 27.6 |
| Ratio of Enteric to Gelatin | 11.2:29.2 (0.38) |
| Total plasticizer % weight (glycerol + triethyl citrate) | 19.3 |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15 |

Example 3

In one embodiment described herein, the pharmaceutical composition described herein has the exemplary composition shown in Table 6.

TABLE 6

Exemplary Pharmaceutical Composition

| Component | Percent Weight (%) |
|---|---|
| Enteric Soft Capsule Shell | |
| Gelatin | 29.2 |
| Methacrylic Acid Copolymer (EUDRAGIT ® L 100) | 11.2 |
| Glycerol | 18.0 |

TABLE 6-continued

Exemplary Pharmaceutical Composition

| Component | Percent Weight (%) |
|---|---|
| Triethyl citrate | 1.3 |
| Ammonium hydroxide | 1.7 |
| Water | 38.6 |
| Total | 100% |
| API | |
| Eicosapentaenoic acid (EPA; free acid) 92-98%; nominally ~94% | 1000 mg |
| Other omega fatty acids, oils, vitamins, excipients: 4-8%; (Less than 1% DHA) | ~ |

Example 4

A single-center, randomized, open-label, single-dose, four-period, two sequence crossover clinical study with 32 healthy volunteers was performed to evaluate the bioavailability of the "Test" pharmaceutical composition comprising ~4000 mg (4×1000 mg) of ~94% eicosapentaenoic acid, free fatty acid (EPA-FFA) in an enteric soft gel capsule (see Table 6, above) as compared to a Reference Listed Drug (RLD) comprising ~4000 mg (4×960 mg) eicosapentaenoic acid ethyl ester (EPA-EE) in a typical soft gel capsule under fasted and high-fat dosing conditions.

The study was a 47-day trial that included a 21-day screening period and a 26-day treatment period. This study assessed the relative bioavailability of EPA free fatty acid as compared to an EPA ethyl ester formulation and to assess the safety and tolerability of a single 4-gram dose of EPA administered under fasting (i.e., low fat) and fed (i.e., high-fat) dosing conditions. See Table 7.

TABLE 7

Randomized Crossover Clinical Study

| Day 1 Period 1 Fasting/Low Fat Diet | Day 1 Period 2 Fasting/Low Fat Diet | Day 1 Period 3 Fed/High Fat Diet | Day 1 Period 4 Fed/High Fat Diet |
|---|---|---|---|
| Test: 16 Sub. (TL) → 4 g EPA-FFA | RLD: 16 Sub. (RL) → 4 g EPA-EE | Test: 16 Sub. (TH) → 4 g EPA-FFA | RLD: 16 Sub. (RH) → 4 g EPA-EE |
| RLD: 16 Sub. (RL) → 4 g EPA-EE | Test 16 Sub. (TL) → 4 g EPA-FFA | RLD: 16 Sub. (RH) → 4 g EPA-FFA | Test 16 Sub. (TH) → 4 g EPA-EE |

Thirty-two (32) healthy subjects (19 male; 59.4%; 13 female; 40.6%) were enrolled and randomized to treatment; 30 subjects (93.8%) completed the study as planned; 32 subjects (100.0%) were included in the Safety Population and 32 (100%) were included in the Pharmacokinetic (PK) Populations. Two (2) subjects discontinued participation in the study.

Subjects were representative of a healthy adult male and female population, ranging from 19 to 52 years of age. Overall mean (SD) age was 35.7 (10.32) years and mean (SD) BMI was 24.88 (2.376) kg/m$^2$. Racial composition was 12 (37.5%) black or African American and 20 (62.5%) white. Ethnicity was 19 (59.4%) Hispanic or Latino and 13 (40.6%) Non-Hispanic and Non-Latino.

The study consisted of a screening visit within 21 days before admission for Period 1, and admission to the unit at −49 hour pre-dose in each period, followed by four periods of single-dose administration of the study drugs. There was a minimum of ~7 days washout between each single-dose administration. Upon admission, on Day −3 of each period, subjects were given meals that followed the Therapeutic Lifestyle Changes (TLC) diet and that contained limited EPA (e.g., EPA-limited diet). See, e.g., *Your Guide to Lowering Cholesterol With Therapeutic Lifestyle Changes* (TLC), U.S. Department of Health and Human Services, National Institutes of Health, National Heart, Lung, and Blood Institute, NIH Publication ID: 06-5235, December 2005, which is incorporated by reference herein in its entirety for such teachings. Approximately 12 hours prior to dosing in all four periods, the subjects consumed a low fat dinner (9 g fat; 900 kcal).

The low fat meals for Periods 1 and 2 were as follows:
Day 1: (the day of dosing): no breakfast—fasting administration of drug (0 g fat; 0 kcal); no-fat lunch (0 g fat; 600 kcal); low-fat dinner (9 g fat; 900 kcal); no-fat evening snack.
Day 2: Meals followed the EPA-limited diet.

The high-fat meals for Periods 3 and 4 were as follows:
Day 1: high-fat breakfast, 45 minutes before dosing (20 g fat; 600 kcal); high-fat lunch (30 g fat; 900 kcal); high-fat dinner (30 g fat; 900 kcal); evening snack.
Day 2: Meals followed the EPA-limited diet.

Subjects resumed the TLC diet after the last samples at 48 hours post-dose during the outpatient portion of all periods. Subjects adhered to the TLC diet during the outpatient portions of the study and between Treatment Periods.

During each treatment period, subjects received one of the following open label treatments:
Test Formulation (T): a single dose of EPA free fatty acid, 4×1 g capsules
Reference Formulation (R): a single dose of EPA ethyl ester, 4×1 g capsules.

A total of 20 blood samples were collected from the subjects at time intervals of −24, −16, −8, −0.75 (time=0) hours pre-dosing and at 1, 2, 3, 4, 5, 6, 7, 8, 9, 10, 12, 14, 16, 24, 32, and 48 hours post dosing and were analyzed for the plasma bioavailability of the fatty acid. When meal time coincided with the blood sample time, the blood samples were collected prior to the meal being consumed.

The following PK parameters were determined using plasma concentrations of Total EPA and Free EPA (non-esterified EPA), as permitted by the data:
$C_{max}$: Maximum plasma concentration observed.
$T_{max}$: Time to maximum concentration observed.
$AUC_{0 \to \tau}$: Area under the plasma concentration-time curve from time 0 to the last quantifiable time point ($C_\tau$).
$AUC_{0 \to \infty}$: Area under the plasma concentration-time curve from time 0 to infinity, calculated as $AUC_{0 \to \tau} + C_\tau/\lambda z$.

The study's primary endpoints were the 90% Confidence Intervals on the ratio of the geometric means of the single-dose pharmacokinetic parameters $AUC_{0 \to \tau}$, $AUC_{0 \to \infty}$, and $C_{max}$ between the following treatment comparisons:
TL versus RL: Fasted administration of Test and Reference followed by low-fat diet.
TH versus RH: Fed administration of Test and Reference followed by high-fat diet.
TH versus TL: Food effect on Test.
RH versus RL: Food effect on Reference.
(TH/TL) versus (RH/RL): Ratio between food effect on the Test and food effect on the Reference.

Figure 6:
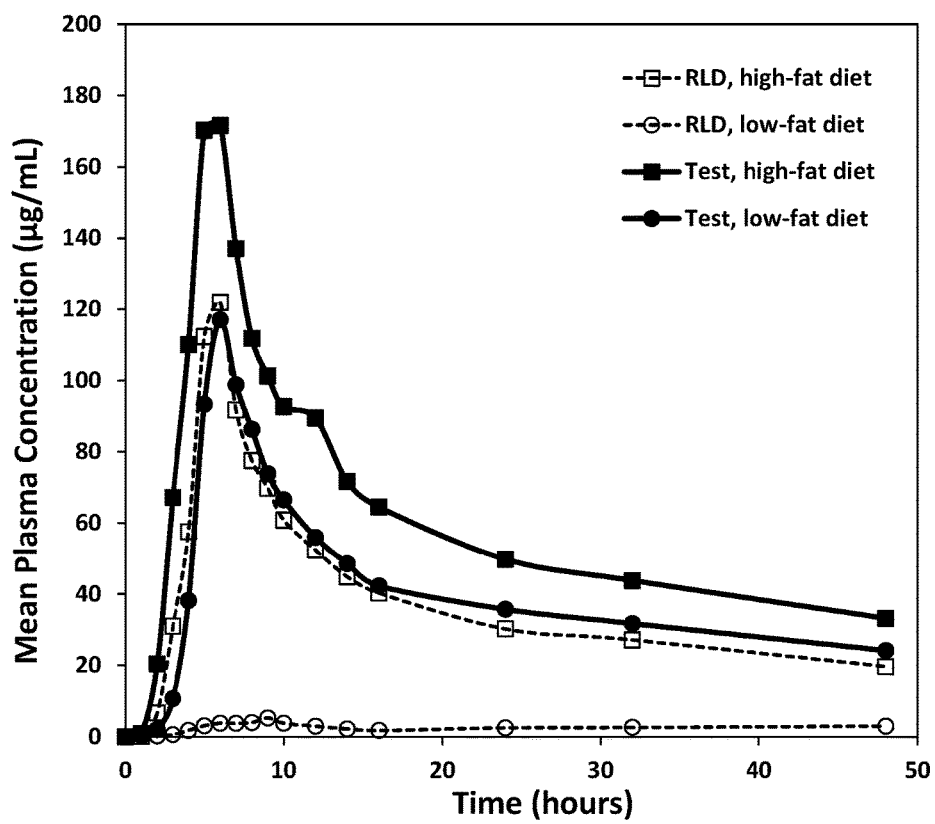
FIG. 6. Mean plasma concentration (g/mL) as a function of time and after ingestion of the RLD and the Test pharmaceutical composition shown in Table 6.

The parameters $AUC_{0 \to \tau}$, $AUC_{0 \to \infty}$, and $C_{max}$ were log transformed prior to analysis and were analyzed using a mixed model. Treatments were compared using an analysis of variance (ANOVA) model on the log-transformed data. The model includes sequence, period, and treatment as fixed effects and subject nested within sequence as a random effect. For AUCs and $C_{max}$, point estimates (lest square means) for treatment differences as well as the 90% Confidence Interval (CI) were calculated on log scales and then exponentiated to provide estimates of, and confidence intervals for, the geometric mean ratios. The residual variance from the mixed model was used to calculate the 90% CI for the difference between the Test and Reference treatment. Pharmacokinetic data and parameters are shown in Tables 8-15. The averaged plasma EPA free fatty acid (Test)/EPA ethyl ester (RLD) concentrations as a function of time are shown in FIG. 6.

TABLE 8

Mean Baseline-Adjusted Plasma Total EPA Pharmacokinetic Parameters by Treatment

| Parameter | Statistic | TL (Test) 4 g EPA-FFA Low Fat Diet | RL (RLD) 4 g EPA-EE Low Fat Diet | TH (Test) 4 g EPA-FFA High Fat Diet | RH (RLD) 4 g EPA-EE High Fat Diet |
|---|---|---|---|---|---|
| $AUC_{0 \to \tau}$ (hr · µg/mL) | n | 32 | 31 | 30 | 32 |
|  | Mean (SD) | 1841 (739.0) | 126.7 (92.68) | 2864 (1094) | 1781 (955.9) |
| $AUC_{0 \to \infty}$ (hr · µg/mL) | n | 2 | 2 | NA | 1 |
|  | Mean (SD) | 2044 (1105) | 27.64 (19.94) | NA | 3063 (NA) |
| $C_{max}$ (µg/mL) | n | 32 | 31 | 30 | 32 |
|  | Mean (SD) | 122.1 (62.55) | 7.507 (8.554) | 225.6 (99.88) | 136.6 (77.96) |
| $T_{max}$ (hr) | n | 32 | 31 | 30 | 32 |
|  | Median | 6.00 | 9.00 | 5.00 | 5.00 |
|  | Min, Max | 4.00, 10.00 | 4.00, 48.00 | 3.00, 12.00 | 4.00, 12.00 |
| $t_{1/2}$ (hr) | n | 28 | 4 | 29 | 31 |
|  | Mean (SD) | 43.34 (19.13) | 7.80 (5.44) | 36.88 (10.23) | 37.59 (9.96) |
| $k_{el}$ (1/hr) | n | 28 | 4 | 29 | 31 |
|  | Mean (SD) | 0.0190 (0.0083) | 0.1639 (0.1721) | 0.0202 (0.0055) | 0.0198 (0.0057) |
|  | Median | 0.0178 | 0.0946 | 0.0199 | 0.0192 |
|  | Min, Max | 0.0067, 0.0435 | 0.0465, 0.4197 | 0.0106, 0.0364 | 0.0118, 0.0351 |

TL: Test Fasting/Low-Fat Diet
RL: Reference Fasting/Low-Fat Diet
TH: Test High-Fat Diet
RH: Reference High-Fat Diet
n = number of subjects

TABLE 9

Mean Baseline-Adjusted Plasma Free EPA Pharmacokinetic Parameters by Treatment

| Parameter | Statistic | TL Test 4 g EPA-FFA Low Fat Diet | RL RLD 4 g EPA-EE Low Fat Diet | TH Test 4 g EPA-FFA High Fat Diet | RH RLD 4 g EPA-EE High Fat Diet |
|---|---|---|---|---|---|
| $AUC_{0 \to \tau}$ (hr · µg/mL) | n | 32 | 32 | 30 | 32 |
| | Mean (SD) | 8.810 (3.651) | 2.581 (1.094) | 12.96 (3.149) | 7.846 (2.707) |
| $AUC_{0 \to \infty}$ (hr · µg/mL) | n | NA | NA | 1 | NA |
| | Mean (SD) | NA | NA | 12.58 (NA) | NA |
| $C_{max}$ (µg/mL) | n | 32 | 32 | 30 | 32 |
| | Mean (SD) | 1.132 (0.6918) | 0.1271 (0.0570) | 1.894 (1.074) | 0.9911 (0.4644) |
| $T_{max}$ (hr) | n | 32 | 32 | 30 | 32 |
| | Median | 5.00 | 4.00 | 6.00 | 6.00 |
| | Min, Max | 4.00, 10.00 | 2.00, 48.00 | 4.00, 12.00 | 3.00, 10.00 |
| $t_{1/2}$ (hr) | n | 1 | 1 | 1 | NA |
| | Mean (SD) | 26.27 (NA) | 117.83 (NA) | 17.79 (NA) | NA (NA) |
| $k_{el}$ (1/hr) | n | 1 | 1 | 1 | NA |
| | Mean (SD) | 0.0264 (NA) | 0.0059 (NA) | 0.0390 (NA) | NA (NA) |
| | Median | 0.0264 | 0.0059 | 0.0390 | NA |
| | Min, Max | 0.0264, 0.0264 | 0.0059, 0.0059 | 0.0390, 0.0390 | NA |

TL: Test Fasting/Low-Fat Diet
RL: Reference Fasting/Low-Fat Diet
TH: Test High-Fat Diet
RH: Reference High-Fat Diet
n = number of subjects

TABLE 10

Bioavailability of Total and Free EPA Between EPA Free Fatty Acid (Fasting/Low-Fat Diet) and EPA Ethyl Ester (Fasting/Low-Fat Diet)

| Analyte | n | Param. | Geometric Least Square Means TL | Geometric Least Square Means RL | TL/RL Ratio (%) | 90% CI (LCL-UCL) | ISCV (%) |
|---|---|---|---|---|---|---|---|
| Total EPA (BA) | 30 | $C_{max}$ | 114.4 | 5.220 | 2191.79 | (1786.06-2689.68) | 49.25 |
| | | $AUC_{0 \to \tau}$ | 1796 | 88.78 | 2022.93 | (1564.59-2615.53) | 63.87 |
| Free EPA (BA) | 31 | $C_{max}$ | 0.9785 | 0.1144 | 855.46 | (708.56-1032.83) | 45.80 |
| | | $AUC_{0 \to \tau}$ | 8.543 | 2.109 | 405.12 | (330.77-496.19) | 49.67 |
| Total EPA (UN) | 31 | $C_{max}$ | 126.0 | 18.00 | 699.94 | (616.62-794.53) | 30.00 |
| | | $AUC_{0 \to \tau}$ | 2346 | 704.1 | 333.26 | (306.62-362.20) | 19.47 |
| Free EPA (UN) | 31 | $C_{max}$ | 1.010 | 0.1409 | 716.34 | (598.59-857.24) | 43.45 |
| | | $AUC_{0 \to \tau}$ | 9.811 | 3.205 | 306.13 | (248.11-377.70) | 51.69 |

BA: baseline adjusted
UN: uncorrected
n = number of subjects
TL: Test Fasting/Low-Fat Diet
RL: Reference Fasting Low-Fat Diet
CI = 90% confidence interval,
LCL = lower confidence limit,
UCL = upper confidence limit
ISCV = intra-subject coefficient of variation

TABLE 11

Bioavailability of Total and Free EPA Between EPA Free Fatty Acid (High-Fat Diet) and EPA Ethyl Ester (High Fat Diet)

| Analyte | n | Param. | Geometric Least Square Means TH | Geometric Least Square Means RH | TH/RH Ratio (%) | 90% CI (LCL-UCL) | ISCV (%) |
|---|---|---|---|---|---|---|---|
| Total EPA (BA) | 30 | $C_{max}$ | 206.6 | 110.6 | 186.80 | (149.23-233.82) | 54.51 |
| | | $AUC_{0 \to \tau}$ | 2702 | 1554 | 173.86 | (154.21-196.01) | 27.76 |
| Free EPA (BA) | 30 | $C_{max}$ | 1.662 | 0.8828 | 188.23 | (153.20-231.28) | 49.46 |
| | | $AUC_{0 \to \tau}$ | 12.64 | 7.353 | 171.98 | (152.05-194.52) | 28.53 |

TABLE 11-continued

Bioavailability of Total and Free EPA Between EPA Free Fatty Acid (High-Fat Diet) and EPA Ethyl Ester (High Fat Diet)

| Analyte | n | Param. | Geometric Least Square Means TH | Geometric Least Square Means RH | TH/RH Ratio (%) | 90% CI (LCL-UCL) | ISCV (%) |
|---|---|---|---|---|---|---|---|
| Total EPA (UN) | 30 | $C_{max}$ | 220.6 | 128.8 | 171.22 | (140.98-207.94) | 46.38 |
|  |  | $AUC_{0 \to \tau}$ | 3347 | 2327 | 143.82 | (133.28-155.18) | 17.40 |
| Free EPA (UN) | 30 | $C_{max}$ | 1.699 | 0.9299 | 182.68 | (150.05-222.41) | 47.04 |
|  |  | $AUC_{0 \to \tau}$ | 14.31 | 9.342 | 153.19 | (139.17-168.63) | 22.07 |

BA: baseline adjusted
UN: uncorrected
n = number of subjects
TH: Test High-Fat Diet
RL: Reference High-Fat Diet
CI = 90% confidence interval,
LCL = lower confidence limit,
UCL = upper confidence limit
ISCV = intra-subject coefficient of variation

TABLE 12

Food Effect of Total and Free EPA Between EPA Free Fatty Acid (Fed/High-Fat Diet) and EPA Free Fatty Acid (Fasting/Low-Fat Diet)

| Analyte | n | Param. | Geometric Least Square Means TH | Geometric Least Square Means TL | TH/TL Ratio (%) | 90% CI (LCL-UCL) | ISCV (%) |
|---|---|---|---|---|---|---|---|
| Total EPA (BA) | 29 | $C_{max}$ | 207.7 | 116.7 | 177.92 | (146.23-216.49) | 46.99 |
|  |  | $AUC_{0 \to \tau}$ | 2761 | 1817 | 151.92 | (131.17-175.95) | 34.39 |
| Free EPA (BA) | 29 | $C_{max}$ | 1.659 | 1.006 | 164.98 | (128.36-212.05) | 62.15 |
|  |  | $AUC_{0 \to \tau}$ | 12.71 | 8.744 | 145.41 | (127.34-166.04) | 30.91 |
| Total EPA (UN) | 29 | $C_{max}$ | 221.6 | 129.3 | 171.47 | (142.79-205.90) | 43.54 |
|  |  | $AUC_{0 \to \tau}$ | 3405 | 2380 | 143.10 | (125.64-163.00) | 30.29 |
| Free EPA (UN) | 29 | $C_{max}$ | 1.696 | 1.036 | 163.73 | (128.00-209.45) | 60.77 |
|  |  | $AUC_{0 \to \tau}$ | 14.37 | 9.999 | 143.68 | (126.26-163.51) | 30.08 |

BA: baseline adjusted
UN: uncorrected
n = number of subjects
TH: Test High-Fat Diet
TL: Test Fasting Low-Fat Diet
CI = 90% confidence interval,
LCL = lower confidence limit,
UCL = upper confidence limit
ISCV = intra-subject coefficient of variation

TABLE 13

Food Effect of Total and Free EPA Between EPA Ethyl Ester (Fed/High-Fat Diet) and EPA Ethyl Ester (Fasting/ Low-Fat Diet)

| Analyte | n | Param. | Geometric Least Square Means RH | Geometric Least Square Means RL | RH/RL Ratio (%) | 90% CI (LCL-UCL) | ISCV (%) |
|---|---|---|---|---|---|---|---|
| Total EPA (BA) | 31 | $C_{max}$ | 118.1 | 5.615 | 2104.04 | (1585.56-2792.07) | 74.82 |
|  |  | $AUC_{0 \to \tau}$ | 1626 | 89.93 | 1807.47 | (1313.56-2487.10) | 87.23 |
| Free EPA (BA) | 32 | $C_{max}$ | 0.8843 | 0.1164 | 759.79 | (625.53-922.86) | 49.22 |
|  |  | $AUC_{0 \to \tau}$ | 7.366 | 2.188 | 336.70 | (262.01-432.67) | 65.93 |
| Total EPA (UN) | 32 | $C_{max}$ | 132.3 | 18.72 | 707.01 | (577.24-865.96) | 51.59 |
|  |  | $AUC_{0 \to \tau}$ | 2359 | 699.0 | 337.43 | (290.15-392.40) | 37.37 |

TABLE 13-continued

Food Effect of Total and Free EPA Between EPA Ethyl Ester
(Fed/High-Fat Diet) and EPA Ethyl Ester (Fasting/ Low-Fat Diet)

| | | | Geometric Least Square Means | | | | |
|---|---|---|---|---|---|---|---|
| Analyte | n | Param. | RH | RL | RH/RL Ratio (%) | 90% CI (LCL-UCL) | ISCV (%) |
| Free EPA (UN) | 32 | $C_{max}$ | 0.9306 | 0.1430 | 650.77 | (536.97-788.67) | 48.59 |
| | | $AUC_{0 \to \tau}$ | 9.328 | 3.302 | 282.51 | (216.62-368.45) | 70.63 |

BA: baseline adjusted
UN: uncorrected
n = number of subjects
RH: Reference High-Fat Diet
RL: Reference Fasting Low-Fat Diet
CI = 90% confidence interval,
LCL = lower confidence limit,
UCL = upper confidence limit
ISCV = intra-subject coefficient of variation

TABLE 14

Bioavailability of Total and Free EPA Between EPA Free Fatty Acid
(Fed/High Fat Diet)/(Fasting/ Low-Fat Diet) and EPA Ethyl Ester
(Fed/High Fat Diet)/(Fasting/Low-Fat Diet)

| | | Geometric Least Square Means | | | | |
|---|---|---|---|---|---|---|
| Analyte | Param. | TH/TL n = 30 | RH/RL n = 30 | (TH/TL)/ (RH/RL) Ratio (%) | 90% CI (LCL-UCL) | ISCV (%) |
| Total EPA (BA) | $C_{max}$ | 2.203 | 21.04 | 10.47 | (7.08-15.49) | 109.82 |
| | $AUC_{0 \to \tau}$ | 1.904 | 18.07 | 10.53 | (6.50-17.07) | 160.39 |
| Free EPA (BA) | $C_{max}$ | 2.569 | 7.598 | 33.81 | (25.57-44.72) | 63.89 |
| | $AUC_{0 \to \tau}$ | 1.813 | 3.512 | 51.61 | (36.61-72.76) | 88.92 |
| Total EPA (UN) | $C_{max}$ | 1.947 | 7.070 | 27.54 | (21.37-35.49) | 64.04 |
| | $AUC_{0 \to \tau}$ | 1.618 | 3.374 | 47.95 | (38.09-60.35) | 58.45 |
| Free EPA (UN) | $C_{max}$ | 2.513 | 6.508 | 38.62 | (29.41-50.72) | 62.02 |
| | $AUC_{0 \to \tau}$ | 1.720 | 2.825 | 60.87 | (43.52-85.15) | 88.42 |

BA: baseline adjusted
UN: uncorrected
n = number of subjects
TH: Test High-Fat Diet
TL: Test Fasting Low-Fat Diet
RH: Reference High-Fat Diet
RL: Reference Fasting Low-Fat Diet
TH/TL: Ratio of Test High-Fat Diet to Low-Fat Diet
RH/RL: Ratio of Reference High-Fat Diet to Low-Fat Diet
CI = 90% confidence interval,
LCL = lower confidence limit,
UCL = upper confidence limit
ISCV = intra-subject coefficient of variation

TABLE 15

Summary Pharmacokinetic Parameters (Total EPA)

| Treatment | Dependent | Ref. | Test | Ratio % Ref | Lower 90% CI | Upper 90% CI |
|---|---|---|---|---|---|---|
| Reference | $Ln(C_{max})$ | RL | RH | 2029.11 | 1525.85 | 2698.36 |
| | $Ln(AUC_{0 \to \tau})$ | RL | RH | 1757.26 | 1279.08 | 2414.22 |
| Test | $Ln(C_{max})$ | TL | TH | 182.14 | 150.38 | 220.61 |
| | $Ln(AUC_{0 \to \tau})$ | TL | TH | 154.20 | 133.65 | 177.91 |

TH: Test High-Fat Diet
TL: Test Fasting Low-Fat Diet
RH: Reference High-Fat Diet
RL: Reference Fasting Low-Fat Diet

TABLE 16

Summary Pharmacokinetic Parameters
as a Function of Food (Total EPA)

| Conditions | Dependent | Ref. | Test | Ratio % Ref | Lower 90% CI | Upper 90% CI |
|---|---|---|---|---|---|---|
| Fasted/Low Fat Diet | $Ln(C_{max})$ | RL | TL | 2178.42 | 1779.55 | 2666.70 |
| | $Ln(AUC_{0 \to \tau})$ | RL | TL | 2015.75 | 1563.65 | 2598.57 |
| Fed/High Fat Diet | $Ln(C_{max})$ | RH | TH | 182.22 | 146.17 | 227.16 |
| | $Ln(AUC_{0 \to \tau})$ | RH | TH | 172.55 | 153.26 | 194.26 |

TH: Test High-Fat Diet
TL: Test Fasting Low-Fat Diet
RH: Reference High-Fat Diet
RL: Reference Fasting Low-Fat Diet These data show that EPA plasma concentrations and total exposures were higher for both the Test and Reference when administered in the fed/high-fat diet state. The EPA exposure for the Test (EPA free fatty acid) is much higher than the Reference (EPA ethyl ester in a soft gel capsule) under fasting conditions/low fat diet; the Reference exposure is extremely low. Food has a much smaller effect on the Test as compared to the Reference.

Surprisingly, under fasted/low fat conditions, the bioavailability of the Test pharmaceutical composition was ~2000% greater than the RLD. Under fed (high-fat) conditions, the bioavailability the Test pharmaceutical composition was ~70-80% higher than the RLD.

This study showed that food and the fat content of food has a significant effect on the bioavailability of the RLD, whereas food has a much smaller effect on the bioavailability of the Test EPA free fatty acid enteric soft capsules. The absorption of EPA free fatty acid in the intestine diminishes the effect of food on absorption. Accordingly, the Test pharmaceutical composition, as described herein, does not require high fat meals to facilitate bioavailability of the EPA free fatty acid active pharmaceutical ingredient. The high bioavailability may be used to reduce the dosage quantity (e.g., 1 g instead of 4 g) required to achieve a therapeutic effect and may lead to better patient compliance.

These findings are advantageous for the treatment of patients with elevated triglyceride levels because these patients often have a controlled, low-fat diet as part of their therapy and thus they should not consume high fat meals. In addition, because the Test pharmaceutical composition does not contain docosahexaenoic acid (DHA), no increases in low-density lipoprotein levels (LDL) are expected in patients receiving this composition. This may provide a valuable therapeutic option for treating patients with very high triglycerides (e.g., severe hypertriglyceridemia; TG≥500 mg/dL) and those with high triglycerides (e.g., 200-500 mg/dL). Further, the controlled release enteric soft capsules reduce the incidence of "fishy burps"—eructation with fishy aftertaste or odor—because this pharmaceutical composition does not dissolve and release the EPA oil in the stomach.

What is claimed is:

1. An oral pharmaceutical composition comprising an enteric soft capsule shell comprising gelatin and an enteric polymer
wherein a weight ratio of the enteric polymer and gelatin is 1:2.6; and
wherein the shell encapsulates a matrix fill comprising at least 94% by weight eicosapentaenoic free fatty acid (EPA) and less than 1% by weight docosahexaenoic acid (DHA).

2. The composition of claim 1, wherein upon administration to a subject, an EPA $C_{max}$ ratio of a high-fat fed subject and a fasted subject fed a low-fat diet is less than 3:1.

3. The composition of claim 1, wherein the fill comprises about 250 mg to about 1000 mg of EPA.

4. The composition of claim 1, wherein upon administration to a subject, the subject experiences a minimal incidence of one or more of eructation, abdominal discomfort, nausea, diarrhea, fishy aftertaste, or fishy odor.

5. The composition of claim 1, wherein the capsule shell and matrix fill composition are stable for at least 1 year at 25° C., 60% relative humidity.

6. The composition of claim 1, wherein the capsule shell does not dissolve in simulated gastric fluid (pH 1.2) for at least 1 hour, and begins dissolution in simulated intestinal fluid (pH 6.8) within about 15 minutes.

7. The composition of claim 1, wherein upon administration to a subject the composition provides a mean plasma EPA $C_{max}$ of about 122 mg/L to about 226 mg/L and one or more of the following pharmacokinetic parameters:
(a) a mean plasma EPA $T_{max}$ of about 5 hours to about 6 hours;
(b) a mean plasma EPA $AUC_{0 \to \tau}$ of about 1840 h·mg/L to about 2860 h·mg/L;
(c) a mean plasma EPA $AUC_{0 \to \infty}$ of about 2040·mg/L to about 3000 mg/L;
(d) a mean EPA half-life (t½) of about 37 hours to about 43 hours; or
(e) a mean EPA overall elimination rate constant ($k_{e1}$) of about 0.019 $h^{-1}$ to about 0.020 $h^{-1}$.

8. The composition of claim 1, wherein upon administration to a subject the composition provides one or more of the following pharmacokinetic parameters:
(a) a mean plasma EPA $T_{max}$ of about 6 hours under fasting/low fat conditions;
(b) a mean plasma EPA $C_{max}$ of about 122 mg/L under fasting/low fat conditions;
(c) a mean plasma EPA $AUC_{0 \to \tau}$ of about 1840 h·mg/L under fasting/low fat conditions;
(d) a mean plasma EPA $AUC_{0 \to \infty}$ of about 2040·mg/L under fasting/low fat conditions;
(e) a mean EPA half-life (t½) of about 43 hours under fasting/low fat conditions; or
(f) a mean EPA overall elimination rate constant ($k_{e1}$) of about 0.019 $h^{-1}$ under fasting/low fat conditions;
or
(g) a mean plasma EPA $C_{max}$ of about 226 mg/L under fed/high fat conditions;
(h) a mean plasma EPA $AUC_{0 \to \tau}$ of about 2860 h·mg/L under fed/high fat conditions;
(i) a mean plasma EPA $AUC_{0 \to \infty}$ of about 3000 mg/L under fed/high fat conditions.

9. The composition of claim 1, wherein upon administration to a subject, the EPA has a bioavailability of about 2000% of the bioavailability of a reference pharmaceutical composition comprising eicosapentaenoic ethyl ester under fasted/low fat conditions.

10. The composition of claim 9, wherein the reference pharmaceutical composition comprises eicosapentaenoic ethyl ester in a soft gel capsule.

11. The composition of claim 1, wherein upon administration to a subject the composition does not induce a substantial increase in LDL level relative to baseline.

12. The composition of claim 1, wherein the composition is useful for treating, retarding a progression of, delaying an onset of, prophylaxis of, amelioration of, or reducing symptoms of a cardiovascular-related disease, including but not limited to hyperlipidemia or hypertriglyceridemia.

13. The composition of claim 1, wherein the composition is useful for treating, retarding a progression of, delaying an onset of, prophylaxis of, amelioration of, or reducing symptoms a medical condition comprising: cardiovascular-related diseases, hyperlipidemia, hypertriglyceridemia, hypertension, hypercholesterolemia, mixed dyslipidemia, sitosterolemia, atherosclerosis, or a combination thereof.

14. The composition of claim 1, wherein the composition further comprises a plasticizer, an alkali-neutralizing agent, and a solvent.

15. The composition of claim 14, wherein the enteric polymer is an acrylic and methacrylic acid copolymer; the plasticizer is glycerol or triethyl citrate or a combination thereof; the alkali neutralizing agent is ammonium hydroxide or sodium hydroxide or a combination thereof; and the solvent is water.

16. The composition of claim 1, wherein the composition further comprises a fat soluble vitamin comprising vitamin A, vitamin D, vitamin E, or vitamin K.

17. The composition of claim 16, wherein the fat soluble vitamin comprises cholecalciferol (vitamin D).

18. The composition of claim 1, wherein the gelatin and enteric polymer comprise about 25% to about 50% of the enteric soft capsule shell by weight.

19. A method for treating or reducing symptoms of a cardiovascular-related disease comprising administering to a subject in need thereof an oral pharmaceutical composition comprising an enteric soft capsule shell comprising gelatin and an enteric polymer;
wherein a weight ratio of the enteric polymer to gelatin is 1:2.6; and
wherein the shell encapsulates a matrix fill comprising at least 94% by weight eicosapentaenoic free fatty acid (EPA) and less than 1% by weight docosahexaenoic acid (DHA), wherein upon administration, the subject experiences a minimal incidence of one or more of eructation, abdominal discomfort, nausea, diarrhea, fishy aftertaste or fishy odor.

20. The method of claim 19, wherein the cardiovascular-related disease comprises hyperlipidemia, hypertriglyceridemia, hypertension, hypercholesterolemia, mixed dyslipidemia, sitosterolemia, atherosclerosis, or a combination thereof.

* * * * *